(12) United States Patent
Gerber et al.

(10) Patent No.: US 8,554,331 B2
(45) Date of Patent: Oct. 8, 2013

(54) THERAPY PROGRAM MODIFICATION

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 270 days.

(21) Appl. No.: 12/989,763

(22) PCT Filed: Jan. 23, 2009

(86) PCT No.: PCT/US2009/031801
§ 371 (c)(1),
(2), (4) Date: Oct. 26, 2010

(87) PCT Pub. No.: WO2009/134477
PCT Pub. Date: Nov. 5, 2009

(65) Prior Publication Data
US 2011/0046697 A1    Feb. 24, 2011

Related U.S. Application Data

(60) Provisional application No. 61/048,741, filed on Apr. 29, 2008.

(51) Int. Cl.
*A61N 1/00*    (2006.01)
(52) U.S. Cl.
USPC .................................. 607/59; 607/46; 607/60
(58) Field of Classification Search
USPC ................................................ 607/46, 59–60
See application file for complete search history.

(56) References Cited

U.S. PATENT DOCUMENTS 6,842,643 B1   1/2005  Schwartz et al.
7,136,707 B2  11/2006  Hall et al.
7,239,916 B2   7/2007  Thompson et al.
2004/0147978 A1  7/2004  Bernhard et al.
2004/0158298 A1  8/2004  Gliner et al.
(Continued)

FOREIGN PATENT DOCUMENTS

EP  0811395  12/1997
WO  0209808   2/2002

OTHER PUBLICATIONS

International Preliminary Report on Patentability for corresponding patent application No. PCT/US2009/031801, dated Nov. 11, 2010, 9 pages.
Written Opinion of the International Searching Authority for corresponding patent application No. PCT/US2009/031801, dated Sep. 28, 2009, 7 pages.

(Continued)

*Primary Examiner* — Nicole F Lavert
(74) *Attorney, Agent, or Firm* — Shumaker & Sieffert, P.A.

(57) ABSTRACT

A therapy program may be generated based on an algorithmic model of a baseline therapy field, which may represent a therapy field resulting from therapy delivery via the first therapy system based on a first therapy program. A second therapy program that controls therapy delivery by a second therapy system may be generated based on the baseline therapy field model. For example, therapy parameter values of the second therapy program may be selected to maintain at least one field characteristic of the baseline therapy field model. In some examples, the second therapy system may result from a hardware modification to the first therapy system. In other examples, the first and second therapy systems may be associated with different patients. For example, the baseline therapy field model may be an efficacious therapy field for a patient class, and a second therapy program may be generated for a patient in the class.

43 Claims, 24 Drawing Sheets

(56) References Cited

U.S. PATENT DOCUMENTS

2004/0215291 A1 10/2004 Van Bentem
2005/0060009 A1 3/2005 Goetz
2006/0259097 A1* 11/2006 Hickman et al. ............... 607/60

OTHER PUBLICATIONS

International Search Report for corresponding patent application No. PCT/US2009/031801, dated Sep. 28, 2009, 4 pages.

* cited by examiner

THERAPY PROGRAM MODIFICATION

This application claims the benefit of and is a U.S. National Stage filing under 35 U.S.C. §371 of PCT Application Serial No. PCT/US09/031801, filed Jan. 23, 2009 and entitled, "Therapy Program Modification," which in turn claims the benefit of U.S. Provisional Application No. 61/048,741, filed Apr. 29, 2008 and entitled "Therapy Program Modification." The entire disclosure of PCT Application Serial No. PCT/US09/031801 and U.S. Provisional Application No. 61/048, 741 is incorporated by reference herein in its entirety.

TECHNICAL FIELD

The disclosure relates to medical devices, and, more particularly, systems and methods for modifying therapy programs for therapy delivered by medical devices.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some cases, the electrical stimulation may be used for muscle stimulation, e.g., functional electrical stimulation (FES) to promote muscle movement or prevent atrophy. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

During a programming session, which may occur during implant of the medical device, during a trial session, or during a follow-up session after the medical device is implanted in the patient, a clinician may select therapy parameters for the medical device that provide efficacious therapy to the patient. In the case of electrical stimulation, the therapy parameters may include an electrode combination, and an amplitude, which may be a current or voltage amplitude, a pulse width, and a pulse rate for stimulation signals to be delivered to the patient. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

A group of therapy parameter values may be referred to as a therapy program. A medical device may deliver therapy to a patient according to one or more stored therapy programs.

SUMMARY

In general, the disclosure is directed to devices, systems, and methods for generating a therapy program to substantially maintain at least one characteristic of an algorithmic model of a baseline therapy field. The therapy program may be generated for use with a therapy system that differs from the therapy system on which the baseline therapy field is based. A therapy field may represent a region of the patient's tissue to which therapy is delivered. In some examples described herein, the therapy field may include an electrical field that is generated by a medical device that delivers electrical stimulation to the patient and a therapy program defining stimulation parameters, where the electrical field represents the regions of tissue that will be covered by an electrical field during therapy. In other examples, the therapy field may be a tissue activation field, which indicates the nerve or muscle tissue that will be activated by the electrical field in a target anatomical region of the patient.

A clinician may select a first therapy program that defines values for therapy parameters that provide efficacious therapy to a patient when the therapy is delivered by a first therapy system. The first therapy system may include an external or implantable medical device and at least one therapy delivery element. In the case of electrical stimulation therapy, the medical device may include an electrical stimulator and the therapy delivery element may include one or more medical leads. An algorithmic model of a baseline therapy field may be generated based on the first therapy program and the first therapy system. The algorithmic model of the baseline therapy field may indicate the region of the patient's tissue to which therapy is delivered when the first therapy system delivers therapy with the parameter values defined by the first therapy program. In this way, the baseline therapy field may represent a therapy field known to result in efficacious therapy to the patient.

During the course of therapy planning or during the course of chronic therapy delivery, the first therapy system may be modified. For example, an additional therapy delivery element may be added to the first therapy system or another generation of the medical device may be substituted for the medical device of the first therapy system. Therapy delivery by the modified therapy system according to the first therapy program may result in a different therapy field than the therapy delivery by the first therapy system. Accordingly, in order to substantially maintain the efficacy of therapy, a second therapy program for the second therapy system may be generated based on the algorithmic model of the baseline therapy field. The parameter values of the second therapy program may be selected such that therapy delivery by the modified therapy system based on the second therapy program substantially maintains at least one field characteristic of the algorithmic model of the baseline therapy field. In the case of electrical stimulation therapy, the field characteristic may include, for example, an area of activated tissue, a centroid of stimulation, an area of stimulation, recruited neurons, an amplitude of the voltage or current at a certain spatial point within stimulation area, a charge density, or the like.

The therapy programs for the first therapy system and the modified therapy system may differ. For example, the medical devices of the first system and the modified therapy system may have different maximum energy outputs, which may affect the voltage or current amplitude or pulse width of a therapy program.

In another example, the algorithmic model of the baseline therapy field may be a therapy field known to be effective for a class of patients, such as patients with similar patient conditions. The algorithmic model of the baseline therapy field may be generated based on a first therapy system associated with a first patient or a first group of patients. The therapy parameter values useful for generating a therapy field similar to the algorithmic model of the baseline therapy field may differ depending upon the hardware characteristics of a specific patient's therapy system. Accordingly, in some examples, the known efficacy of the baseline therapy field may be replicated for a specific patient in the class and the specific therapy system (e.g., a "second" therapy system) implemented for the specific patient by generating a therapy program for the specific patient's therapy system based on the algorithmic model of the baseline therapy field. Thus, in some examples, the algorithmic model of the baseline therapy field may be generated based on therapy delivery by a first therapy system associated with a first patient, and the second therapy program may be generated to control therapy delivery by a second therapy system associated with a second patient that is different than the first patient.

In one aspect, the disclosure is directed to a method comprising receiving a first user-defined therapy program that controls therapy delivery via a first therapy system, generating an algorithmic model of a baseline therapy field that represents the therapy delivery via the first therapy system based on the first user-defined therapy program, and automatically generating a second therapy program for a second therapy system based on the algorithmic model of the baseline therapy field, where the second therapy system differs from the first therapy system.

In another aspect, the disclosure is directed to a method comprising generating an algorithmic model of a first therapy field based on delivery of therapy by a first therapy system in accordance with a therapy program, where the first therapy system comprises a medical device and a therapy delivery element, receiving information relating to a modification to at least one of the medical device or the therapy delivery element of the first therapy system, where the information defines a modified therapy system, generating an algorithmic model of a second therapy field based on delivery of therapy by the modified therapy system in accordance with the therapy program, comparing the algorithmic models of the first and second therapy fields, and modifying the therapy program based on the comparison between the algorithmic models of the first and second therapy fields.

In another aspect, the disclosure is directed to a system comprising a memory that stores a first therapy program and an algorithmic model of a baseline therapy field, and a processor that generates the algorithmic model of a baseline therapy field that is based on therapy delivery via a first therapy system in accordance with the first therapy program and automatically generates a second therapy program for a second therapy system based on the algorithmic model of the baseline therapy field, where the second therapy system differs from the first therapy system.

In another aspect, the disclosure is directed to a computer-readable medium containing instructions. The instructions cause a programmable processor to receive a first user-defined therapy program that controls therapy delivery via a first therapy system, generate an algorithmic model of a baseline therapy field that represents the therapy delivery via the first therapy system based on the first user-defined therapy program, and automatically generate a second therapy program for a second therapy system based on the algorithmic model of the baseline therapy field, where the second therapy system differs from the first therapy system.

In another aspect, the disclosure is directed to a system comprising means for receiving a first user-defined therapy program that controls therapy delivery via a first therapy system, means for generating an algorithmic model of a baseline therapy field that represents the therapy delivery via the first therapy system based on the first user-defined therapy program, and means for automatically generating a second therapy program for a second therapy system based on the algorithmic model of the baseline therapy field, where the second therapy system differs from the first therapy system.

DETAILED DESCRIPTION

Figure 1:
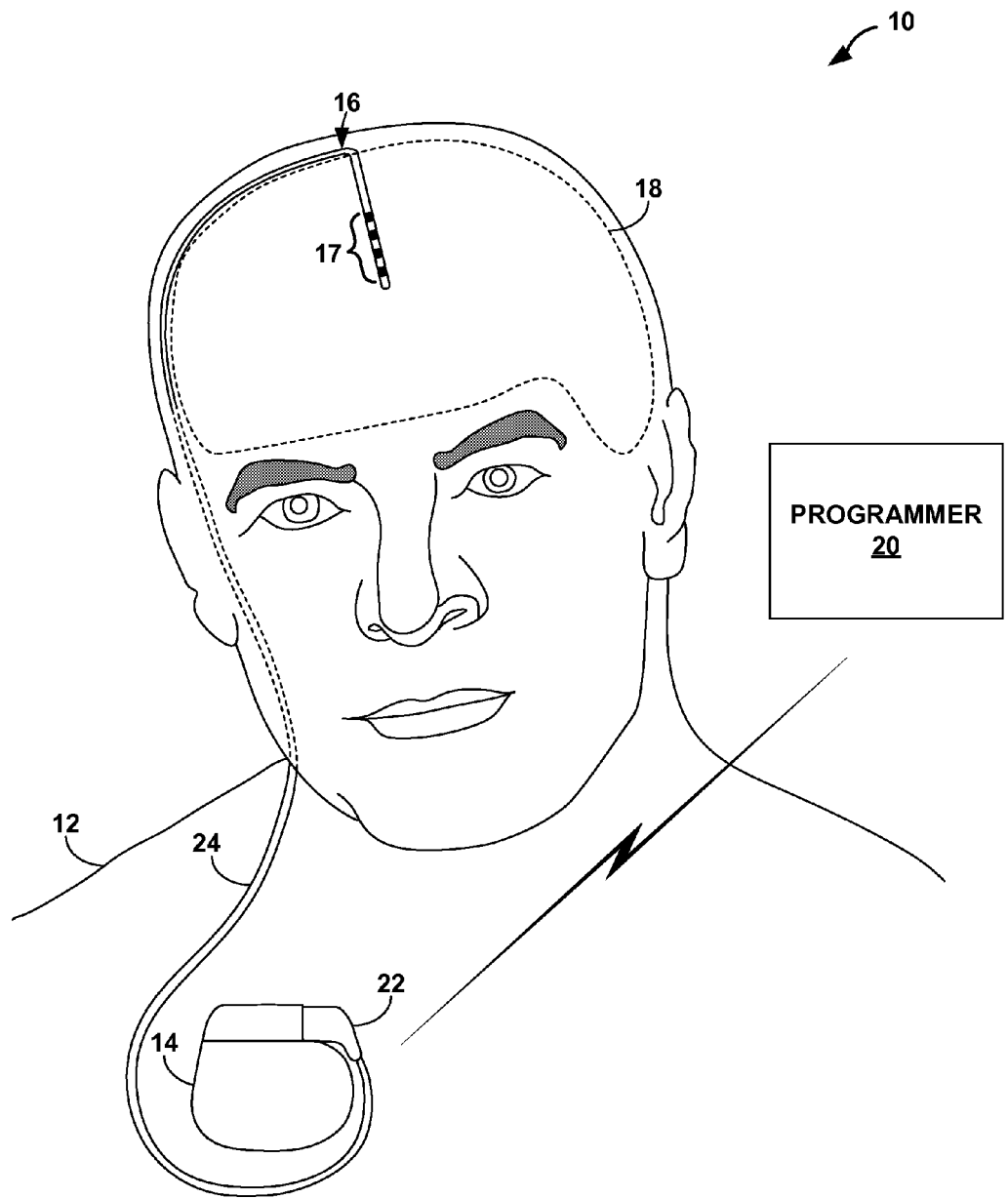
FIGS. 1 and 2 are conceptual diagrams illustrating example therapy systems that provide electrical stimulation therapy to a patient.

FIG. 1 is a conceptual diagram illustrating an example therapy system 10 that provides electrical stimulation therapy to patient 12. Therapy system 10 includes IMD 14 and medical lead 16. In the example shown in FIG. 1, IMD 14 delivers deep brain stimulation (DBS) to tissue within brain 18 of patient 12 in order to alleviate or otherwise manage a condition of patient 12. Lead 16 is implanted within patient 12 such that one or more electrodes 17 carried by lead 16 are located proximate to a target tissue site within brain 18. In some examples, more than one lead 16 may be implanted within brain 18 of patient 12 to provide stimulation to multiple tissue sites (e.g., different brain structures, or the same structure within different hemispheres) within brain 18. As shown in FIG. 1, system 10 may also include a programmer 20, which may be a handheld device, portable computer, or workstation that provides a user interface to a clinician or other user. The clinician may interact with the user interface to program stimulation parameters for IMD 14, which may include, for example, the electrodes 17 that are activated, the polarity of the electrodes 17, a current or voltage amplitude of the stimulation signal, a slew rate, duty cycle, and, in the case of stimulation in the form of electrical pulses, pulse width and pulse rate (or frequency) for stimulation signals to be delivered to patient 12.

DBS lead 16 includes one or more electrodes 17 placed along the longitudinal axis of lead 16. In some examples, electrodes 17 may include at least one ring electrode that resides along the entire circumference of lead 16. Electrical current from a ring electrode propagates in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects.

In other examples, electrodes 17 of lead 16 may include a complex electrode array geometry that includes segmented or partial ring electrodes in addition to or instead of ring electrodes. The electrodes in a complex electrode array may be located at different axial positions and angular positions around the circumference or periphery of the lead, as well as at different longitudinal positions, which are measured along the longitudinal axis of lead 16. A complex electrode array geometry may be useful for customizing the stimulation field and provide improved therapy while decreasing side effects. For example, with a complex electrode array, electrodes may be selected along the longitudinal axis of lead 16 and about the periphery of lead 16. Selectively activating electrodes 17 of lead 16 can produce customizable stimulation fields that may be directed to a particular side of lead 16 in order to isolate the stimulation field around the target anatomical region of brain 18. In this manner, specific electrodes of the complex electrode array geometry may be selected to produce a stimulation field at desired portions of the circumference instead of always producing a stimulation field around the entire circumference or periphery of the lead, as with some ring electrodes.

While both ring electrodes and a complex electrode geometry may provide efficacious therapy to patient 12, in some cases, producing irregular stimulation fields with a lead 16 with a complex electrode geometry may allow therapy system 10 to more accurately and precisely target certain anatomical regions of brain 18 when compared to a lead 16 with ring electrodes. In addition, therapy system 10 including a complex electrode geometry may also reduce or eliminate side effects from more spherical stimulation fields produced by a conventional array of ring electrodes. The center of the stimulation field may be moved away from lead 16 to avoid unwanted stimulation or compensate for inaccurately placed leads.

In the example shown in FIG. 1, lead 16 is coupled to IMD 14 via connector 22, which defines a plurality of electrical contacts for electrically coupling electrodes 17 to a stimulation generator within IMD 14. Connector 22 may also be referred to as a connector block 22 or a header 22 of IMD 14. In the example shown in FIG. 1, lead 16 is indirectly coupled to connector 22 with the aid of lead extension 24. In some examples, lead 16 may be directly coupled to connector 22 without the aid of extension 24.

Programmer 20 is an external computing device that is configured to wirelessly communicate with IMD 14. For example, programmer 20 may be a clinician programmer that the clinician uses to communicate with IMD 14. Alternatively, programmer 20 may be a patient programmer that allows patient 12 to view and modify therapy parameters. The clinician programmer may include more programming features than the patient programmer. In other words, more complex or sensitive tasks may only be performed with the clinician programmer to prevent patient 12 from making undesired changes to the operation of IMD 14.

Programmer 20 may be a hand-held computing device that includes a display viewable by the user (e.g., a clinician or patient 12) and a user input mechanism that can be used to provide input to programmer 20. For example, programmer 20 may include a small display screen (e.g., a liquid crystal display or a light emitting diode display) that presents information to the user. In addition, programmer 20 may include a keypad, buttons, a peripheral pointing device, touch screen or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone or personal digital assistant that is configured to run an application that simulates one or more functions of programmer 20. Alternatively, a notebook computer, tablet computer, desktop computer, or other personal computer may run an application that enables the computer to function as programmer 20. A wireless adapter may be connected to the personal computer to enable to the computer to securely communicate with IMD 14.

When programmer 20 is configured for use by the clinician, programmer 20 may be used to transmit initial programming information to IMD 14. This initial information may include hardware information of therapy system 10, such as the type of lead 16, the position of lead 16 within patient 12, the therapy parameters of therapy programs stored within IMD 14 or within programmer 20, and any other information the clinician desires to program into IMD 14.

With the aid of programmer 20 or another computing device, a clinician may select values for therapy parameters for therapy system 10. The therapy parameters may be organized into a group of parameters referred to as a "therapy program." In the case of electrical stimulation, the therapy parameters may include a slew rate, a duty cycle, an electrode combination, and an amplitude, which may be a current or voltage amplitude, and, in the case of stimulation pulses, a pulse width and a pulse rate (or frequency) for stimulation signals to be delivered to the patient. An electrode combination may include a selected subset of one or more electrodes 17 located on one or more implantable leads 16 coupled to IMD 14. The electrode combination may also refer to the polarities of the electrodes in the selected subset. By selecting particular electrode combinations, a clinician may target particular structures within brain 18. In addition, by selecting values for amplitude, pulse width, and pulse rate, the clinician may generate an efficacious therapy for patient 12 that is delivered via the selected electrode subset. Due to physiological diversity, differences in patient condition, and inaccuracies in lead placement, the parameters may vary between patients.

During a programming session, the clinician may determine one or more therapy programs that may provide effective therapy to patient 12. Patient 12 may provide feedback to the clinician as to the efficacy of the specific program being evaluated, which may include information regarding side effects of delivery of therapy according to the specific program and the extent to which the therapy mitigates one or more symptoms of the patient condition. Once the clinician has identified one or more programs that may be beneficial to patient 12, patient 12 may continue the evaluation process and determine which program best alleviates the condition of patient 12 or otherwise provides efficacious therapy to patient 12. Programmer 20 may assist the clinician in the creation/identification of therapy programs by providing a methodical system of identifying potentially beneficial therapy parameters.

In some examples, the clinician may select therapy parameters using the techniques described in commonly-assigned U.S. Pat. No. 7,822,483 issued on Oct. 26, 2010 to Stone et al., entitled, "ELECTRICAL AND ACTIVATION FIELD MODELS FOR CONFIGURING STIMULATION THERAPY" and filed on Oct. 31, 2006, and commonly-assigned U.S. Patent Application Publication No. 2007/0203541 by Goetz et al., entitled, "PROGRAMMING INTERFACE WITH A CROSS-SECTIONAL VIEW OF A STIMULATION LEAD WITH COMPLEX ELECTRODE ARRAY GEOMETRY," and filed on Oct. 31, 2006. The entire content of U.S. Pat. No. 7,822,483 and U.S. Patent Application Publication No. 2007/0203541 is incorporated herein by reference. U.S. Pat. No. 7,822,483 and U.S. Patent Application Publication No. 2007/0203541 describe programming systems and methods that support the programming of stimulation parameters with a therapy system 10 including a lead 16, which may include a complex electrode array geometry.

In accordance with techniques described in U.S. Pat. No. 7,822,483 to Stone et al., a user interface of programmer 20 may display a representation of the anatomical regions of patient 12, specifically anatomical regions of brain 18. The three-dimensional (3D) space of the anatomical regions may be displayed as multiple two-dimensional (2D) views or a 3D visualization environment. Lead 16 may also be represented on the display of the user interface and positioned relative to the representation of brain 18 shown on the display of programmer 20 according to the actual implantation location by the clinician or directly from an image taken of the lead within brain 18.

The clinician may interact with the user interface of programmer 20 to manually select and program certain electrodes 17 of lead 16, adjust the resulting stimulation field with the anatomical regions as guides or define one or more stimulation fields that only affect anatomical regions of interest. Once the clinician has defined the one or more stimulation fields, programmer 20 may automatically generate the stimulation parameter values associated with each of the stimulation fields and transmit the parameters, which may be stored as a therapy program, to IMD 14. The stimulation parameter values associated with a stimulation field may be the parameter values that result in the generation of the stimulation field when therapy system 10 delivers therapy according to the stimulation parameter values.

In accordance with techniques described in U.S. Patent Application Publication No. 2007/0203541 by Goetz et al., programmer 20 may present a user interface that displays electrodes of lead 16 and enables a user to select individual electrodes to form an electrode combination and specify parameters for stimulation delivered via the electrode combination. In accordance with other techniques described in U.S. Patent Application Publication No. 2007/0203541 by Goetz et al., programmer 20 may present a user interface to a user that enables the user to manipulate a representation of an electrical stimulation field (i.e., one type of therapy field) produced by a selected electrode combination. A processor within programmer 20 may then select the appropriate electrode combination, electrode polarities, amplitudes, pulse widths, and pulse rates of electrical stimulation sufficient that best fit a stimulation field created by a user via a user interface of programmer 20.

Programmer 20 may also be configured for use by patient 12. When configured as the patient programmer, programmer 20 may have limited functionality in order to prevent patient 12 from altering critical functions or applications that may be detrimental to patient 12. In this manner, programmer 20 may only allow patient 12 to adjust certain therapy parameters or set an available range for a particular therapy parameter. Programmer 20 may also provide an indication to patient 12 when therapy is being delivered or when IMD 14 or when the power source within programmer 20 or IMD 14 need to be replaced or recharged.

Whether programmer 20 is configured for clinician or patient use, programmer 20 may communicate to IMD 14 or any other computing device via wireless communication. Programmer 20, for example, may communicate via wireless communication with IMD 14 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 14 and other another programmer via remote telemetry techniques known in the art, communicating via a local area network (LAN), wide area network (WAN), public switched telephone network (PSTN), or cellular telephone network, for example.

DBS may be used to treat or manage various patient conditions, such as, but not limited to, seizure disorders (e.g., epilepsy), pain, migraine headaches, psychological disorders (e.g., mood or anxiety disorders), movement disorders (e.g., essential tremor or Parkinson's disease), Huntington's disease, and other neurodegenerative disorders. During implantation of lead 16 within patient 12, a clinician may attempt to position electrodes 17 of lead 16 close to or within a target anatomical region. The anatomical region within patient 12 that serves as the target tissue site for stimulation delivered by IMD 14 may be selected based on the patient condition. For example, stimulating particular structures of brain 18, such as the Substantia Nigra, may help reduce the number and magnitude of tremors experienced by patient 12. Other example anatomical regions for DBS may include the subthalamic nucleus, globus pallidus interna, ventral intermediate, and zona inserta.

While DBS may successfully reduce symptoms of some neurological diseases, the stimulation may also cause undesirable side effects. Side effects may include incontinence, tingling, loss of balance, paralysis, slurred speech, loss of memory, loss of inhibition, and many other neurological problems. Side effects from DBS may be mild to severe. DBS may cause one or more side effects by inadvertently providing electrical stimulation pulses to anatomical regions near the targeted anatomical region. For this reason, a clinician may generate a therapy program (or a plurality of therapy programs) that defines stimulation parameter values that balance effective therapy and minimize side effects.

In other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver electrical stimulation or a therapeutic agent to tissue proximate to a pudendal nerve, a perineal nerve or other areas of the nervous system, in which cases, lead 16 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain). In addition, although a single lead 16 is shown in FIG. 1, in some therapy systems, two or more leads may be electrically coupled to IMD 14.

Figure 2:
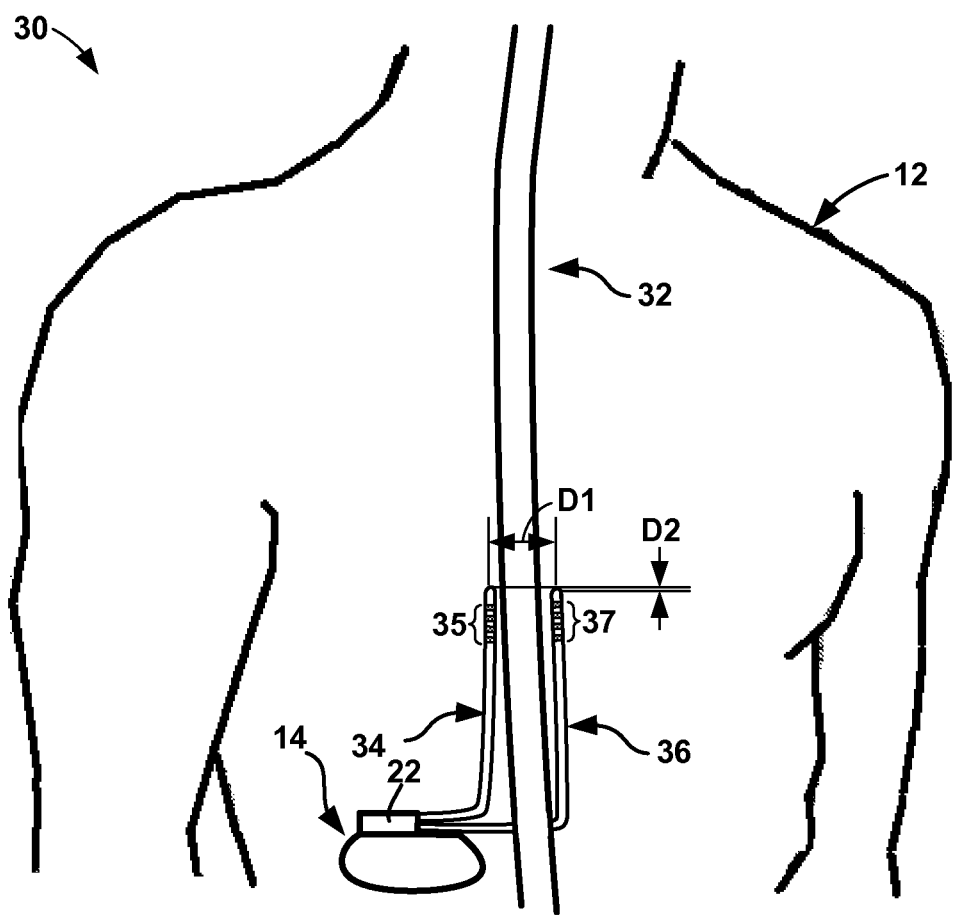

FIG. 2 is a conceptual diagram of another example therapy system 30 that delivers electrical stimulation to target tissue sites proximate to spine 32 of patient 12. Therapy system 30 includes IMD 14, which is coupled to leads 34, 36 via connector 22. Leads 34, 36 each include an array of electrodes 35, 37, respectively. IMD 14 may deliver stimulation to patient 12 via a combination of electrodes 35, 37. Electrodes 35, 37 may each be any suitable type of electrode, such as a ring electrode, partial ring electrode or segmented electrode.

In the example shown in FIG. 2, leads 34, 36 are positioned to deliver bilateral stimulation to patient 12, i.e., stimulation signals are delivered to target tissue sites on opposite sides of a midline of patient 12. The midline may be generally defined by spinal cord 32. Just as with therapy system 10, a clinician may generate one or more therapy programs for therapy system 30 by selecting therapy parameters that provide efficacious therapy to patient 12 with the aid of programmer 20 or another computing device. The therapy parameters may include, for example, the combination of the electrodes of lead 16, the slew rate, duty cycle, voltage or current amplitude, pulse width, and/or frequency of a stimulation signal.

A distance between leads 34, 36, and, more specifically, a distance between electrodes 35, 37 of leads 34, 36 may affect the therapy field that results from electrical stimulation delivered by IMD 14 according to a therapy program. For example, the further apart electrodes 35, 37 are spaced from each other in either or both the left/right (laterally) direction or the dorsal/ventral direction (distance D1, shown schematically in FIG. 1B) or in the superior-inferior direction (distance D2, shown schematically in FIG. 1B), the less overlap there may be in stimulation propagating from electrodes 35, 37, which may affect the neurons that are activated by the electrical field. As another example, if one or both of leads 34 and 36 move, the electrodes 35 and 37 may shift and the centroid of stimulation may change, which may affect the efficacy of therapy. Distance D1 may be measured, e.g., from a longitudinal axis of lead 34 to a longitudinal axis of lead 36, and may traverse more than one direction, i.e., may extend both laterally, in a left/right direction and in a dorsal/ventral direction. Distance D2 may be measured, e.g., from the distal end of lead 34 to the distal end of lead 36.

Electrodes 17, 35, 37 of leads 16, 34, 36, respectively, may also be used to sense one or more physiological parameters of patient 12. For example, in some examples, electrodes 17 (FIG. 1), 35, 37 may also include at least one sense electrode that senses a physiological parameter of patient 12, such as, but not limited to, a heart rate, respiration rate, respiratory volume, core temperature, muscular activity, impedance, electromyogram (EMG), an electroencephalogram (EEG), an electrocardiogram (ECG) or galvanic skin response. In addition, therapy systems 10, 30 may include other physiological sensors, such as sensors that sense the blood pressure, blood oxygen saturation, partial pressure of oxygen within blood, partial pressure of oxygen within cerebrospinal fluid or arterial blood flow of patient 12. Therapy systems 10, 30 may include other types of sensors, such as sensors to detect activity, activity level, posture, or a physiological parameter of patient 12. The sensors may be wirelessly coupled to IMD 14 or via a lead. For example, the sensors may be implanted within patient 12 at a different site than IMD 14 or the sensors may be external.

For therapy system 10 (FIG. 1), therapy system 30 (FIG. 2) or any other therapy system that provides electrical stimulation therapy to patient 12, an algorithmic model of a baseline therapy field that provides efficacious therapy to patient 12 may be generated with the aid of modeling software, hardware or firmware executing on a computing device, such as programmer 20 or a separate dedicated or multifunction computing device. The baseline therapy field model may be stored within a memory of programmer 20, IMD 14 or another device. The algorithmic model of the baseline therapy field is a known therapy field that results from delivery of stimulation according to at least one therapy program determined to deliver efficacious therapy to the patient, and may be based on the patient's anatomy, such as the tissue characteristics at the target tissue site (e.g., the impedance of the tissue).

The algorithmic model of the baseline therapy field may include an electrical field model, activation field model, or a model illustrating the voltage gradient or current density of electrical stimulation that balances effective therapy and minimal side effects for patient 12 or for a class of patients (e.g., a class of patients having similar patient conditions). The electrical field model may represent the areas of a patient anatomical region that will be covered by an electrical field during therapy. The activation field model may indicate the neurons that will be activated by the electrical field in the patient anatomical region covered by the stimulation therapy, thereby indicating the tissue area activated by the electrical stimulation. The voltage gradient or current density model may indicate the voltage gradient or current density of an electrical field that provides efficacious therapy to patient 12.

While the remainder of the description of FIGS. 3-24 primarily refers to therapy system 10 of FIG. 1, in other examples, the techniques for generating an algorithmic model of a baseline therapy field and modifying a therapy program based information indicative of a change in a therapy field may be applied to spinal cord stimulation therapy system 30 of FIG. 2. In addition, while the remainder of the description primarily refers to an algorithmic model of a baseline therapy field that is generated with the aid of modeling software executing on a computing device, in other examples, the algorithmic model of a baseline therapy field may be generated with the aid of hardware or firmware of a computing device.

In some examples, the modeling software implements an algorithm that models a baseline therapy field based on an anatomy of patient 12, the therapy program determined to provide efficacious therapy to patient 12, and the hardware characteristics of therapy system 10. The algorithm for generating the baseline therapy model as well as other therapy models may be stored within a memory of programmer 20, IMD 14 or another device. In the case of therapy system 10 (FIG. 1), the hardware characteristics may include the type of IMD 14, such as an energy threshold value of IMD 14 or the one or more channels of IMD 14, the number of available channels for delivering stimulation signals to a target tissue site within patient 12, power source limitations of IMD 14, and the like. The energy threshold value may be substantially equal to the maximum energy output of IMD 14 or for one or more of the channels of IMD 14. In other cases, IMD 14 may be capable of generating a stimulation signal having an energy greater than or equal to an energy threshold value, but it may be undesirable for IMD 14 to provide such a stimulation signal for purposes of energy efficiency of therapy system 10, e.g., in order to help extend the life of the power source within IMD 14. Thus, the energy threshold value may indicate a desirable energy limitation for stimulation signals generated and delivered by IMD 14.

The hardware characteristics of therapy system 10 may also include information relating to lead 16, such as the number or types of leads implanted within patient 12, the number of electrodes 17, the spacing of electrodes 17 on respective lead 16, the size of each of the electrodes 17, the type of electrodes 17 (e.g., ring electrodes, partial-ring electrodes, segmented electrodes), and the like. The hardware characteristics of therapy system 30 may also include a baseline distance D1 or D2 between leads 34, 36. For example, in the case of therapy system 30, the baseline spacing between electrodes 35, 37 of leads 34, 36 may be, for example, the spacing between electrodes 35, 37 at the time of implant of leads 34, 36.

In examples in which a clinician generates one or more therapy programs for therapy system 10 by selecting a stimulation field and subsequently generating the stimulation parameters that result in the selected stimulation field, the baseline therapy field model may be a digital model of the stimulation field selected by the clinician. For example, the algorithmic model of the baseline therapy field may be an electrical field model that is generated based upon patient anatomy data and a therapy program defining stimulation parameter values, where the electrical field model represents the areas of a patient anatomical region that will be covered by an electrical field during therapy. In particular, the electrical field model may represent where electrical stimulation propagates through tissue from electrodes 17 of lead 16. Patient anatomy data may indicate one or more characteristics of patient tissue proximate to an implanted lead 16, and may be created from any type of imaging modality, such as, but not limited to, computed tomography (CT), magnetic resonance imaging (MRI), x-ray, fluoroscopy, and the like.

In other examples, the algorithmic model of the baseline therapy field may be an activation field model that may be based on a neuron model that indicates one or more characteristics of patient neural tissue proximate to implanted lead 16. The activation field may indicate the neurons that will be activated by the electrical field in the anatomical region near lead 16. The clinician may program the therapy parameters for IMD 14 by selecting a desired activation field and generate therapy parameter values that may achieve the desired therapy field, taking into consideration the patient's anatomy (e.g., neural tissue characteristics) and the hardware characteristics of therapy system 10.

In other examples, an algorithmic model of the baseline therapy field may be generated after selecting therapy parameter values. For example, the clinician may select therapy parameter values that provide efficacious therapy to patient 12 and generate an algorithmic model of the therapy field resulting from the therapy parameter values with the aid of modeling software executing on a computing device, such as programmer 20 or a separate workstation or computing device. Again, the resulting therapy field may be based on an algorithmic model that is based on the therapy parameter values, the patient's anatomy, and the hardware characteristics of therapy system 10.

In each example, the algorithmic model of the baseline therapy field is associated with a first therapy program for therapy system 10. In general, the algorithmic model of the baseline therapy field may indicate the region of the patient's tissue to which therapy is delivered when therapy system 10 delivers therapy based on the first therapy program generated for therapy system 10.

In some examples, the algorithmic model of the baseline therapy field may be used to generate another therapy program for patient 12. For example, after the first therapy program is generated for therapy system 10, therapy system 10 may be modified, e.g., by replacing IMD 14 with another medical device or by modifying the number or types of leads 16 of therapy system 10. For example, an additional lead may be added to therapy system 10 or lead 16 may be replaced by another type of lead including a different number of electrodes or different spacing between electrodes. As another example, IMD 14 may be replaced by another generation or model of IMD 14, or, if therapy system 10 includes a trial medical device, which may be an external device, the modification may include replacing the trial device with a chronic implant. IMD 14 may be replaced by an IMD that has a different energy threshold value, different power source limitation or other hardware differences that may affect the acceptable stimulation parameter values for the replacement IMD. The acceptable stimulation parameter values may be, for example, the therapy parameter values determined to provide effective therapy to patient 12 or a patient with a similar patient condition.

In some cases, the therapy parameter values suitable for IMD 14 to generate a particular therapy field may not result in the same therapy when delivered by a different IMD. For example, a first therapy parameter value may correspond to a different value on a different IMD (e.g., a different generation of IMD 14) due to differences in construction of the therapy delivery module (e.g., circuitry), accuracy of the therapy delivery module, implementation of the therapy delivery module, and the like.

The algorithmic model of the baseline therapy field may provide guidance for generating one or more therapy programs for therapy delivery by a modified therapy system. A departure from the baseline therapy field may result in less efficacious therapy to patient 12, an increase in undesired side effects, or a combination thereof. Therapy delivery by a modified therapy system according to the first therapy program may result in a different therapy field than the therapy delivery by therapy system 10. Thus, the therapy delivery by the modified therapy system based on the first therapy program may result in a therapy field that differs in at least one field characteristics relative to the algorithmic model of the baseline therapy field. In the case of electrical stimulation therapy, the field characteristic may include, for example, a centroid of stimulation, an area of stimulation, recruited neurons, an amplitude of the voltage or current at a certain spatial point within stimulation area, a charge density, and the like.

In order to substantially maintain the efficacy of therapy, a second therapy program for the modified therapy system may be generated based on the algorithmic model of the baseline therapy field. The parameter values of the second therapy program may be selected such that therapy delivery by the modified therapy system based on the second therapy program substantially maintains at least one field characteristic of the algorithmic model of the baseline therapy field.

In other examples, the algorithmic model of the baseline therapy field may be used to generate another therapy program for patient 12. As previously indicated, the algorithmic model of the baseline therapy field may be a therapy field known to provide efficacious therapy to patient 12. In some cases, the algorithmic model of the baseline therapy field may be a therapy field known to provide efficacious therapy to a class of patients, and may be generated based on therapy delivery by a first therapy system according the therapy parameter values defined by a first therapy program. For example, the algorithmic model of the baseline therapy field may represent a target electrical field, activation field, anatomical structure, or the like, for managing a particular patient condition, such as a seizure disorder, movement disorder, psychiatric disorder or the like.

The clinician may generate the algorithmic model of the baseline therapy field based efficacy feedback from one patient representative of the class, or based on more than one patient representative of the class. For example, the clinician may select efficacious therapy parameter values for two or more patients, generate algorithmic models of therapy fields for the respective patients based on the therapy parameter values found to be effective, and determine which, if any, field characteristics of the resulting therapy fields are shared between the therapy fields associated with the two or more patients. These field characteristics may be used to characterize the algorithmic model of the baseline therapy field. As another example, the clinician may select efficacious therapy parameter values for one patient in the class and generate an algorithmic model of the therapy field resulting from therapy delivery according to the efficacious parameter values by the patient's therapy system. The generated algorithmic model may be stored as a baseline therapy field for generating therapy programs for patients in the same class.

Accordingly, in some examples, the algorithmic model of the baseline therapy field may be useful for generating a second therapy program for a second therapy system that is specific to a patient within the class of patients. The parameter values defined by the second therapy program may differ depending upon the hardware characteristics of a patient's therapy system. The known efficacy of the baseline therapy field may be replicated for a specific patient in the class and the specific therapy system implemented for the specific patient by generating the second therapy program for the specific patient's therapy system based on the algorithmic model of the baseline therapy field. Thus, in some examples, the algorithmic model of the baseline therapy field may be generated based on therapy delivery by a first therapy system 10 associated with a patient 12, and the second therapy program may be generated to control therapy delivery by a second therapy system associated with a second patient that is different than the first patient. The first and second patients may be members of a class of patients that share one or more symptoms and/or patient conditions.

Figure 3:
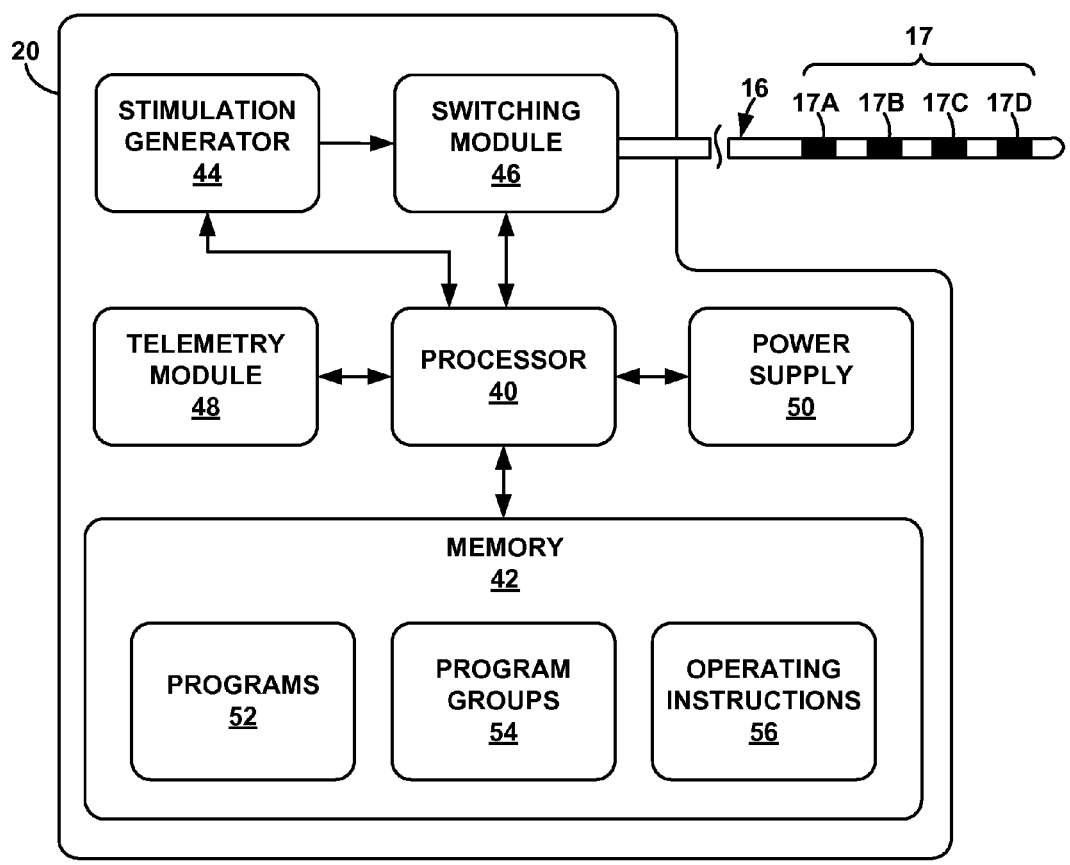
FIG. 3 is a functional block diagram of an example implantable medical device that generates electrical stimulation signals.

FIG. 3 is a functional block diagram of an example IMD 14. IMD 14 includes a processor 40, memory 42, stimulation generator 44, switching module 46, telemetry module 48, and power source 50. As shown in FIG. 3, stimulation generator 44 is coupled to lead 16. Alternatively, stimulation generator 44 may be coupled to two or more leads (e.g., as shown in FIG. 2), either directly or indirectly (e.g., via a lead extension, such as a bifurcated lead extension that may electrically and mechanically couple to two leads) as needed to provide stimulation therapy to patient 12.

In the example illustrated in FIG. 3, lead 16 includes electrodes 17A-17D (collectively referred to as "electrodes 17"). Electrodes 17 may be ring electrodes. In other examples, electrodes 17 may be arranged in a complex electrode array that includes multiple non-contiguous electrodes at different angular positions about the outer circumference of lead 16. The configuration, type, and number of electrodes 17 illustrated in FIG. 3 are merely exemplary. In other examples, IMD 14 may be coupled to any suitable number of leads with any suitable number and configuration of electrodes.

Memory 42 includes computer-readable instructions that, when executed by processor 40, cause IMD 14 to perform various functions. Memory 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 42 may include programs 52, program groups 54, and operating instructions 56 in separate memories within memory 42 or separate areas within memory 42. Each program 52 defines respective values for electrical stimulation parameters, such as an electrode combination, electrode polarity, current or voltage amplitude value, and, in the case of electrical stimulation pulses, pulse width and pulse rate. A program group 54 defines a group of programs that may be delivered together on an overlapping or non-overlapping basis. Operating instructions 56 guide general operation of IMD 14 under control of processor 40.

Stimulation generator 44 produces stimulation signals, which may be pulses as primarily described herein or continuous waveform signals, such as sine waves, for delivery to patient 12 via selected combinations of electrodes 17. Processor 40 controls stimulation generator 44 according to programs 52 and program groups 54 stored by memory 42 to apply particular stimulation parameter values specified by one or more of programs, such as slew rate, duty cycle, amplitude, pulse width, and pulse rate. Processor 40 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processor 40 herein may be embodied as software, firmware, hardware or any combination thereof.

Processor 40 also controls switching module 46 to apply the stimulation signals generated by stimulation generator 44 to selected combinations of electrodes 17. In particular, switching module 46 couples stimulation signals to selected conductors within lead 16 which, in turn, deliver the stimulation signals across selected electrodes 17. Switching module 46 may be a switch array, switch matrix, multiplexer, or any other type of switching module suitable to selectively couple stimulation energy to selected electrodes. Hence, stimulation generator 44 is coupled to electrodes 17 via switching module 46 and conductors within lead 16. In some examples, however, IMD 14 does not include switching module 46.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switching module 46 may be configured to deliver multiple channels on a time-interleaved basis. For example, switching module 46 may serve to time divide the output of stimulation generator 44 across different electrode combinations at different times to deliver multiple programs or channels of stimulation energy to patient 12.

Telemetry module 48 supports wireless communication between IMD 14 and an external programmer 20 or another computing device under the control of processor 40. Processor 40 of IMD 14 may receive, as updates to programs, values for various stimulation parameters such as amplitude and electrode combination, from programmer 20 via telemetry interface 48. The updates to the therapy programs may be stored within programs 52 portion of memory 42.

The various components of IMD 14 are coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

Figure 4:
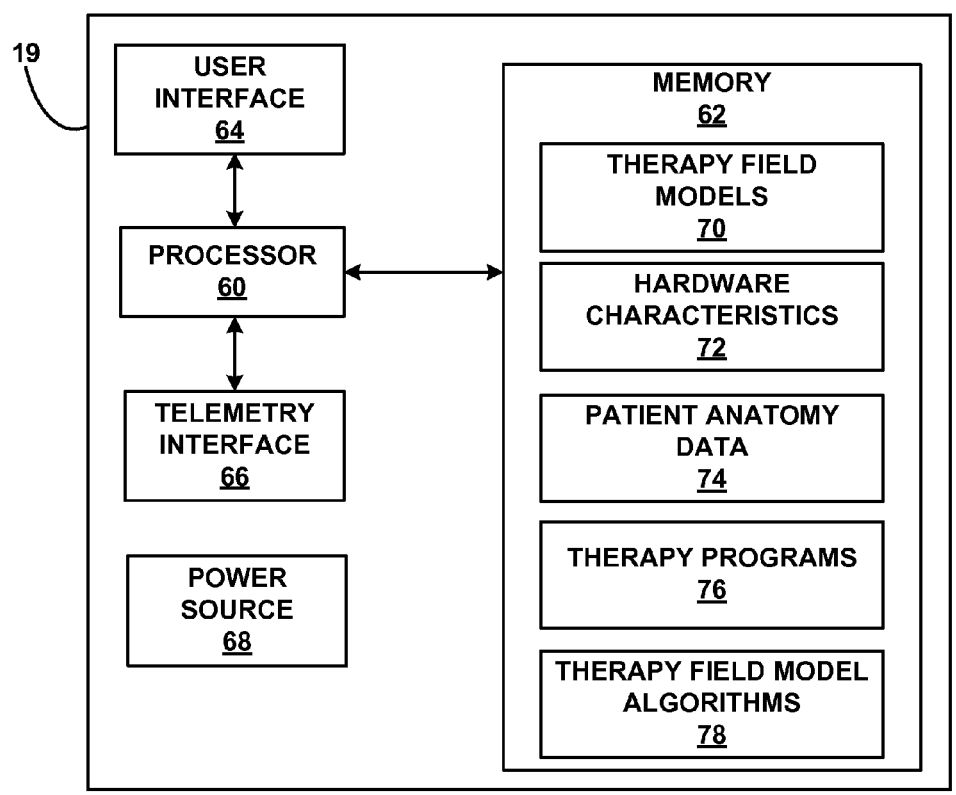
FIG. 4 is a functional block diagram of an example medical device programmer.

FIG. 4 is a functional block diagram of an example programmer 20. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming IMD 14. As shown in FIG. 4, external programmer 20 includes processor 60, memory 62, user interface 64, telemetry module 66, and power source 68. Memory 62 includes therapy field models 70, hardware characteristics 72, patient anatomy data 74, therapy programs 76, and therapy field model algorithms 78 in separate memories within memory 62 or separate areas within memory 62.

A clinician or another user may interact with programmer 20 to generate and/or select therapy programs for delivery in IMD 14. For example, in some examples, programmer 20 may allow a clinician to define stimulation fields and generate stimulation parameters for achieving the stimulation fields, which may be stored as therapy programs within therapy programs 76 portion of memory 62 or within IMD 14. Programmer 20 may be used to present anatomical regions to the user via user interface 64, select stimulation programs, generate new stimulation programs with stimulation fields, and transmit the new programs to IMD 14, as described in U.S. Pat. No. 7,822,483 to Stone et al. and entitled, "ELECTRICAL AND ACTIVATION FIELD MODELS FOR CONFIGURING STIMULATION THERAPY." Processor 60 may store stimulation parameters as one or more therapy programs in memory 62. Processor 60 may send programs to IMD 14 via telemetry module 66 to control stimulation automatically and/or as directed by the user.

Programmer 20 may be one of a clinician programmer or a patient programmer in some examples, i.e., the programmer may be configured for use depending on the intended user. A clinician programmer may include more functionality than the patient programmer. For example, a clinician programmer may include a more featured user interface, allowing a clinician to download usage and status information from IMD 14, and allowing a clinician to control aspects of IMD 14 not accessible by a patient programmer.

A user, e.g., a clinician or patient 12, may interact with processor 60 through user interface 64. User interface 64 may include a display, such as a liquid crystal display (LCD), light-emitting diode (LED) display, or other screen, to show information related to stimulation therapy, and buttons or a pad to provide input to programmer 20. In examples where user interface 64 requires a 3D environment, the user interface may support 3D environments such as a holographic display, a stereoscopic display, an autostereoscopic display, a head-mounted 3D display, or any other display that is capable of presenting a 3D image to the user. Buttons of user interface 64 may include an on/off switch, plus and minus buttons to zoom in or out or navigate through options, a select button to pick or store an input, and pointing device, i.e. a mouse, trackball or stylus. Other input devices may be a wheel to scroll through options or a touch pad to move a pointing device on the display. In some examples, the display may be a touch screen that enables the user to select options directly from the display screen.

Processor 60 processes instructions from memory 62 and may store user input received through user interface 64 into the memory when appropriate for the current therapy. In addition, processor 60 provides and supports any of the functionality described herein with respect to each example of user interface 64. Processor 60 may comprise any one or more of a microprocessor, DSP, ASIC, FPGA, or other digital logic circuitry, and the functions attributed to programmer 60 may be embodied as software, firmware, hardware or any combination thereof.

Memory 62 may include any one or more of a RAM, ROM, EEPROM, flash memory or the like. Memory 62 may include instructions for operating user interface 64, telemetry module 66 and managing power source 68. Memory 62 may store program instructions that, when executed by processor 60, cause the processor and programmer 20 to provide the functionality ascribed to them herein. Memory 62 also includes instructions for generating therapy programs, such as instructions for determining stimulation parameters for achieving a user-selected stimulation fields or instructions for determining a resulting stimulation field from user-selected stimulation parameters. Memory 62 may also include a removable memory portion that may be used to provide memory updates or increases in memory capacities. A removable memory may also allow patient data to be easily transferred to another computing device, or to be removed before programmer 20 is used to program therapy for another patient.

In addition, memory 62 stores algorithmic models of one or more therapy fields, i.e., therapy field models 70, which may include an algorithmic model of a baseline therapy field. The models of the therapy fields may be generated by processor 60 using an algorithm stored within therapy field model algorithm section 78 of memory 62. The one or more stored algorithms 78 may generate an algorithmic model of a baseline therapy field based on the stimulation parameters of therapy programs 76, the hardware characteristics of therapy system 10 stored within hardware characteristics 72 portion of memory 62, and patient anatomy data 74. The stored algorithm 78 may include, for example, electrical field model equations that define how the electrical field propagates away from an origin location.

As previously indicated, the hardware characteristics may include an energy threshold value of IMD 14 or one or more channels of IMD 14, the number of available channels for delivering stimulation signals to a target tissue site within patient 12, the size of the power source of IMD 14, the number or types of leads 16 implanted within patient 12, the number of electrodes 17, the spacing between adjacent electrodes 17, the size of each of the electrodes 17, the type of electrodes 17 (e.g., ring electrodes, partial-ring electrodes, segmented electrodes), and the like. In examples in which a therapy system includes two or more leads, such as therapy system 30 in FIG. 2, the hardware characteristics of the therapy system may include a baseline distance between the electrodes of the leads, i.e., the distance at the time of implant within patient 12. In addition, the patient anatomy data may include the anatomical structure of patient 12 and the characteristics of the tissue, such as the impedance, proximate to electrodes 17.

Programmer 20 may communicate wirelessly with IMD 14 or another device, such as using RF communication or proximal inductive interaction of programmer 20 with IMD 14. This wireless communication is possible through the use of telemetry module 66, which may be coupled to an internal antenna or an external antenna. Telemetry module 66 may include circuitry known in the art to support such wireless communication. An external antenna that is coupled to programmer 20 may correspond to the programming head that may be placed over the patient's skin near the implanted IMD 14.

Telemetry module 66 may also be configured to communicate with another computing device via wireless communication techniques, or direct communication through a wired connection. Accordingly, telemetry module 66 may include circuitry known in the art for such communication. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 20 without needing to establish a secure wireless connection.

Power source 68 delivers operating power to the components of programmer 20. Power source 68 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries (e.g., nickel cadmium or lithium ion batteries) may be used. In addition, programmer 20 may be directly coupled to an alternating current source, such would be the case with some computing devices, such as personal computers. Power source 68 may include circuitry to monitor power remaining within a battery. In this manner, user interface 64 may provide a current battery level indicator or low battery level indicator when the battery needs to be replaced or recharged. In some cases, power source 68 may be capable of estimating the remaining time of operation using the current battery.

During the course of therapy planning or during chronic therapy delivery, a first therapy program may be generated based on the hardware characteristics of therapy system 10, and therapy system 10 may be subsequently modified. For example, an additional lead may be added to therapy system 10 or IMD 14 may be replaced by another IMD. For example, IMD 14 may be replaced by another generation of IMD 14, IMD 14 may be a single channel electrical stimulator that is replaced by a multi-channel electrical stimulator, or IMD 14 may be replaced by an IMD that has a different energy threshold value or a power source having a different capacity, which may affect the range of available stimulation parameter values for respective IMDs. In other cases, therapy system 10 may not include IMD 14, but may include an external trial stimulator that is used to determine whether patient 12 is responsive to stimulation therapy and may be used to determine efficacious therapy programs for stimulation therapy, and therapy system 10 may be modified by replacing the external trial stimulator with an implantable medical device. Other modifications to a therapy system are contemplated.

As previously indicated, in some cases, therapy system 10 may be used to generate the algorithmic model of a baseline therapy field that is known to provide efficacious therapy to a class of patients with a common patient condition, which may be characterized by common patient symptoms or patient diagnoses. When a therapy program is generated for a specific patient in the class, the therapy system implanted within the specific patient may differ from therapy system 10. Accordingly, in some examples, the algorithmic model of the baseline therapy field may be useful for generating a second therapy program for the patient's particular therapy system.

In some cases, depending upon the type of modification that is made to therapy system 10, a first therapy program determined to provide efficacious therapy to patient 12 when the therapy is delivered by therapy system 10 may provide different therapeutic results when the modified therapy system delivers electrical stimulation to patient 12 with the therapy parameter values defined by the first therapy program. Accordingly, in order to substantially maintain the efficacy of therapy and help program the modified therapy system, a second therapy program for the modified therapy system may be generated to substantially maintain at least one field characteristic of the baseline therapy field. In the case of electrical stimulation therapy, the field characteristic may include, for example, a centroid of stimulation, an area of stimulation, recruited neurons, an amplitude of the voltage or current at a certain spatial point within stimulation area, a charge density, and the like.

The therapy programs for therapy system 10 and the modified therapy system may differ. For example, the medical devices of the first system and the modified therapy system may have different maximum energy outputs, which may affect the voltage or current amplitude or pulse width of a therapy program.

Figure 5A:
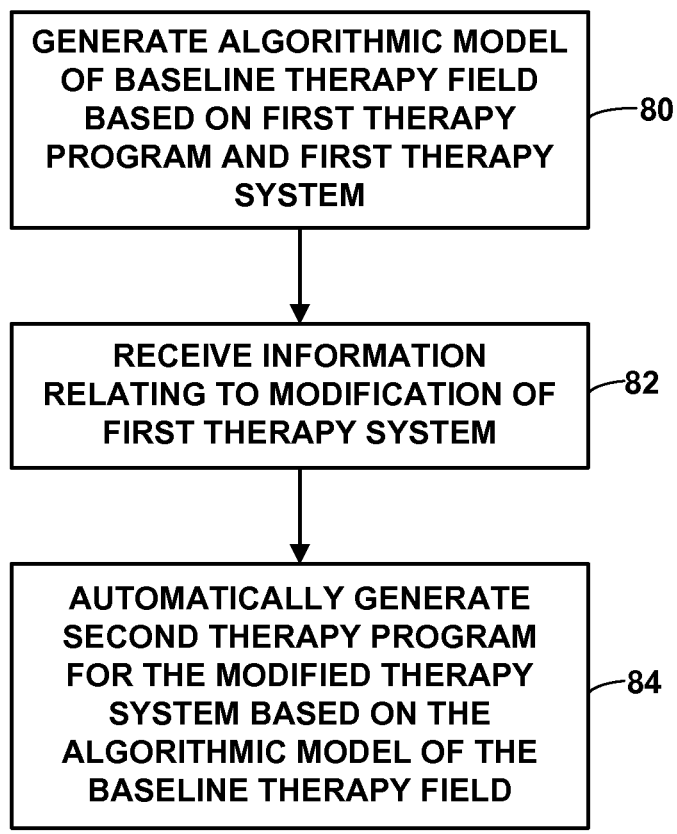
FIGS. 5A and 5B are flow diagrams illustrating example techniques for modifying a therapy program based on information indicative of a modification to a therapy system.

FIG. 5A is a flow diagram illustrating an example technique that processor 60 of programmer 20 or another computing device may implement in order to generate a second therapy program based on an algorithmic model of a baseline therapy field. The algorithmic model of the baseline therapy field may indicate the electrical field, activation field, voltage gradient or current density of electrical stimulation that balances effective therapy and minimal side effects.

Therapy system 10 delivers therapy to patient 12 based on a first therapy program. By referencing therapy field model algorithm 78 stored by memory 62 of programmer 20 (FIG. 4), processor 60 may generate an algorithmic model of a baseline therapy field (80). The algorithmic model of the baseline therapy field may be based on an anatomy of patient 12, a therapy program determined to provide efficacious therapy to patient 12 (herein referenced as a "first" therapy program), and the hardware characteristics of therapy system 10. An example of a technique for generating the algorithmic model of the second therapy field is described with respect to FIGS. 8-17.

Processor 60 may receive information relating to a modification to therapy system 10 (82). In some examples, a clinician or another user may provide information about modifications to therapy system 10 to programmer 20 by interacting with user interface 64. In examples in which IMD 14 is replaced by another medical device, the new medical device may communicate with programmer 20, e.g., by transmitting the energy threshold value for the new medical device, by transmitting an abstract model of the new medical device, or by transmitting the model number of the new medical device. The abstract model of the new medical device may include, for example, schematic hardware information for the medical device, such as the type of power source, therapy generation circuitry, and the like. Programmer 20 may store any relevant hardware data for different models of medical devices and, accordingly, the model number of the new medical device may be sufficient information to provide the hardware characteristics for the new medical device.

Processor 60 may store the change within hardware characteristics section 72 of memory 62 (FIG. 4). The modification to therapy system 10 may affect the therapy field that results from therapy delivery according to the first therapy program. Accordingly, processor 60 may automatically generate a second therapy program for the modified therapy system based on the algorithmic model of the baseline therapy field (84). The second therapy program may define stimulation parameter values that maintain efficacious stimulation therapy for patient 12, regardless of a modification to therapy system 10. For example, processor 60 may select the parameter values of the second therapy program to substantially maintain at least one field characteristic of the algorithmic model of the baseline therapy field. Examples of suitable techniques for generating the second therapy program are described below with reference to FIG. 5B.

Figure 5B:
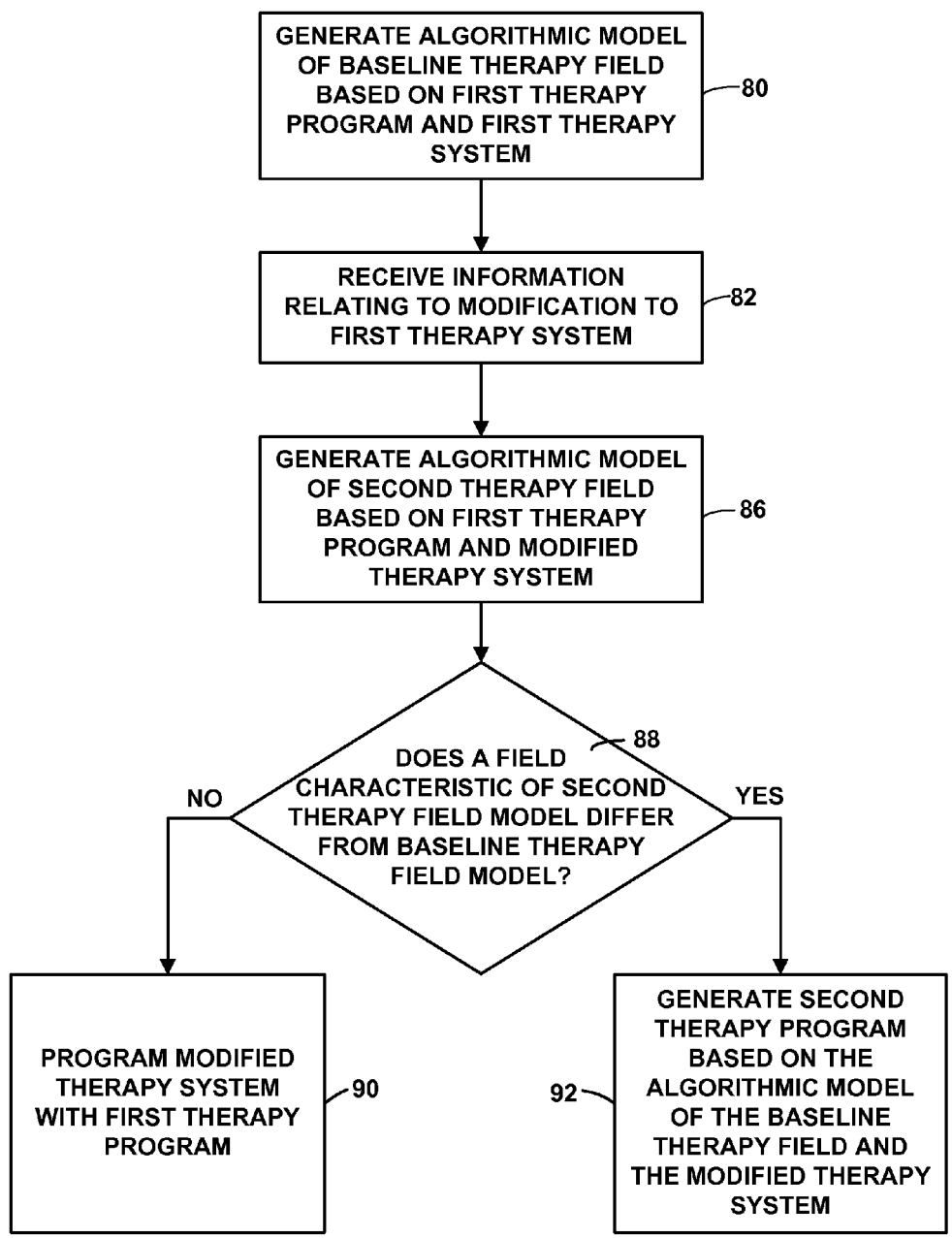

FIG. 5B is a flow diagram illustrating an example technique that processor 60 of programmer 20 or another computing device may employ in order to generate the second therapy program for a modified therapy system that substantially maintains at least one field characteristic of an algorithmic model of a baseline therapy field.

As in the technique shown in FIG. 5B, processor 60 generates an algorithmic model of a baseline therapy field resulting from therapy delivery according to a first therapy program by a first therapy system (80). Processor 60 may receive information relating to a modification to therapy system 10 (82). In order to determine whether to modify the first therapy program to compensate for any changes to the therapeutic effect from the hardware changes to therapy system 10, processor 60 generates an algorithmic model of a therapy field (a "second" therapy field) resulting from therapy delivery by the modified therapy system based on the first therapy program (86). The algorithmic model of the second therapy field may be generated using the same or a different algorithm used to generate the algorithmic model of the baseline therapy field, and the algorithm may be stored within algorithm section 78 of memory 62 (FIG. 4).

Processor 60 may compare a field characteristic of the second therapy field model to the corresponding field characteristic of the algorithmic model of the baseline therapy field (88). The one or more compared characteristics may be selected based on the characteristics of the therapy field that may affect the efficacy of therapy. In addition, the field characteristics may be weighted based on their impact on the efficacy of therapy, and the comparison between the algorithmic models of the second therapy field and the baseline therapy field may be made on the weighted characteristics.

For example, in the case of DBS delivered by therapy system 10 (FIG. 1), the regions of the patient anatomy recruited or otherwise covered by the therapy field may affect the efficacy of therapy more than the total area of the electrical field or activation field. Thus, processor 60 may compare the regions of patient anatomy recruited or otherwise covered by the algorithmic model of the second therapy field with the regions of patient anatomy recruited or otherwise covered by the algorithmic model of the baseline therapy field in order to determine whether the first therapy program should be modified. However, in some cases, processor 60 may compare both the regions of patient anatomy recruited by the algorithmic model of the second therapy field, as well as the total areas of the electrical field or activation field with the respective characteristics of the baseline therapy field model.

In the case of spinal cord stimulation delivered by therapy system 30 (FIG. 2), the centroid of stimulation may affect the efficacy of therapy more than the total area of the electrical field or activation field. Thus, in some examples, processor 60 compares the centroid of stimulation of the algorithmic model of the second therapy field with the centroid of stimulation of the algorithmic model of the baseline therapy field in order to determine whether the first therapy program should be modified. Again, processor 60 may compare more than one field characteristics of the second therapy field with the baseline therapy field, and, in some cases, may assign different weights to the different field characteristics.

The modification to therapy system 10 may not significantly affect the efficacy of therapy delivered to patient 12. Accordingly, if the selected field characteristic of the algorithmic model of the second therapy field does not significantly differ from the algorithmic model of the baseline therapy field model, processor 60 of programmer 20 may control therapy delivery by the modified therapy system with the first therapy program (90).

On the other hand, the modification to therapy system 10 may affect the efficacy of therapy delivered to patient 12 if the therapy is delivered based on the therapy parameters of the first therapy program. If the selected field characteristic of the algorithmic model of the second therapy field differs from the respective characteristic of the baseline therapy field model, processor 60 may generate a second therapy program or a plurality of therapy programs based on the algorithmic model of the baseline therapy field and the modified therapy system (92). The parameter values of the second therapy program or may be selected to substantially maintain the one or more selected field characteristics of the algorithmic model of the baseline therapy field in order to substantially maintain the known therapeutic effects associated with the baseline therapy field.

The threshold difference between the at least one characteristic of the current and baseline therapy field models that triggers a modification to the first therapy program may be set by a clinician. For example, in the case of a difference in an area of an electrical field, processor 60 of programmer 20 may modify the first therapy program upon determining that an area of the second electrical field model and an area of a baseline therapy field model differ by at least 10 percent (%). Alternatively, processor 60 may modify the first therapy program upon determining that an area of a second electrical field model is at least 10% smaller than an area of a baseline therapy field model.

With respect to the centroid of stimulation characteristic of a therapy field, processor 60 of programmer 20 may modify the first (or "current") therapy program upon determining that a centroid of the second therapy field model has shifted by at least about 0.5 mm to about 3 millimeters (mm) relative to a centroid of the baseline electrical field model. In the case of a comparison between the regions of patient anatomy recruited or otherwise covered by the current and baseline therapy fields, processor 60 may modify the first therapy program upon determining that the algorithmic model of the second therapy field indicates that key structures of brain 18 are no longer recruited, where the key structures of brain 18 may be the structures of brain 18 recruited by the algorithmic model of the baseline therapy field.

Prior to implementing the second therapy program (e.g., generated by modifying parameter values of the first therapy program), processor 60 may prompt patient 12 and/or a clinician to approve the change. Other thresholds for triggering a modification of the first therapy program are contemplated, and may differ based on the hardware characteristics of therapy system 10, the target tissue site for therapy delivery or the patient condition. Some patient conditions, such as neurological disorders, may be more affected by a shift in a centroid of stimulation or a change in electrical field area than other patient conditions, such as chronic pain managed by spinal cord stimulation.

Processor 60 may generate the second therapy program using any suitable technique. In one example, processor 60 selects another therapy program that may be stored in therapy programs section 76 of programmer memory 62, in memory 42 of IMD 14 or a memory of another device. For example, processor 60 may select another therapy program from a set of programs previously determined to provide efficacious therapy to patient 12 when delivered by the modified therapy system. In one example, the alternative therapy programs are associated with the modification to therapy system 10, e.g., within a look-up table or another data structure. For example, if the information indicative of the change to therapy system 10 indicates that IMD 14 was replaced by an IMD that has a lower energy threshold value, processor 60 may review energy values associated with the different therapy programs and select a second therapy program that has an energy value that is compatible with the lower energy threshold value.

In another example, processor 60 modifies the first therapy program by generating a new therapy program or modifying the value of at least one parameter of the first therapy program based on the modifications to therapy system 10. Processor 60 of programmer 20 may initiate a programming session with patient 12 after determining that at least one characteristic of a second therapy field model differs from the baseline therapy field model and reference a set of rules to generate a second therapy program. In one example, processor 60 implements a goal-seeking function, such as to generate a second therapy program that results in a therapy field with at least one field characteristic (e.g., an activation energy at a spatial point within the target tissue site of patient 12) that substantially matches the corresponding field characteristic of the algorithmic model of baseline therapy field.

In other examples, processor 60 of programmer 20 may generate a second therapy program (92) by selecting one or more volumetric stimulation templates that are stored within memory 62 of programmer 20 or another device, and creating a stimulation template set that best matches at least one field characteristic of the algorithmic model of the baseline therapy field. Each stimulation template is associated with a set of stimulation parameters that can be used to deliver stimulation therapy to a patient. An example technique for generating a second therapy program with the aid of one or more stimulation templates is described with reference to FIGS. 18A-22.

In another example, processor 60 implements a tree-based technique for modifying a current therapy program, where the tree-based technique is implemented with the goal of identifying or generating a therapy program that matches or substantially matches at least one field characteristic of the algorithmic model of the baseline therapy field. The type of field characteristic may be selected based to be a field characteristic that is determined has an affect the efficacy of therapy delivery. A therapeutic tree may include a plurality of levels that are each associated with a different therapy parameter. The tree may include nodes that are connected to nodes of adjacent levels. A clinician or patient may interact with processor 60 via user interface 64 in order to create a program path by moving through one node at each level of the tree according to efficacy feedback (which may include information regarding side effects) from patient 12 and/or one or more sensors that detect physiological parameters of patient 12.

Examples of tree-based techniques for modifying a therapy program or generating a new therapy program are described in commonly-assigned U.S. Pat. No. 7,801,619 issued on Sep. 21, 2010 to Gerber et al., entitled, "TREE-BASED ELECTRICAL STIMULATION PROGRAMMING FOR PAIN THERAPY," and filed on Apr. 30, 2007; commonly-assigned U.S. Pat. No. 7,706,889 issued on Apr. 27, 2010 to Gerber et al., entitled, "TREE-BASED ELECTRICAL STIMULATOR PROGRAMMING," and filed on Apr. 30, 2007; and commonly-assigned U.S. Pat. No. 7,715,920 issued on May 11, 2010 to Gerber et al., entitled, "TREE-BASED ELECTRICAL STIMULATOR PROGRAMMING," and filed on Apr. 28, 2006.

As described in U.S. Pat. No. 7,801,619 to Gerber et al., stimulation parameter types (e.g., electrode combination, voltage or current amplitude, pulse width, and frequency) may be arranged in a tree-like structure so that higher priority adjustments occur at higher levels of the tree and lower priority adjustments occur at lower levels of the tree. For example, the parameters may be prioritized so that parameters believed to have the largest impact on efficacy are placed in upper levels of the tree, while parameters having lesser impacts are placed in lower levels of the tree. In one example provided in U.S. Pat. No. 7,801,619 to Gerber et al., one level of the tree may contain nodes that represent adjustments to pulse rate, while another level of the tree contains nodes that represent adjustments to pulse width, and yet another level contains nodes that represent adjustments in voltage or current amplitude.

Processor 60 may generate an algorithmic model of a baseline therapy field that results from therapy delivery by the second therapy system according to the therapy parameter values defined by a selected node of the tree. If the selected node of the tree results in a therapy field that substantially matches at least one field characteristic of the algorithmic model of the baseline therapy field, the therapy parameter values associated with the selected node may be selected as the values for the second therapy program. If the algorithmic model of the therapy field based on the therapy parameter values associated with the selected node does not substantially match at least one field characteristic of the algorithmic model of the baseline therapy field, then programming proceeds to other nodes at the same level of the tree as the selected node. After selecting the nodes that indicate the therapy parameters that result in a therapy field that has a field characteristic that substantially matches the algorithmic model of the baseline therapy field, processor 60 may set the stimulation parameters defined by program path through the therapeutic tree as the second therapy program and control IMD 14 to deliver therapy in accordance with the second therapy program.

In another example, processor 60 implements a genetic algorithm-based technique for modifying a current therapy program (92), such as the one described in commonly-assigned U.S. Pat. No. 7,239,926 to Goetz et al., entitled, "SELECTION OF NEUROSTIMULATION PARAMETER CONFIGURATIONS USING GENETIC ALGORITHMS," which issued on Jul. 3, 2007. In one example described in U.S. Pat. No. 7,239,926 to Goetz et al., genetic algorithms provide guidance in the selection of stimulation parameters by suggesting the parameters that are most likely to be efficacious given the results of tests already performed during an evaluation session. Genetic algorithms encode potential solutions to a problem as members of a population of solutions. This population is then judged based on a fitness function. The best therapy programs are then retained and a new generation is created based upon their characteristics. The new generation is composed of solutions similar in nature to the best performers of the previous generation.

In accordance with the techniques described in U.S. Pat. No. 7,239,926 to Goetz et al., processor 60 may select a first electrode combination (i.e., the electrodes selected for therapy delivery and the polarities of the selected electrodes) for therapy delivery by IMD 14, generate an algorithmic model of a therapy field based on therapy delivery with the first electrode combination, and select a second electrode configuration for IMD 14 based on a comparison of at least one field characteristic of the therapy field based on therapy delivery with the first electrode combination with the algorithmic model of the baseline therapy field. The genetic algorithm may suggest cross-over between different solutions identified by the genetic algorithm or mutation of one or more solutions identified by the genetic algorithm, or random electrode changes.

After generating a second therapy program (92), processor 60 may determine whether the second therapy program is a suitable alternative by receiving feedback relating to the efficacy the second therapy program. The feedback may be received in the form of efficacy information (e.g., a numeric rating or an indication of the coverage of the therapeutic effects) from patient 12 via programmer 20 and/or sensors that sense one or more patient parameters that are indicative of an efficacy of therapy. For example, in the case of electrical stimulation for urinary or fecal incontinence therapy, the sensors may indicate the number of involuntary voiding events, as described in U.S. Pat. No. 7,715,920 to Gerber et al.

Alternatively, processor 60 may determine whether the second therapy program is suitable by generating an algorithmic model of a therapy field resulting from therapy delivery by the modified therapy system in accordance with the second therapy program, and comparing at least one field characteristic of the therapy field to the algorithmic model of the baseline therapy field. In order to generate the algorithmic model of the therapy field based on the second therapy program, processor 60 may implement an algorithm similar to that used by to generate the baseline algorithmic model.

Figure 6A:
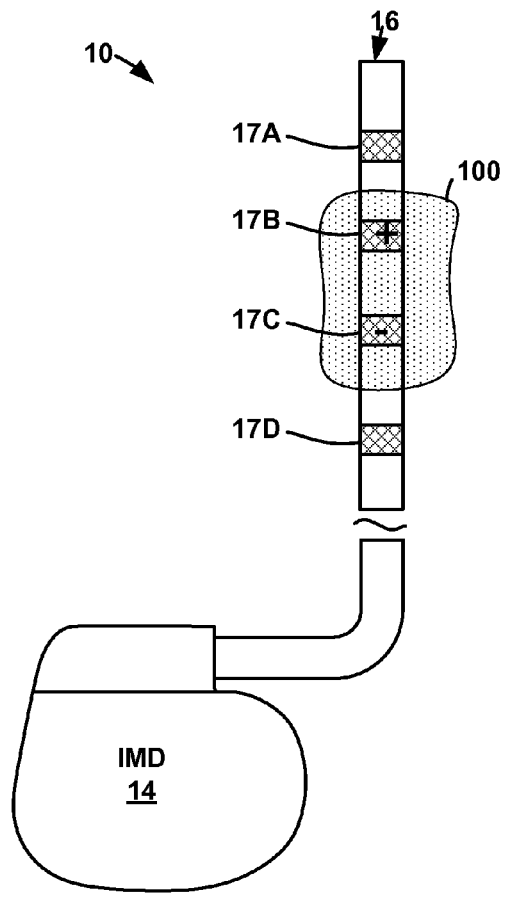
FIGS. 6A and 6B illustrate an example of a modification to the therapy system of FIG. 1.
Figure 6B:
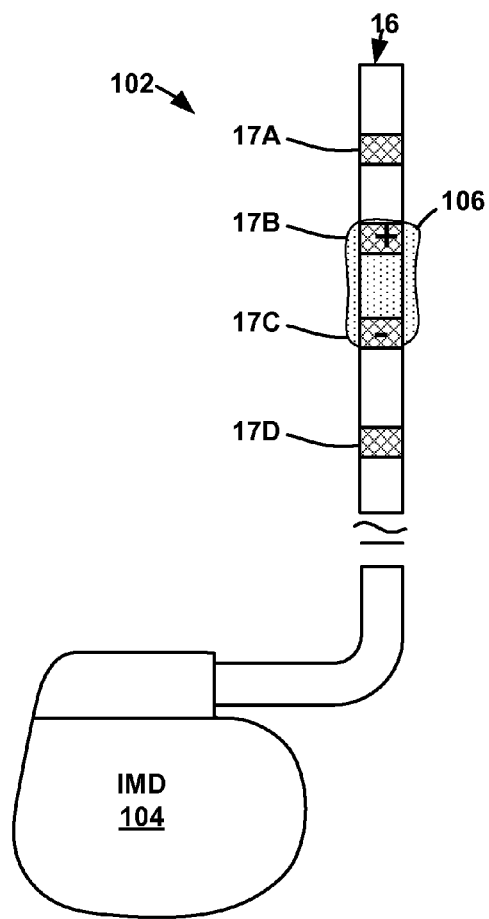

FIGS. 6A-6B illustrate an example of a modification to therapy system 10 and how a second therapy program may be generated based on an algorithmic model of a baseline therapy field known to provide efficacious therapy to patient 12. In the example shown in FIG. 6A, IMD 14 delivers electrical stimulation to a target tissue site according to a first therapy program that has been determined to provide efficacious therapy to patient 12. The first therapy program defines an electrode combination, i.e., selects electrodes 17B and 17C of lead 16 as active electrodes of the combination. In addition, the first therapy program defines the polarities of the active electrodes. In the example shown in FIG. 6A, electrode 17B is an anode and electrode 17C is a cathode of the electrode combination. The first therapy program also defines a voltage or current amplitude value, and, in the case of therapy delivery by electrical pulses, pulse width and pulse rate values for the stimulation signal defined by the first therapy program.

An algorithmic model of an electrical field 100 that results from delivery of electrical stimulation by IMD 14 and lead 16 according to the first therapy program is shown in FIG. 6A. Electrical field model 100 represents where electrical stimulation will propagate from lead 16 based upon the first therapy program and an anatomical data set associated with patient 12. The anatomical data set comprises at least one of an anatomical image of patient 12, a reference anatomical image, an anatomical atlas or a tissue conductivity data set. Processor 60 of programmer 20 may store electrical field model 100 as the algorithmic model of the baseline therapy field.

FIG. 6B is a schematic illustration of a modified therapy system 102. In some cases, such as if IMD 14 is a trial stimulation device used during the programming stage in order to determine whether patient 12 is responsive to stimulation therapy and to generate therapy programs that provide efficacious therapy to patient 12, IMD 14 may be replaced with another IMD 104, shown in FIG. 6B, for chronic therapy delivery. In addition to or instead of replacing IMD 14, therapy system 10 may be modified by replacing lead 16, e.g., if lead 16 becomes defective or if another generation of leads become available for use with the patient's therapy.

In the example shown in FIG. 6B, IMD 104 delivers a different signal waveform than IMD 14. If the first therapy program controls therapy delivery by IMD 104, therapy field 106 may result, which has a smaller cross-sectional area or volume than therapy field 100. The smaller therapy field 106 may be attributable to the different signal waveform provided by IMD 104. Thus, if therapy system 102 delivers stimulation to patient 12 according to the same therapy program implemented by therapy system 10 to achieve therapy field 100, the efficacy of the therapy may be adversely affected. In other examples, therapy systems 10, 102 may generate different sized therapy fields while being programmed with substantially similar therapy parameter values due to different leads. Some leads may have electrodes with a larger or more efficient tissue interface.

Processor 60 may generate a second therapy program using the techniques shown in FIGS. 5A-5B based on the hardware characteristics of the modified therapy system 102 and the algorithmic model of the baseline electrical field 100 known to provide efficacious therapy to patient 12. The second therapy program may include therapy parameter values that define stimulation signals having an energy at or below the energy threshold value of IMD 104, yet maintain at least one field characteristic as algorithmic model of baseline therapy field 100.

Other modifications to a therapy system are contemplated. For example, a clinician may "retrofit" an existing therapy system 10 including a single implanted lead 16 or two implanted leads 34, 36 by implanting one or two additional leads within patient 12 using a bifurcated lead extension that couples to a single connection port of IMD 14. As other examples, a clinician may replace one or more substantially cylindrical leads with one or more paddle leads, or replace one or more existing leads of any type with one or more different leads having a different physical or geometric arrangement of electrodes. A paddle lead may have a distal end defining a "paddle" shape, which includes one or more columns of electrodes.

Figure 7:
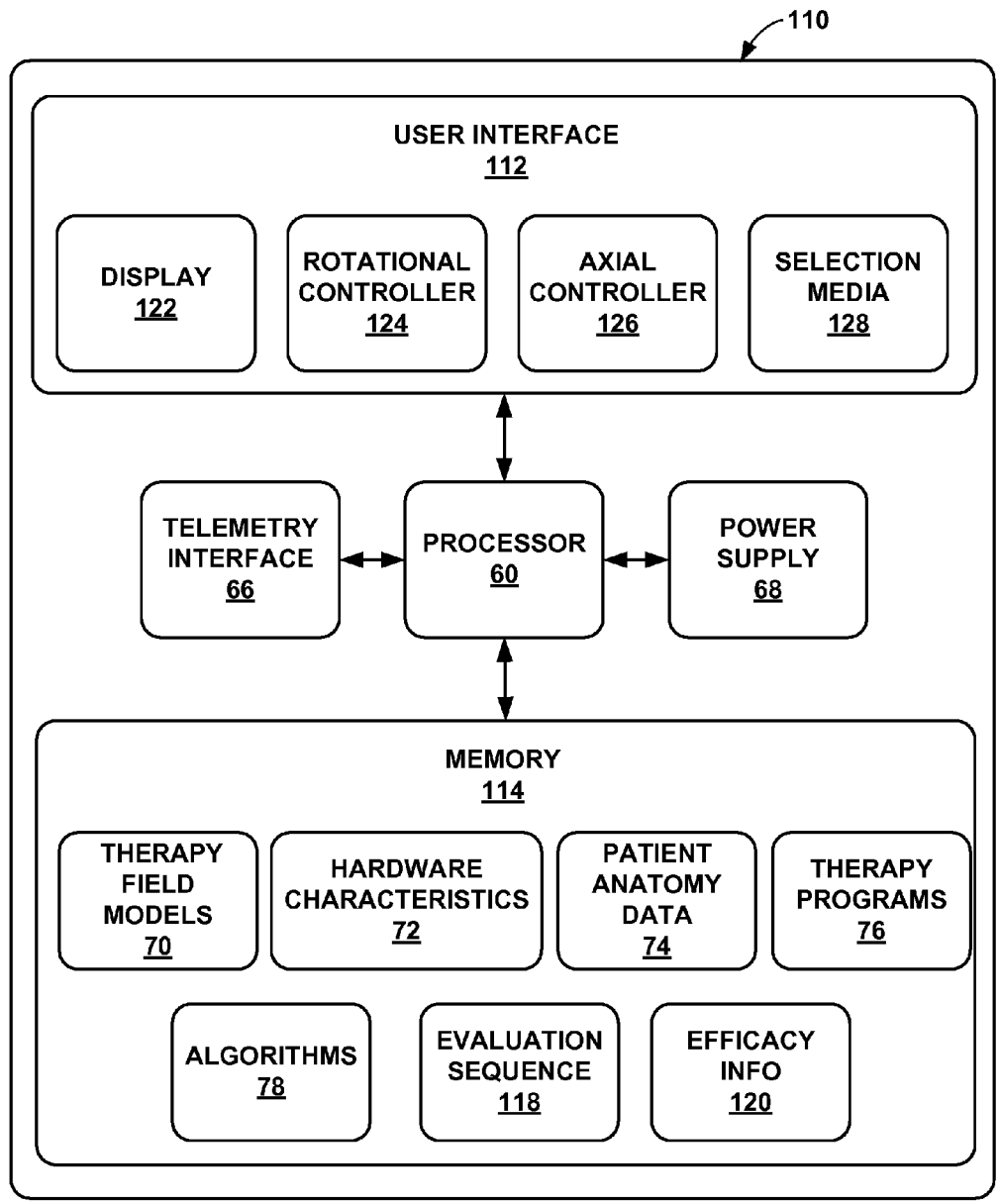
FIG. 7 is a block diagram illustrating an example programming device that may enable a clinician or another user to define an algorithmic model of a baseline therapy field.

FIG. 7 is a block diagram illustrating an example programming device 110 that presents a user interface to a clinician that enables the clinician to define an algorithmic model of a baseline therapy field, as well as generate a therapy program for a modified therapy system based on the algorithmic model of the baseline therapy field. The programming device 110 shown in FIG. 7 is an example of the programmer 20 of FIG. 1. An algorithmic model of the baseline therapy field may be defined by a clinician to target a particular anatomical structure or target tissue of patient 12 or may be defined to target a particular anatomical structure or target tissue for more than one patient, e.g., as a general therapy field that indicates a therapy field that may provide efficacious therapy for a particular patient condition. The programming device 110 shown in FIG. 7 is described in further detail in U.S. patent application Ser. No. 11/591,188 to Goetz et al.

Programming device 110 includes processor 60, telemetry interface 66, and power supply 68, which are described above with respect to FIG. 3. In addition, programming device 110 includes a user interface 112 and memory 114. Memory 114 may include any volatile, non-volatile, magnetic, optical, or electrical media, such as a RAM, ROM, NVRAM, EEPROM, flash memory or any other digital media. Memory 114 stores therapy programs 76 specifying electrode combinations, electrode polarities, and other stimulation parameters that may be transmitted to IMD 14. In addition to programs 76, memory 114 stores therapy field models 70, hardware characteristics 72 of therapy system 10, patient anatomy data 74, and algorithms 78 for generating algorithmic models of therapy fields. In addition, memory 114 may store an evaluation sequence 118 that guides the user in the selection of electrode combinations and stimulation parameters, or automatically selects electrode combinations and stimulation parameters for evaluation of efficacy. For example, evaluation sequence 118 may specify a predetermined progression of electrode combinations to be selected for evaluation, or provide rules for dynamic selection of electrode combinations during the course of evaluation.

In the example shown in FIG. 7, memory 114 also records efficacy information 120 associated with one or more of the stored programs 76. Specifically, upon selection of an electrode combination and stimulation parameters as a program, programming device 110 may direct IMD 14 to apply the program. Upon application of the program, the patient may provide feedback concerning efficacy. The user, which may be a clinician or the patient 12, then records the efficacy information in memory 114 of programming device 110. In this manner, different programs may be rated in terms of efficacy so that the user ultimately may select an effective electrode combination and stimulation parameters.

A user may interact with processor 60 via user interface 112 in order to generate an algorithmic model of a baseline therapy field, and identify efficacious electrode combinations and stimulation parameter values for stimulation therapy delivery by therapy system 10 and modified therapy system 102 (FIG. 6B). Processor 60 may provide display 122, e.g., a graphical user interface (GUI), via user interface 112 to facilitate interaction with the user. User interface 112 may also include one or more input media, such as lights, audible alerts, or tactile or other somatosensory alerts.

In the example shown in FIG. 7, the input media of user interface 112 includes rotational controller 124 and axial controller 126. Rotational controller 124 permits the user to move electrode combinations or stimulation fields around a representation of lead 16 presented on display 122 by selecting combinations of electrodes at different angular positions. Axial controller 126 permits a user to move electrode combinations or stimulation fields up or down along the length of lead 16 within the 2D or 3D modeling environment presented on display 122 by selecting different combinations of electrodes. In addition, axial controller 126 and rotational controller 124 may be configured to permit the user to view different electrodes, e.g., from multiple perspectives. User interface 112 also may present selection media 128 to permit the user to select particular electrode combinations for activation.

Using evaluation sequence 118, processor 60 may run a user-controlled test of a predetermined or dynamically generated sequence of electrode combinations to identify effective electrode combinations for alleviating symptom areas. Processor 60 may receive a pre-defined set of electrode combinations to test from a clinician and store the pre-defined set of electrode combinations as a set of programs, either alone or in combination with stimulation parameters. Alternatively, processor 60 may execute an electrode combination search algorithm according to evaluation sequence stored 118 in memory 114 to select individual electrodes or electrode combinations to test.

Processor 60 controls IMD 14 via telemetry interface 66 to test selected electrode combinations by controlling the stimulator to deliver electrical stimulation therapy to patient 12 via the selected electrode combinations. In particular, processor 60 transmits programming signals to IMD 14 via telemetry interface 66. As a sequence of electrode combinations proceeds, the programming signals may be transmitted at a rate consistent with the control input provided by a user. In this manner, the user relatively quickly observes the effects of each increment in the change between electrode combinations. In some cases, e.g., for DBS applications, effects of an electrode or parameter change may not be immediately evident. In such cases, a change may be activated and evaluated over a period of minutes, hours, or days before another change is initiated.

After completion of electrode testing, processor 60 may transmit one or more of the programs created by the clinician to IMD 14 via telemetry interface 66 for storage in IMD 14, or to another programmer used by patient 12 to control delivery of electrical stimulation therapy, e.g., via wireless or wired input/output interface. In either case, the selected electrode combinations can then be used to deliver therapy chronically or over an extended period of time.

Programming device 110 may be provided in the form of a handheld device, portable computer, or workstation that provides a user interface to a clinician or patient. The clinician or patient interacts with user interface 112 to program stimulation parameters for IMD 14 via external programming device 110. Hence, various aspects of user interface 112 described herein may be provided in the form of clinician programmer, a patient programmer or both.

During a programming session, a clinician or another user may select the stimulation parameter values of a therapy program that define the therapy delivered to patient 12 by therapy system 10 with the aid of the programming device 110. The clinician interacts with the user interface 112 to manually select and program particular electrodes of lead 16 via an electrode selection view, or select an electrode level of the lead and adjust a stimulation field resulting from a particular electrode selection. Once the clinician has defined the one or more stimulation fields, programming device 110 generates the stimulation parameter values associated with each of the defined stimulation fields. The stimulation parameter values may be transmitted to IMD 14 or stored within programs 76 section of the programmer's memory 114. Hence, user interface 112 of programming device 110 may permit a user to manually select electrode combinations and associated stimulation parameter values, or simply specify and manipulate a stimulation field in terms of size, direction and shape, in which case the programming device 110 or IMD 14 may automatically adjust electrode combinations and parameter values to approximate the desired stimulation field. In some examples, user interface 223 may restrict the ability of the user to define the stimulation fields based upon the stimulation capabilities of IMD 14 and lead 16. For example, the clinician may not make the stimulation field larger when the voltage or current amplitude cannot be increased any further, or when no more electrodes are available in the desired direction of the stimulation field.

Additionally, user interface 112 may restrict the user from applying the stimulation field to anatomical regions specifically banned from stimulation. These anatomical regions may severely alter the physiology of patient 12 and cause detrimental side effects or irreversible side effects. Accordingly, the user may manually lockout potentially unsafe electrodes or electrode levels based upon the actual implantation location of lead 16 within brain 18 or another target tissue site. Therefore, user interface 112 may be configured to prevent the user from selecting particular electrodes during the programming of stimulation parameters. Alternatively, or additionally, some electrodes or electrode levels may have predetermined parameter ranges that cannot be violated. For example, a minimum field value or parameter value may be specified to maintain field strength at a minimum level. Similarly, a maximum field value or parameter value may be specified to prevent stimulation in excess of a given level.

The stimulation field selected by a clinician during the programming of IMD 14 may be stored within therapy field models 70 section of memory 114 as an algorithmic model of a baseline therapy field. That is, user interface 112 may present a representation of one or more implanted leads and a representation of the patient anatomy proximate the implanted lead. The clinician may define a desired stimulation field over the representation of the patient anatomy, relative to a representation of implanted lead 16 or relative to both the representation of the patient anatomy and lead 16. The clinician-defined stimulation field may be the algorithmic model of the baseline therapy field that provides efficacious therapy to patient 12.

As previously indicated, processor 60 may generate a first therapy program for therapy system 10 that may achieve the user-defined stimulation field. Processor 60 may receive information relating to a modification to therapy system 10. As described with respect to FIG. 5B, an algorithmic model of a therapy field that results from therapy delivery by the modified therapy system 102 (FIG. 6B) may be compared to an algorithmic model of a baseline therapy field, i.e., the clinician-defined stimulation field, in order to determine whether a modification to the first therapy program is desirable, or whether the first therapy program acceptable for maintaining efficacious therapy.

Figure 8:
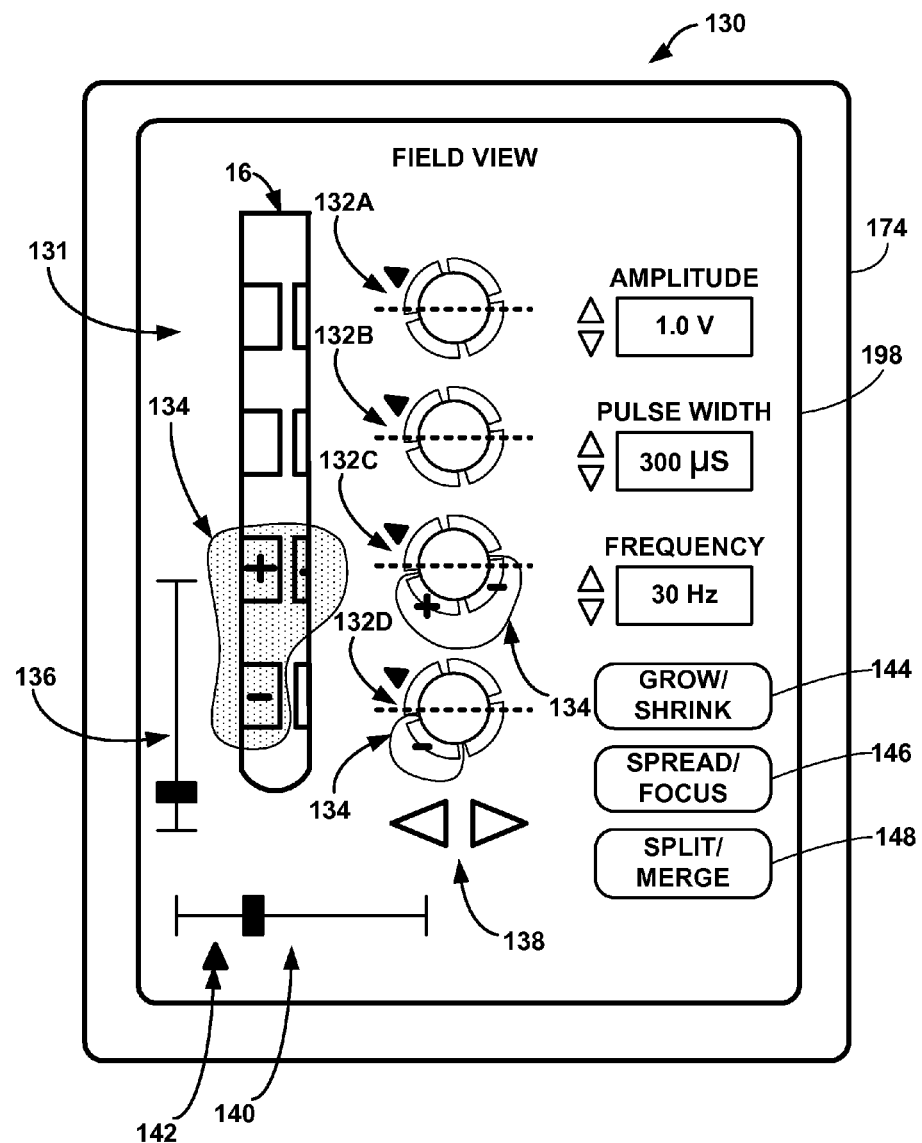
FIGS. 8-10 illustrate example graphic user interfaces (GUIs) that may be presented on a display of a programming device in order to aid the generation of efficacious therapy programs and algorithmic models of baseline therapy fields.

FIG. 8 illustrates a schematic representation of an example graphic user interface (GUI) 130 that may be presented on a display 122 of programming device 110 of FIG. 7. By interacting with GUI 130, a user may generate an algorithmic model of an electrical stimulation field produced by a selected electrode combination. For example, the user may change the size, shape or position of the field using graphical input media such as cursor or stylus control. In some examples, the user may be able to create a stimulation field in the field view and direct processor 60 of programming device 110 to generate stimulation parameters that would best generate the stimulation field. The generated electrical stimulation field may be stored as an algorithmic model of a baseline therapy field. In addition, the user may interact with GUI 130 to generate a second therapy program for modified therapy system 102 based on the algorithmic model of the baseline therapy field and the information regarding the hardware characteristics of the modified therapy system 102.

GUI 130 illustrates lead 16, which includes a complex electrode array geometry in the example shown in FIG. 8. A complex electrode array geometry generally refers to an arrangement of stimulation electrodes at multiple non-planar or non-coaxial positions, in contrast to simple electrode array geometries in which the electrodes share a common plane, a common axis or a common circumferential position. An example of a simple electrode array geometry is an array of ring electrodes distributed at different axial positions along the length of a lead. This type of electrode array geometry is shown in FIG. 3. Another example of a simple electrode array geometry is a planar array of electrodes on a paddle lead.

In the example of FIG. 8, rather than including four electrodes 17 as shown in FIG. 1A, lead 16 includes four electrode "levels" at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 16. Hence, lead 16 includes multiple electrical conductors, e.g., wires, cables or the like, that extend from the proximal end of the lead to respective electrodes to electrically couple the electrodes to electrical terminals associated with IMD 14.

Each electrode is positioned at a different angular position around the circumference of implantable lead 16, which has a generally circular cross-section in the example of FIG. 8. Each electrode is independently selectable so that stimulation energy can be delivered from the lead at different axial and angular positions. In some examples, lead 16 may include combinations of complex electrode array geometries and simple electrode array geometries. For example, ring electrodes that extend about the entire circumference of the lead may be used in combination with electrodes disposed at different axial and angular positions. Selective activation of the electrodes carried by lead 16 can produce customizable stimulation fields that may be directed to a particular side of lead 16 in order to isolate the stimulation field around a target anatomical region of brain 18.

GUI 130 illustrates a side view 131 and multiple cross-sectional views 132A-132D of lead 16 in alignment with corresponding electrode levels. In the example of FIG. 8, the user has selected an initial electrode combination, either manually or by selection for a set of electrode combinations provided by programming device 110, and the selected electrode combination is illustrated in GUI 130. GUI 130 presents a representation of a stimulation field 134 defined by the user and produced by the selected electrode combination, given stimulation parameter values selected by the user and general tissue characteristics stored within programming device 110.

The size and shape of stimulation field 134 may be established based on generic physical characteristics of human tissue and known physical characteristics of the electrodes of lead 16. In other words, stimulation field 134 displayed in field view 174 may only be an approximation of what the stimulation field would be in brain 18 of a specific patient 12. However, in some examples, physical characteristics of the actual anatomical structure of patient 12 being treated may be used to generate stimulation field 134. This anatomical structure information may be presented to programmer 110 in the form of patient anatomical data generated by an imaging modality, such as CT, MRI, or any other volumetric imaging system and stored within patient anatomy data section 74 of memory 114 (FIG. 7). In the example that uses the patient anatomical data, stimulation field 134 may be similar to an electrical field model, which is discussed in detail with reference to FIGS. 9 and 11. For example, stimulation field 134 may rely on tissue impedance models, field propagation models, and the like. In some examples, stimulation field 134 may be a representation of an electrical field, current density, voltage gradient, or neuron activation, applied to a generic human tissue or the anatomy of patient 12. In addition, the clinician may be able to switch between any of these representations when desired.

The user may move stimulation field 134 up or down relative to a longitudinal axis of lead 16 using vertical scroll bar 136 or some similar control interface. As stimulation field 134 moves up or down in response to the user input, programming device 110 automatically selects appropriate electrode combinations to support the vertical movement of stimulation field 134. For example, processor 60 may phase electrodes in and out as stimulation field 134 travels upward or downward, reducing the stimulation energy delivered from some electrodes as the stimulation field moves away from them, and increasing the stimulation energy delivered by other electrodes as the field moves toward them. Also, GUI 130 includes arrows 138 or similar input media that permit the user to transition between different electrode levels of the lead in cross-sectional views 132A-132D.

In addition, the user may rotate stimulation field 134 using horizontal scroll bar 140 or some similar control device. An arrow 142 may be provided next to horizontal scroll bar 140 to indicate the orientation of lead 16 relative to an anatomical structure. In addition, arrows may be provided in respective cross-section views 132A-132D to maintain orientation. As the user rotates stimulation field 134, processor 60 of programmer 110 may automatically select appropriate electrode combinations to support the rotational movement of the stimulation field 134. As in the case of vertical movement, rotational movement of stimulation field 134 may be accomplished by gradually reducing the stimulation energy delivered to some electrodes as the stimulation field rotates away from them, and gradually increasing the stimulation energy delivered to other electrodes as the stimulation field rotates toward them. Side view 131 and cross-sectional views 132A-132D permit the user to observe movement of stimulation field 134 from both an axial perspective and a rotational perspective.

Movement of stimulation field 134 using scroll bars 136, 140 or similar input media permits the user to evaluate different stimulation field positions without the need to manually select electrodes and manually enter parameter values. Instead, processor 60 of programming device 110 automatically selects electrodes and parameter values in response to movement of stimulation field 134 by the user. Although scroll bars 136, 140 are illustrated as examples of input media for movement of stimulation field 134, other types of input media may be used. Examples include up/down arrows or side-to-side arrows, which may be presented on a touch screen or formed by buttons or keys on programming device 110.

As a further alternative to manipulating the stimulation field 134, the user may select stimulation field 134 with a stylus, mouse, or other pointing device and drag the field upward, downward, or rotationally. In some examples, a mouse or other pointing device may support left or right click functionality to perform different operations relative to stimulation field 134. With a stylus, a first click on stimulation field 134 may initiate movement, dragging with the stylus directs movement relative to the schematic illustration of lead 16 in GUI 130, and a second click may terminate movement. In each case, processor 60 of programming device 110 responds to the specified movement by automatically adjusting the electrode combination and the stimulation parameters to approximate the characteristics of stimulation field 134 presented by GUI 130 on display 122 of programming device 110. As the stimulation parameter values change, the size and shape of stimulation field 134 presented on the display change. Similarly, as the electrode combination changes in terms of polarity or electrode selection, the size, shape or direction of stimulation field 134 presented on the display changes.

In other examples, processor 60 of programming device 110 may utilize stimulation templates and select the best fitting stimulation template set to a newly modified stimulation field 134. A stimulation template is a predetermined volumetric stimulation field that processor 60 of programming device 10 may substantially match to a desired stimulation field 134 from the clinician. An algorithm for generating a therapy field model that utilizes one or more stimulation templates to generate stimulation parameters that fit the user defined stimulation field may be less computationally intensive for processor 60 compared to an algorithm that references multiple equations or lookup tables to generate the stimulation parameters. The stimulation template may be a representation of an electrical field or other electrical stimulation related characteristic, e.g., current density, voltage gradient, or neuron activation, applied to a generic human tissue. For stored stimulation templates, processor 60 may adjust the current amplitude or voltage amplitude to alter the size of the stimulation template to cover the desired stimulation field 134 from the user. Examples of stimulation templates are described in U.S. patent application Ser. No. 11/591,188 to Goetz et al.

Processor 60 of programming device 110 may limit the rate of movement of stimulation field 134 within GUI 130. In other words, stimulation field 134 may only be moved a certain number of steps per second within GUI 130, or any other user interface that allows the clinician to drag the stimulation field. This rate movement limit may prevent unnecessary calculations or ensure patient comfort in real-time programming examples.

In addition to moving stimulation field 134, GUI 130 may permit the user to perform one or more operations that result in reconfiguration of the stimulation field. For example, the user may click on a border, i.e., an outer perimeter, of stimulation field 134, and drag it inward or outward to resize the stimulation field. Resizing by enlarging or shrinking stimulation field 134 in GUI 130 results in an increase or decrease in amplitude, pulse width or pulse rate of the stimulation energy. In some examples, enlarging or shrinking stimulation field 134 also may result in selection or de-selection of electrodes included in the existing electrode combination. In either case, processor 60 of programming device 110 adjusts the electrode combination and/or parameter values in response to the enlargement or shrinkage of stimulation field 134 by the user.

When a user clicks on stimulation field 134 border and drags it, the entire stimulation field may be expanded in two dimensions in equal proportions. Alternatively, stimulation field 134 may expand only in the direction in which the user drags the stimulation field. For example, horizontal dragging of the field perimeter to enlarge stimulation field 134 may result in overall enlargement of the stimulation field, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programming device 110 may provide different aspect ratio modes on a selective basis for expansion and shrinkage of stimulation field 134.

To enlarge or shrink stimulation field 134, the user may simply click on the stimulation field border. Alternatively, the user may click on a grow/shrink button 144 as shown in FIG. 8, and then click on the border of stimulation field 134 to drag it inward or outward and thereby adjust the cross-sectional size and/or volumetric of stimulation field 134. In response, processor 60 of programming device 110 may automatically reconfigure the electrode combination and/or stimulation parameter values to approximate the resized stimulation field. In this way, a user may generate an algorithmic model of a baseline therapy field by directly manipulating the stimulation field 134. Other field adjustment functions such as spread/focus button 146 and split/merge button 148 may be provided by GUI 130. In each case, the user changes stimulation field 134 by simply changing the representation of the stimulation field 134 presented on GUI 130, thereby avoiding the need to manually select electrodes and parameter values. The operation of the buttons 144, 146, and 148 is described in further detail in U.S. Patent Application Publication No. 2007/0203541 by Goetz et al.

After selecting a desirable stimulation field 134, processor 60 of programming device 110 may generate algorithmic models of an electrical field and an algorithmic model of an activation field. The model of the electrical field or the model of the activation field may be stored as the algorithmic model of a baseline stimulation field.

Figure 9:
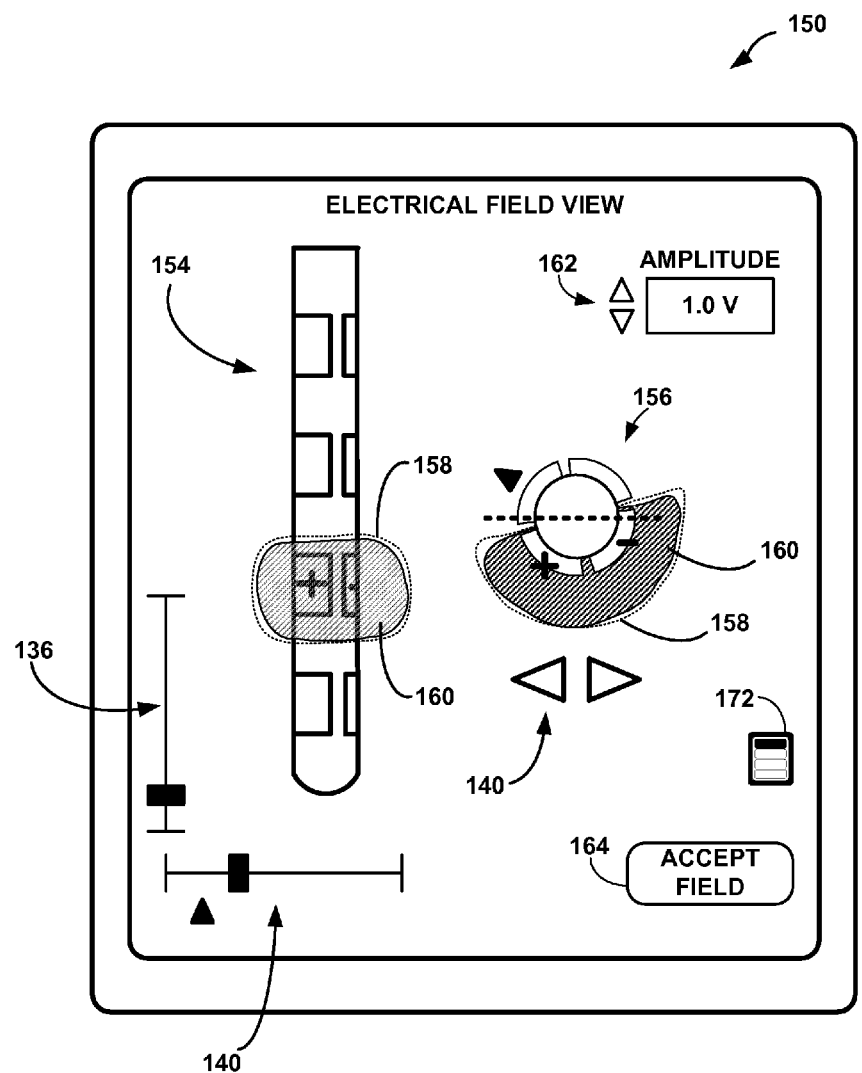
Figure 10:
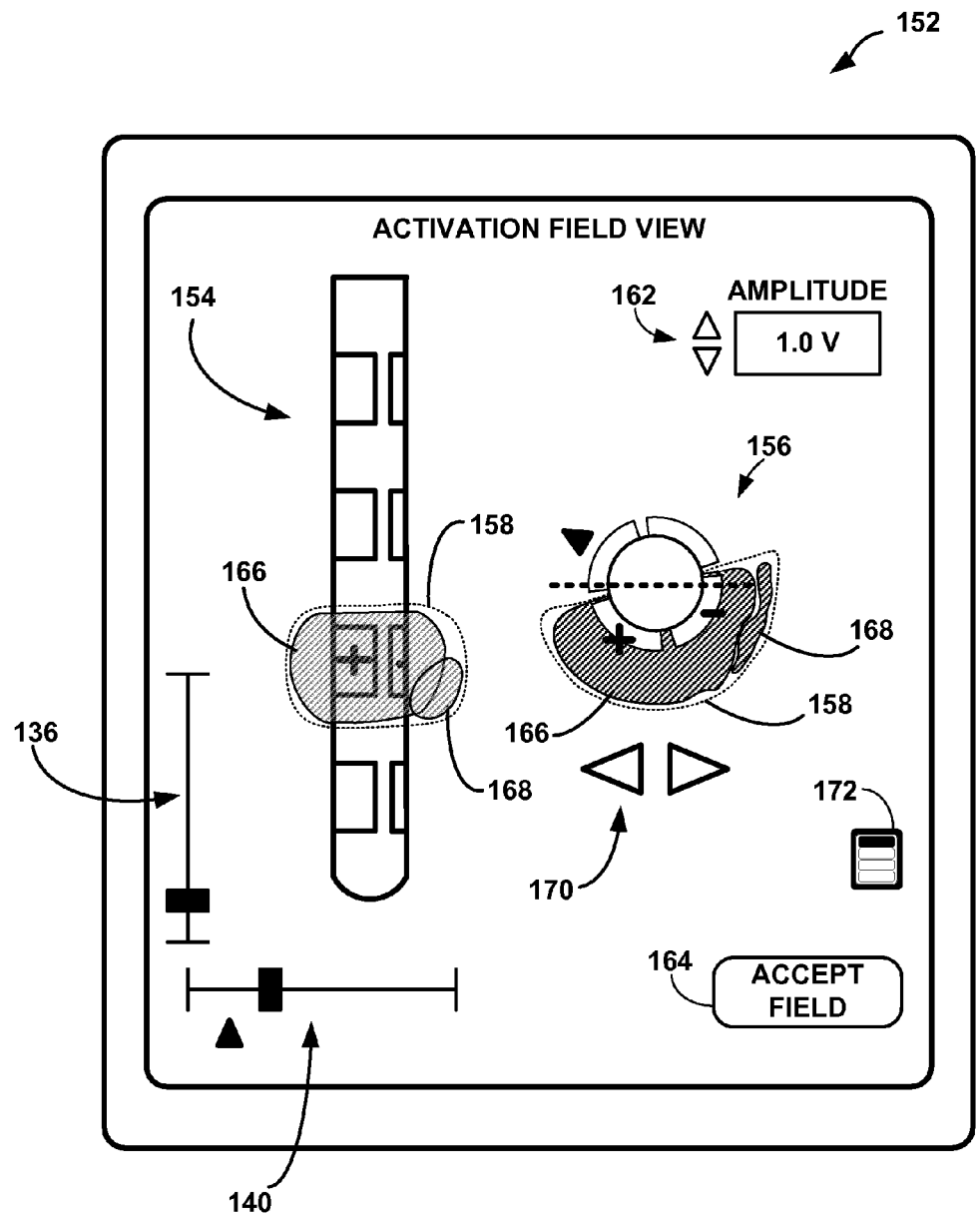

FIGS. 9 and 10 are schematic diagrams illustrating example GUIs 150, 152 that present electrical field models and activation field models, respectively, to a user. FIG. 9 illustrates an example GUI 150 that displays a stimulation field view to the user via display 122 of programming device 110. GUI 150 displays side view 154 and cross-sectional view 11=56 of implanted lead 16, and the user defines stimulation field 158 on the side and cross-sectional views, e.g., using the techniques described above with respect to FIGS. 7 and 8. Processor 60 of programming device 110 may generate stimulation parameters for therapy based on the selected stimulation field 158 and generate an electrical field model 160, which estimates an electrical field that results from therapy delivery according to the stimulation parameters associated with the selected stimulation field 158. In GUI 150, electrical field model 160 is displayed as an electrical field within the outer boundaries of stimulation field 158. In other examples electrical field model 160 may be a representation of another electrical stimulation related characteristic, e.g., current density, or voltage gradient. In addition, the clinician may be able to switch between any of these representations when desired.

Electrical field model 160 represents where the electrical current will propagate from the implanted lead 16 within tissue, as tissue variation within patient 12 may change the electrical current propagation from the lead in some directions. The variations in electrical field propagation may affect the ability of the therapy to actually treat a desired structure of brain 18 in examples in which IMD 14 delivers electrical stimulation to brain 18 (FIG. 1A) or cause a side-effect. The horizontal and axial views of electrical field model 160 illustrated in FIG. 9 are 2D slices of a volumetric electrical field model generated by processor 60 of programming device 110. Processor 60 utilizes an algorithm to generate electrical field model 160. In one example, the algorithm takes the patient anatomy data with electrical field model equations that define electrical current propagation into consideration. Accordingly, if the algorithmic model of the baseline therapy field includes electrical field 160, processor 60 may implement an algorithm that applies electrical field model equations that define how the electrical field propagates away from an origin location. The electrical field model equations may be specific to or customized for patient 12. The electrical field equations require the physical tissue characteristics of the tissue adjacent lead 16, which is included in the patient anatomy data set. From this information, processor 60 is able to generate the estimated electrical field 160 that will be produced in therapy.

Electrical field 160 may differ from the selected stimulation field 158 because processor 60 generates stimulation field 158 using an algorithm that only considers general tissue characteristics, which are not specific to patient 12. In other examples, the electrical field equations may utilize matrices or other mathematical models of the electrical field. In this manner, electrical field 160 can be estimated and modeled for the user. Accordingly, the user may be able to increase or decrease the amplitude of the stimulation parameters with an amplitude interface 162 in order to change the size and possibly shape of electrical field 160 or directly manipulate electrical field 160. If the user is satisfied with electrical field 160, the user may select accept field button 164 to transmit the stimulation parameters to IMD 14. If desired, the electrical field 160 or the stimulation field 158 may be stored as an algorithmic model of a baseline therapy field. For example, upon activation of accept field button 164, processor 60 may automatically store electrical field 160 or stimulation field 158 within therapy field models section 70 of memory 114 (FIG. 7).

FIG. 10 is similar to FIG. 9 and illustrates an example GUI 152 that displays an activation field view to the user via display 122 of programming device 110. From the defined stimulation field 158 on the side view 154 and cross-sectional view 156, processor 60 of programming device 110 may generate stimulation parameters for therapy and generates an activation field model based upon the electrical field model 160 of FIG. 9 and a neuron model that estimates which neurons within the electrical field model will be activated by the voltage of the electrical field during therapy. The neuron model may be a set of equations, a lookup table, or another type of model that defines threshold action potentials of particular neurons that make up the anatomical structure, as defined by the patient anatomy data, affected by the electrical field 160. If the voltage or current amplitude of the electrical field 160 is above the threshold of any neuron within the electrical field, that neuron will be activated, e.g., cause a nerve impulse. The activation field model is displayed as activation fields 166 and 168 within stimulation field 158.

Activation fields 166 and 168 of the activation field model indicate to the user where neurons around the lead will be activated from the stimulation therapy. Due to changes in electrical current propagation and voltage thresholds to activate a neuron, the activation of neurons may vary with the location of tissue around the lead. Some neurons may activate further from the lead with smaller voltages while other neurons may only be activated close to the lead because of a high voltage threshold. These differences in neurons may account for separate activation fields 166 and 168 within a contiguous stimulation field 158.

An area of activation fields 166, 168 (e.g., a tissue activation area) may be a field characteristic of the therapy field. The user may manipulate activation fields 166, 168. For example, the user may increase or decrease the size and/or shape of activation fields 166 and 168 by changing the amplitude with amplitude 162 or directly manipulate the activation fields (e.g., by modifying the borders of the displayed activation fields 166, 168) to automatically modify the stimulation parameters. Once the user is satisfied with activation fields 166, 168, the user may select accept field 164 to transmit the corresponding stimulation parameters to IMD 14. In both GUI 150 (FIG. 9) and GUI 152 (FIG. 10), the user may view cross-sections at other electrode levels with arrows 170. If desired, activation fields 166, 168 may be stored as an algorithmic model of a baseline therapy field. For example, upon activation of accept field button 164, processor 60 may automatically store activation fields 166, 168 within therapy field models section 70 of memory 114 (FIG. 7).

GUIs 150, 152 also include scroll bars 136, 140, which are described with respect to FIG. 8. In the example shown in FIGS. 9 and 10, GUIs 150, 152 also present field menu button 172 to the user, which may present further options to a user. For example, upon activate menu button 172, the GUI 150, 152 may display a menu that enables a user to select a modify stimulation field button to redefine the stimulation field 158, select polarity button to alter the polarity of any of the electrodes, a change field view button to switch between electrical or activation field views 150, 152, and a manual mode button which allows the user to manually select the stimulation parameters in an electrode view that displays the electrodes of the lead.

Although FIGS. 9 and 10 illustrate 2D views of lead 16, in other examples, a user interface may present a 3D view of lead 16 and the associated electrical field and activation fields may be displayed relative to the 3D views of lead 16.

Figure 11:
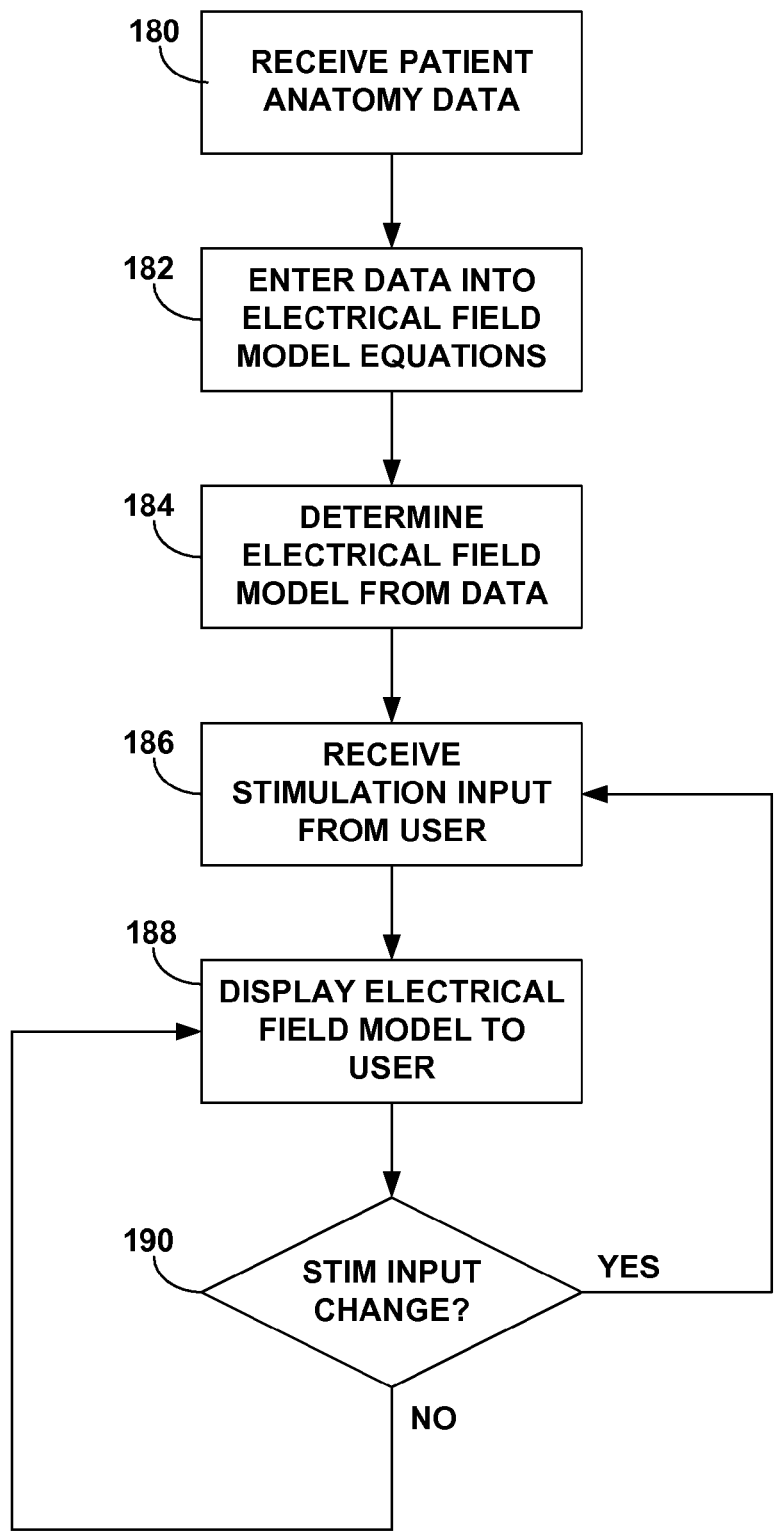
FIG. 11 is a flow diagram illustrating an example technique for calculating and displaying an electrical field model, which may be stored as an algorithmic model of a baseline therapy field.

FIG. 11 is a flow diagram illustrating an example technique for calculating and displaying electrical field model 160 (FIG. 9), which is based on a stimulation field 158. Stimulation field 158 may be determined based on input by a clinician and/or automatically generated by processor 60 of programming device 110 in response to stimulation parameters selected by the clinician. As shown in FIG. 11, processor 60 receives patient anatomy data necessary for creating an electrical field (180), which may include an anatomical image of the target tissue site of patient 12, a reference anatomical image, which may not be specific to patient 12, an anatomical atlas indicating specific structures of the patient's anatomy or a map of the tissue characteristics (e.g., conductivity or density) adjacent to lead 16. As previously described, the patient anatomy data may be created based on a medical imaging technique, such as, but not limited to, CT and MRI data. Processor 60 may store the patient anatomy data within section 74 of memory 114 (FIG. 7).

Processor 60 enters the patient anatomy data in stored electrical field model equations or equation sets to satisfy anatomical variable (182). Processor 60 may then determine the electrical field model from the data and equations (184). Once processor 60 receives stimulation input from a user defining the stimulation field, e.g., via user interface 112 (186), the electrical field may be displayed to the user via display 122 of user interface 112 (188). In some cases, processor 60 receives an indication change in the stimulation input from a user (190), and the modified electrical field model is presented to the user (188). The algorithmic model of the electrical field model displayed to the user (188) may be stored as an algorithmic model of a baseline therapy field within therapy field models section 70 of memory 114 (FIG. 7).

Figure 12:
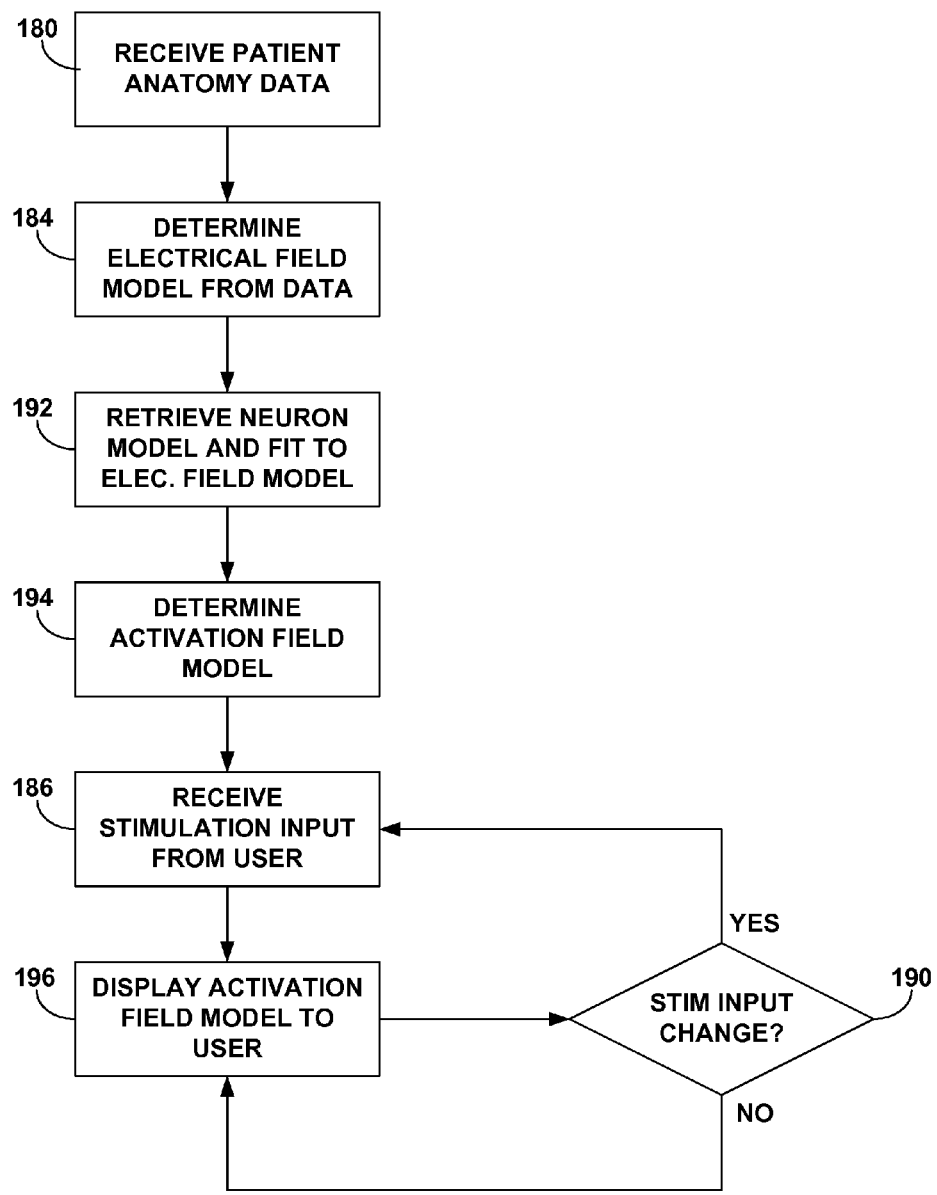
FIG. 12 is a flow diagram illustrating an example technique for calculating and displaying an activation field model, which may be stored as an algorithmic model of a baseline therapy field.

FIG. 12 is a flow diagram illustrating an example technique for determining and displaying the activation field model of defined stimulation. As shown in FIG. 12, processor 60 receives patient anatomy data indicative of the anatomy of patient 12 (180) and processor 60 determines the electrical field model from the patient anatomy data (184). Processor 60 retrieves a neuron model from memory 114 (FIG. 7) and fits the neuron model to the electrical field model (192). The neuron model may be stored within patient anatomy data section 74 of memory 114 (FIG. 7). Processor 60 may determine the activation field model based upon the electrical field model and neuron model (194).

In the example shown in FIG. 12, processor 60 receives stimulation input from a user defining the stimulation field, e.g., via user interface 112 (186). Processor 60 presents the resulting activation field model to the user via display 122 (196). If the clinician desires to change the stimulation input (190), user interface 112 receives stimulation input from the clinician modifying the previous stimulation input (186). In some cases, processor 60 may receive an indication change in the stimulation input from a user (190), and the modified electrical activation field model may be presented to the user (196). The algorithmic model of the activation field model displayed to the user (196) may be stored as an algorithmic model of a baseline therapy field within therapy field models section 70 of memory 114 (FIG. 7).

The techniques shown in FIGS. 11 and 12 may also be used to generate an algorithmic model of a therapy field that is based on therapy delivery by modified therapy system 102 (FIG. 6B) in accordance with the first therapy program (86) (FIG. 5B). In particular, as described with respect to FIG. 5B, in a technique for modifying a therapy program based on information indicative of a modification to therapy system 10, processor 60 of programmer 20 may generate an algorithmic model of a second therapy field to determine whether to modify a second therapy program. If the algorithmic model of the second therapy field is an electrical field model, processor 60 may receive patient anatomy data (180), enter the patient anatomy data and the modified therapy system data into electrical field model equations (182), and determine an algorithmic model of an electrical field that is based on modified therapy system 102 (FIG. 6B) and the first therapy program (184) (FIG. 11). If the algorithmic model of the modified therapy field is an activation field model, processor 60 may receive patient anatomy data (180), enter the patient anatomy data and the modified therapy system data into electrical field model equations (182), determine the electrical field model based on the equations (184), and retrieve a neuron model and fit it to the electrical field model (192) in order to determine an activation field model based on the modified therapy system 102 and the first therapy program (194) (FIG. 12).

Figure 13:
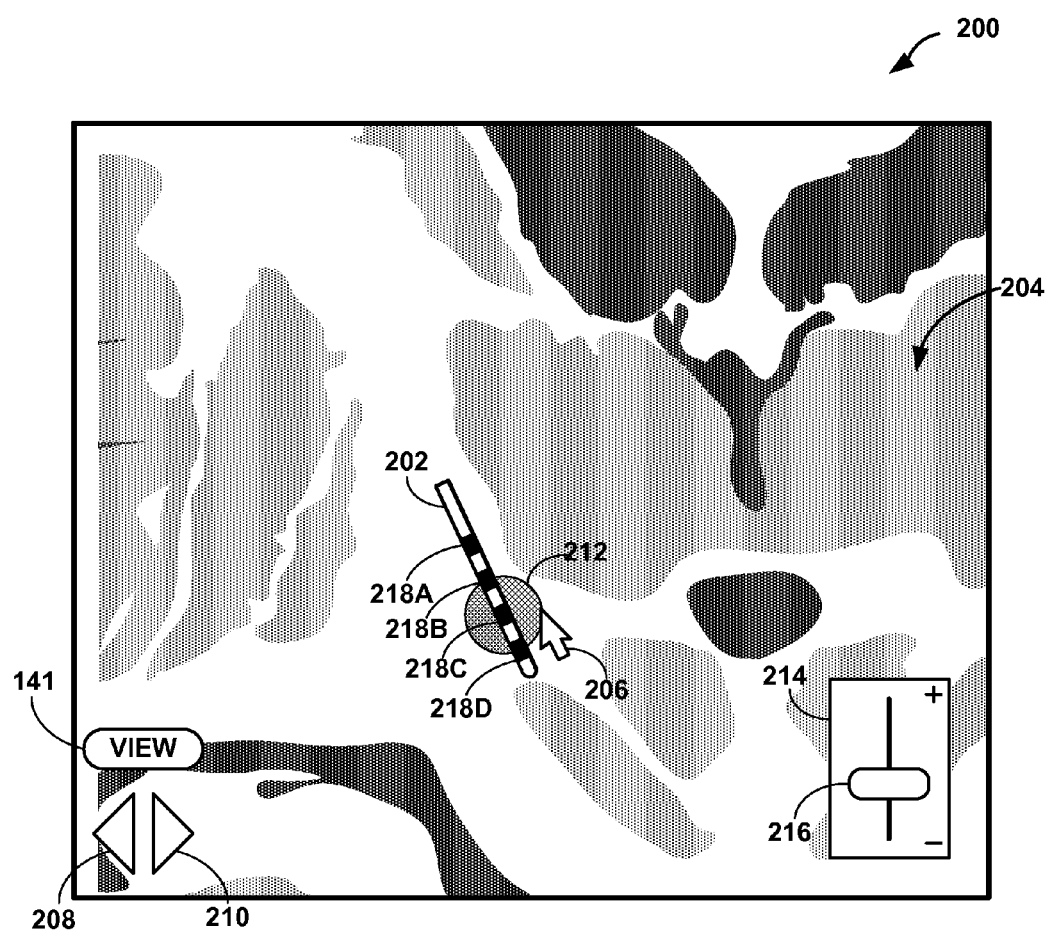
FIG. 13 illustrates an example GUI that may be presented on a display of a programming device.

An algorithmic model of a therapy field (e.g., a baseline therapy field or a second therapy field) may also be generated using other techniques. FIG. 13 is a schematic illustration of another example of GUI 200 that may be presented on display 122 of programming device 110 in order to help a user generate an algorithmic model of a baseline therapy field. A user may interact with GUI 200 via user interface 112 of programming device 110 in order to generate an electrical field model and/or an activation field model. GUI 200 presents a representation of anatomical regions of brain 18. In GUI 200, a lead icon 202 representing lead 16 is displayed to illustrate where lead 16 is actually implanted relative to one or more anatomical regions of brain 18 of patient 12. In particular, GUI 200 displays coronal view 204 of brain 18, which is a front-back vertical section of brain 18, which includes lead icon 202. Coronal view 204 may be an actual image of brain 18 produced with magnetic resonance imaging (MRI), computed tomography (CT), or another imaging modality. These images are used to produce the anatomical regions needed to help the clinician program the stimulation parameters.

Coronal view 204 is a 2D coronal slice of brain 18. Differently shaded portions of coronal view 204 indicate varying densities of tissue within brain 18. Darker portions indicate less dense tissue. For example, the darkest portion of coronal view 204 is indicative of spaces within brain 18 that contain cerebral spinal fluid (CSF). White portions of brain 18 indicate dense tissue and more neurons. The clinician may be able to recognize target anatomical regions by viewing coronal view 204. It should be noted that coronal view 204 shown in FIG. 13 is merely an example image, and actual images may include a wider range of shades and higher image resolution. Coronal view 204 provides a first perspective of the lead and the anatomical region in which the lead is implanted.

Coronal view 204 further includes pointer 206, previous arrow 208, next arrow 210, stimulation field 212, fine control input mechanism 214, and control slide 216. Pointer 206 may be controlled with a mouse and buttons, a track-ball, touchpad, touch screen or other movement input device, which may be a part of user interface 112 of programming device 110. A user may use pointer 206 to drag lead icon 202 into position or rotate lead icon 202 within coronal view 204 to correctly orient the lead icon according to the actual position of lead 16 within brain 18. The actual position of lead 16 within patient 12 may be determined with the aid of medical imaging techniques, such as MRI or CT. In other examples, the user may first select the type of lead 16 implanted within patient 12 and select the correctly scaled size of lead icon 202 to correspond with the anatomical regions of coronal view 204.

Programmer 110 may initially orient the user to the middle depth of the coronal view 204 or another depth that the programmer automatically selects based upon the type of therapy, implant location, or some other simple indication of location. However, the user may use arrows 208 and 210 to move to another coronal depth where lead 16 is implanted in brain 18. The clinician may zoom in to or out of coronal view 204 for a larger view of anatomical regions of the coronal view. In addition, the clinician may move coronal view 204 up, down, left, or right to view a larger or smaller portion of brain 18. While the clinician may manually position lead icon 202 within coronal view 204, processor 60 may automatically position lead icon 202 within GUI 200 based upon stereotactic data that is generated before lead 16 is implanted within patient 12. A stereotactic frame may be placed on a cranium of patient 12 to specifically locate areas of brain 18. In addition, this stereotactic information may be used to provide coordinates of the exact location of an implanted lead 16. In other examples, brain 18 may be imaged after implantation of lead 16 such that the lead is identifiable on coronal view 204. The user may point to and identify electrodes of lead 16 in the image to allow programming device 110 to reconstruct the correct position of the lead 16. In some cases, programming device 110 may automatically identify lead 16 and place lead icon 202 correctly within the anatomical region without any input from the user.

GUI 200 allows the user to select and adjust one or more stimulation fields 212, which is a cross-sectional view of volumetric stimulation field, which may be further defined in other orthogonal views. In order to define stimulation field 212 within coronal view 204, the user may user pointer 206 to select one of electrode levels 218A, 218B, 218C or 218D for stimulation field 212. As with the lead shown in FIGS. 9 and 10, an electrode level may have one or more electrodes around the circumference of lead icon 202, e.g., a complex electrode array geometry. All circumferential electrodes of the selected electrode level are initially activated for programming. In some cases, the user may attempt to place stimulation field 212 over the anatomical regions targeted for stimulation therapy while avoiding anatomical regions that may initiate unwanted side effects. In some examples, stimulation field 212 may be a representation of an electrical field, current density, voltage gradient, or neuron activation, applied to a generic human tissue or the anatomy of patient 12. In addition, the clinician may be able to switch between any of these representations when desired.

In the example shown in FIG. 13, the user selected electrode level 218C and stimulation field 212 shows the anatomical region that would be stimulated with therapy delivery via the selected electrode level 218C. The user may use pointer 206 to drag stimulation field 212 to define a smaller or larger stimulation field 212, which corresponds to a lower or higher voltage or current amplitude. For example, the user may click on a border, or perimeter of stimulation field 212 within GUI 200, and then drag the border to expand or contract the field 212. This adjustment is the coarse control of the size of stimulation field 212. The clinician may use pointer 206 to move control slide 216 up to slightly increase the size of stimulation field 212 within GUI 200 or down to slightly decrease the size of stimulation field 212. In some examples, the actual voltage or current amplitude associated with stimulation field 212 is displayed on coronal view 204 as stimulation field 212 changes characteristics.

Processor 60 of programming device 110 may limit the rate of movement of stimulation field 212 within GUI 200. In other words, stimulation field 212 may only be moved a certain number of steps per second within GUI 200, or any other user interface that allows the clinician to drag the stimulation field. This rate movement limit may prevent unnecessary calculations or ensure patient comfort in real-time changing of stimulation parameters with modifications of stimulation field 212.

The initial size of stimulation field 212 may be determined by a minimal threshold voltage previously determined to provide some efficacious results to patient 12. In other examples, the initial stimulation field size may be small to allow the clinician to safely increase the size of stimulation field 212. The size of stimulation field 212 may be limited by a volume parameter or a maximum voltage limit previously defined by the user or processor 60. The limit may be associated with capabilities of IMD 14 or safe voltage or current levels for patient 12. Once the size of stimulation field 212 is met, the clinician may no longer be able to drag the size of the stimulation field away from lead icon 202.

Stimulation field 212 may grow in size or split if the clinician selects more than one electrode level 218A-D. For example, the clinician may select electrode levels 218A and 218B to generate stimulation fields associated with each electrode level. The clinician may also move stimulation field 212 along the length of lead icon 202 and processor 60 may automatically select which electrode levels to activate to produce the stimulation field 212. The clinician may also move to other depths or slices of coronal view 204 with arrows 208 and 210. The other views may include, for example, a sagittal view of brain tissue, which may be taken from a perspective substantially perpendicular to the coronal view 204 or an axial view.

As described in further detail in U.S. patent application Ser. No. 11/591,299 to Stone et al., a programming device 110 may present a GUI including other views of brain 18 in addition to or instead of coronal view 204 in order to help select stimulation parameters for IMD 14. For example, programming device 110 may present a sagittal view of brain tissue or an axial view of brain tissue.

Figure 14:
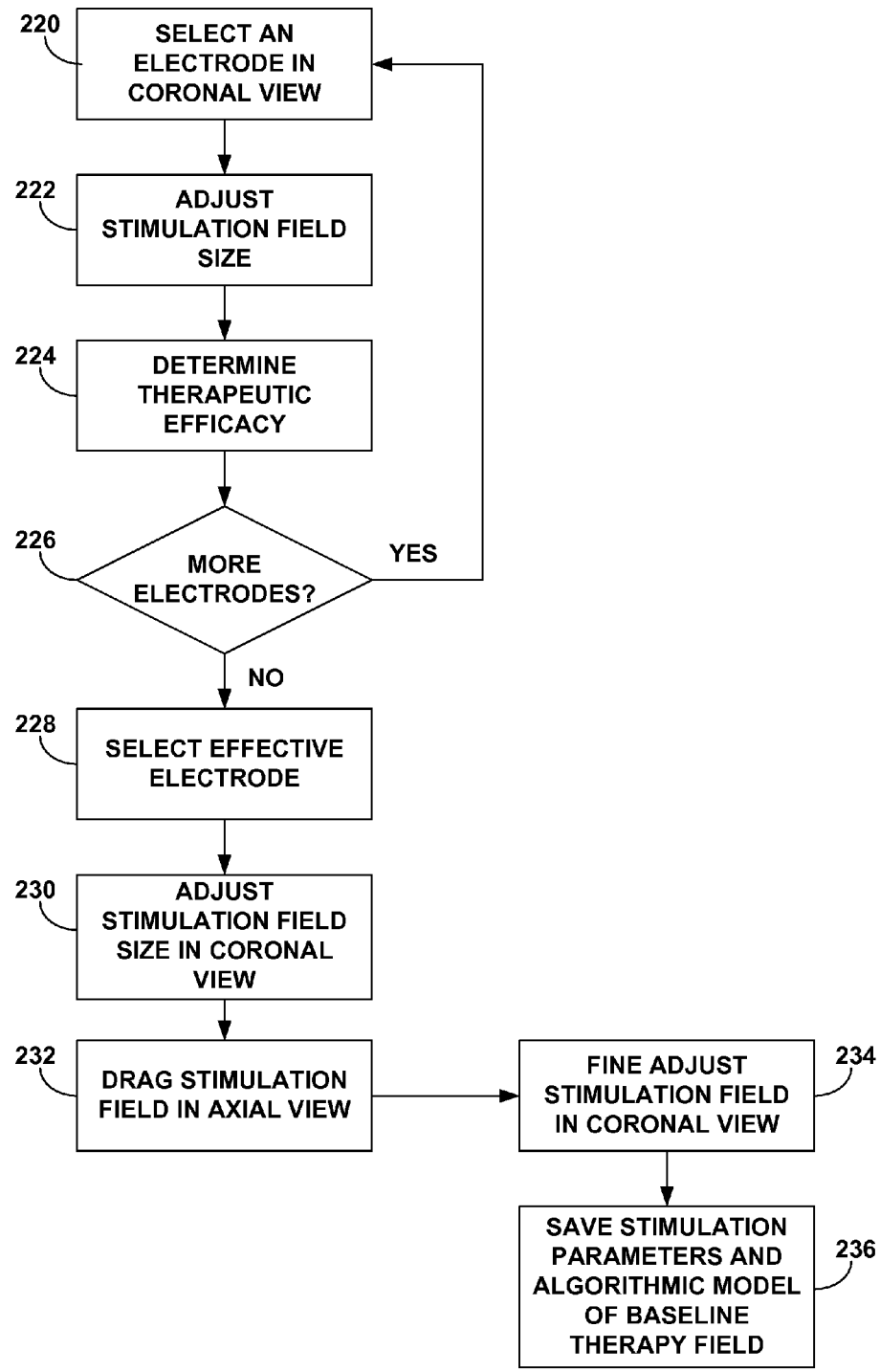
FIG. 14 is a flow diagram illustrating an example technique for adjusting a stimulation field for stimulation therapy in order to define stimulation parameters and generate an algorithmic model of a baseline therapy field.

FIG. 14 is a flow diagram illustrating an example technique for adjusting stimulation field 212 for stimulation therapy in order to define stimulation parameters for IMD 14 and to generate an algorithmic model of a baseline therapy field. As shown in FIG. 14, the clinician begins by selecting an electrode level 218A-218D in coronal view 204 of GUI 200 (FIG. 13), although other views, such as a sagittal view or axial view of brain 18 may also be used to select an electrode level 218A-218D (220). Processor 60 activates all the electrodes, i.e., electrodes at different angular positions around the lead circumference, in the selected electrode level. The user may interact with GUI 200 in order to adjust a size of stimulation field 212 (222) and test the stimulation field 212 on patient 12 to determine the therapeutic effect, if any (224). If the user wants to test stimulation delivered by more electrode levels (226), the user may repeat this process by selecting another electrode level and testing it on patient 12.

If there are no more electrode levels to test, the user may select the most effective electrode level from the tested electrodes (228) and adjust the size of stimulation field 212 by interacting with GUI 200 (230). The user may drag stimulation field 212 within GUI 200 in order to define a field 212 that minimizes side effects and improves therapeutic benefits to patient 12 (232). In addition, the user may use fine adjustment buttons 214 and 216 to further adjust stimulation field 212 (234). Additionally, the clinician may use a wand tool to select a range of pixel shades to quickly select anatomical regions that will be included in stimulation field 212.

In some examples, the user may adjust the simulation field in any of sagittal, coronal, or axial field views as desired by the clinician. In other examples, GUI 200 may require that the clinician enters each of the sagittal, coronal, and axial field views at least once before adjustment of the stimulation can be completed. Once stimulation field 212 is adjusted to produce effective therapy for patient 12, the user may save the electrode configuration and other stimulation parameters that achieve the stimulation field 212 as a stimulation program within memory 114 (FIG. 7) (236). The stimulation field 212 may also be stored as an algorithmic model of a baseline therapy field (236). Processor 60 may control the transmission of the therapy program to IMD 14 via telemetry device 66 (FIG. 7). In some examples, the user may repeat the programming procedure with GUI 200 to generate multiple stimulation programs and respective algorithmic models of baseline therapy fields. The clinician may also reprogram the therapy at any time with the aid of GUI 200 and generate an algorithmic model of a baseline stimulation field based on the reprogrammed therapy program.

Processor 60 of programming device 110 may use information received via user interface 112 to automatically generate stimulation parameters for the first therapy program according to the stimulation field 212 defined by the user. Processor 60 determines the dimensions of the stimulation field 212 to create a 3D vector field identifying the distances from lead 16 that stimulation may reach. Processor 60 may utilize the 3D vector field with an equation approximating electrical current propagation within brain tissue. The resulting data determines the electrode combination, voltage and current amplitudes, pulse rates, and pulse widths needed for reproducing the stimulation field within patient 12. In other examples, processor 60 of programmer 110 interprets density of tissue in the imaging data to more precisely approximate the stimulation parameters.

In some examples, processor 60 may utilize one or more stimulation templates stored within memory 114 in order to generate the stimulation parameters for achieving the stimulation field 212 defined by the user. As previously described, a stimulation template may be a predetermined volumetric stimulation field that processor 60 may match to a desired stimulation field 212. Each stimulation template may be based upon any one or combination of modeled data, experimental data, or analytical calculations prior to being stored in programming device 114. Stimulation templates are described in further detail in U.S. patent application Ser. No. 11/891,299 to Stone et al.

In other examples, a user may generate an algorithmic model of a stimulation field 212 without the aid of a lead icon 202. For example, when presented with the coronal view of the brain, as shown in FIG. 13, the user may create an outline defining the outer edges of stimulation field 212. By defining an algorithmic model of stimulation field 212 by outlining the desired field within GUI 200, the user outlining desired areas includes allowing the user to focus on the anatomy and physiology of patient 12 instead of manipulating an implanted device. Consequently, automatically generating stimulation parameters according to a user-selected stimulation area may increase therapy efficacy and decrease programming time.

In addition, in other examples, a user may select stimulation parameters and generate an algorithmic model of a baseline therapy field that indicates the field that provides efficacious therapy to patient 12 with the aid of an atlas of an anatomical region of patient 12. The atlas may be represented in the form of a drawing or actual image from an imaging modality such as MRI, CT, or other medical imaging techniques. The reference anatomy may be an anatomy different from patient 12 anatomy. Specific structures of the reference anatomy may be identified and their locations within the reference anatomy determined to create an atlas. The atlas may be stored in memory 114 of programming device 110. While an atlas may differ from the actual patient anatomy, the structure locations may be close enough to provide guidance to a user to generate stimulation parameters based upon the atlas.

In addition, in some examples, the user may generate an algorithmic model of a baseline therapy field with the aid of a user interface that presents, at the same time, an atlas and the actual anatomy of patient 12, e.g., generated by a suitable medical imaging technique. The atlas of the reference anatomy and the patient-specific anatomy may be combined to create a morphed atlas for programming the stimulation therapy. One example of how programming device 110 may create a morphed atlas is described in U.S. Patent Application No. 2005/0070781 by Dawant et al., entitled, "ELECTROPHYSIOLOGICAL ATLAS AND APPLICATIONS OF SAME" and filed Jul. 1, 2004.

Examples of systems and techniques for selecting therapy parameters and generating a resulting stimulation field with the aid of an atlas is described in further detail in U.S. Pat. No. 7,822,483 to Stone et al. In one technique described by U.S. Pat. No. 7,822,483 to Stone et al., a user may use a pointer to select a specific structure of the atlas presented on a user interface of a programming device, and the name of the structure may be is displayed. The programming device may generate stimulation parameters based upon the location of the one or more selected structures to the location of the implanted lead. In some examples described by U.S. Pat. No. 7,822,483 to Stone et al., generating stimulation parameters may include selection of stimulation templates and creation of a stimulation template set based on the selected structures. An atlas may allow a clinician to quickly select the most appropriate structure that needs to be stimulated to treat the condition of patient.

Figure 15:
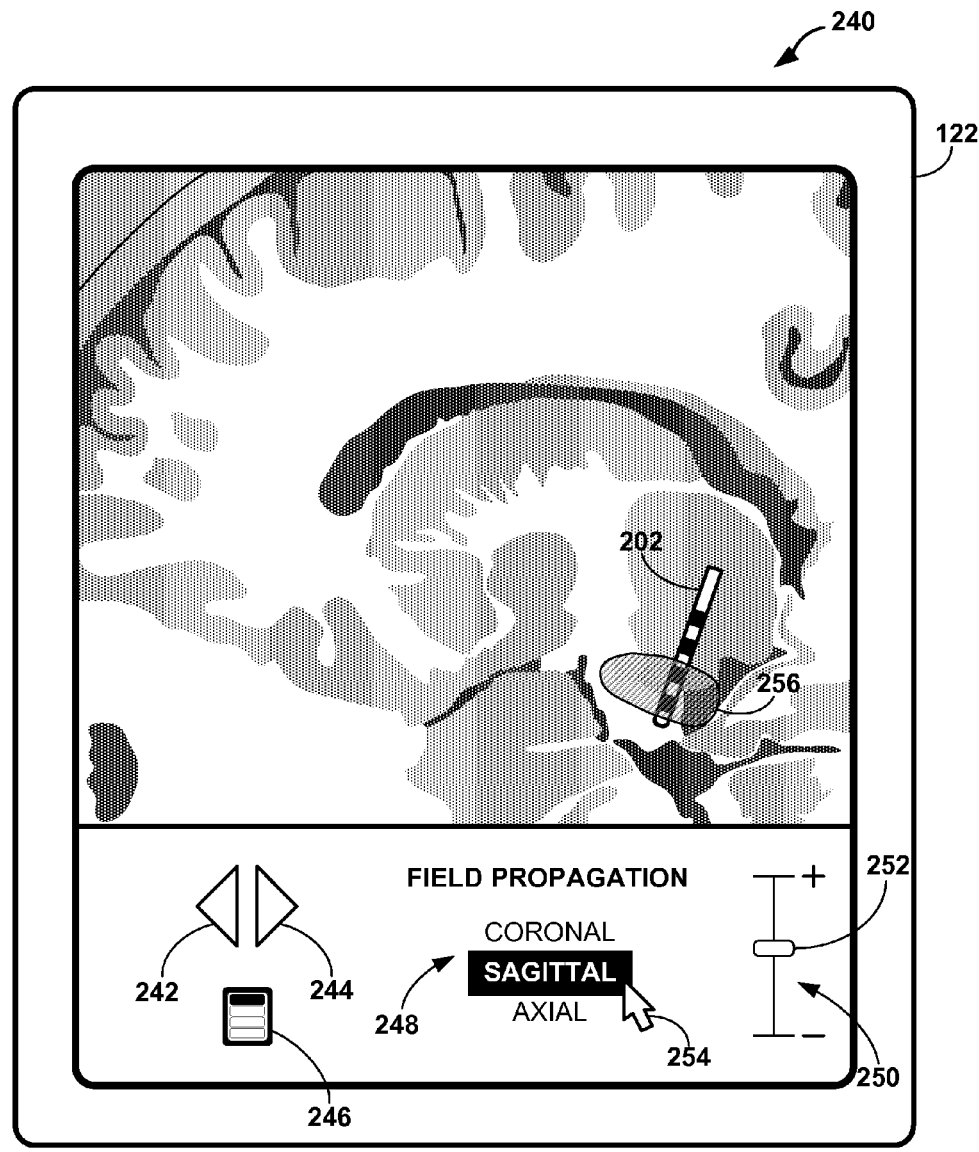
FIG. 15 illustrates an example GUI that may be presented on a display of a programming device.

Just as with GUIs 150, 152, an electrical field model or an activation field model may be generated based on a selected stimulation field 212 (FIG. 13). The electrical field model may approximate actual stimulation effects from therapy. FIG. 15 is an example screen shot of a GUI 240 that presents a sagittal view of a patient anatomy with an algorithmic model of an electrical field 256 of the defined stimulation therapy. Processor 60 may control the display of GUI 240 on display 122 (FIG. 7). The sagittal view of the patient anatomy may be a 2D view of any one of an atlas, a morphed atlas, or a patient anatomical region. GUI 240 also includes previous arrow 242, next arrow 244, menu 246, view indicator 248, and amplitude adjuster 250 with slider 252. In the example shown in FIG. 15, the clinician interacts with GUI using pointer 254, which may be similar to pointer 206 (FIG. 13).

Processor 60 of programming device 110 controls GUI 240 to display lead icon 202 and electrical field 256 to present an illustration to the clinician of what the electrical field of the stimulation therapy would look like according to the stimulation parameters defined by the clinician using any of the programming techniques described herein. Electrical field 256 is an algorithmic model that represents where the electrical current will propagate from lead 16 within brain 18, as tissue variation within brain 18 may change the electrical current propagation from the lead. The variations in electrical field propagation may affect the ability of the therapy to actually treat a desired structure or likelihood that the therapy may cause a side-effect.

Electrical field 256 is a 2D slice of the volumetric electrical field model created by programming device 110. Processor 60 utilizes the patient anatomical region data with electrical field model equations that define current propagation. Accordingly, electrical field 256 is an algorithmic model of an electrical field that indicates where stimulation will propagate from an implanted lead (represented within GUI 240 by lead icon 202). The clinician may interact with GUI 240 to increase or decrease the amplitude of the stimulation parameters with slider 252 and view how the amplitude change would affect the size and shape of electrical field 256. Slider 252 is an analog adjustment mechanism and may also be in the form of an adjustment knob instead of the slider. The user may move to different depths of the sagittal view with previous arrow 242 or next arrow 244 while adjusting the amplitude of electrical field 256 with slider 252. In some examples, GUI 240 may allow the user to redefine the stimulation field and generate new stimulation parameters if it is believed that electrical field 256 is unacceptable for therapy. An algorithmic model of electrical field 256 may be generated using a technique similar to that shown in FIG. 11.

Figure 16:
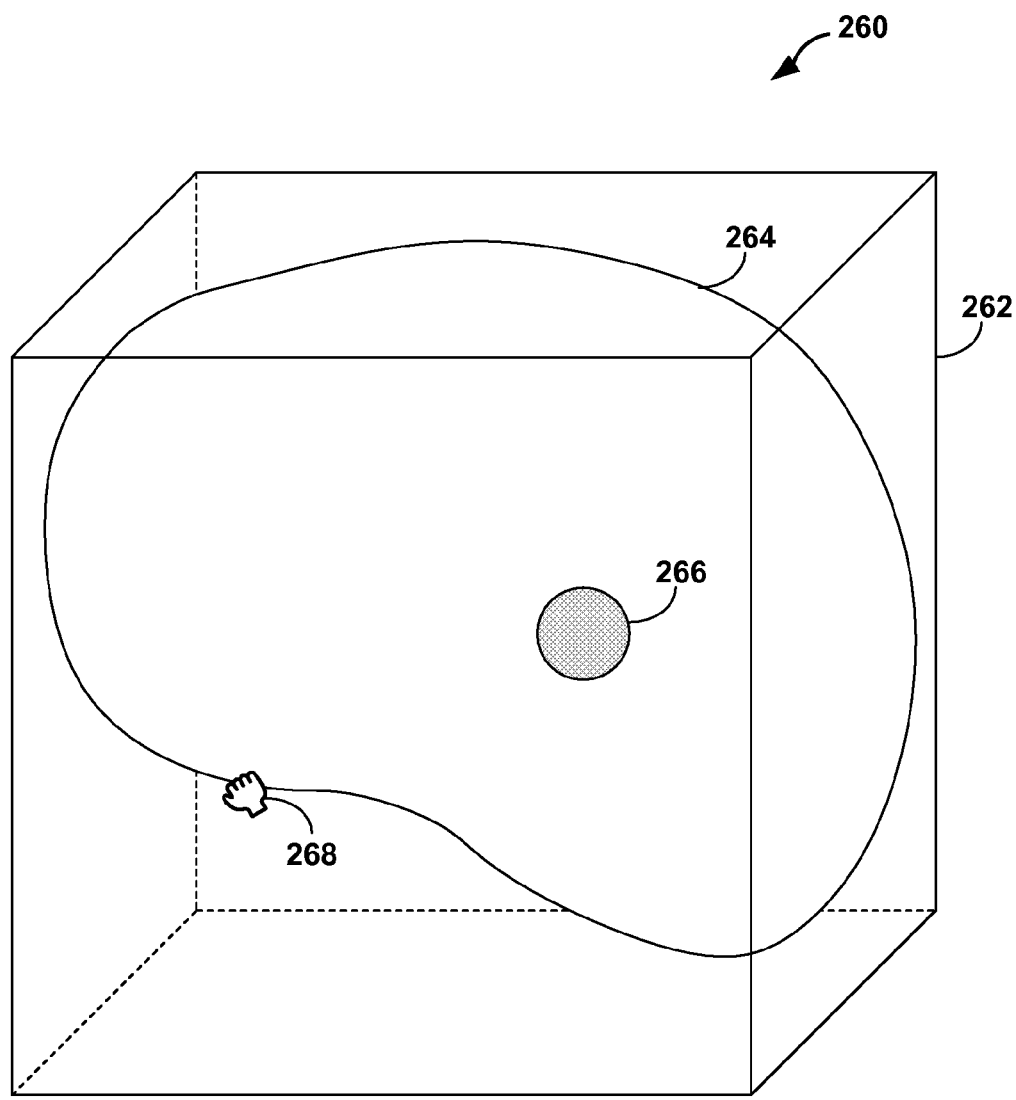
FIG. 16 is a conceptual diagram illustrating a three-dimensional (3D) visualization environment including a 3D brain model for defining a 3D stimulation field and an algorithmic model of a baseline therapy field.

An algorithmic model of a therapy field may also be generated within a 3D environment. FIG. 16 is a conceptual diagram illustrating a 3D environment including a 3D brain model for defining and visualizing a 3D stimulation field. As shown in FIG. 16, GUI 260 presents a 3D environment 262 that illustrates brain model 264, stimulation field 266, and hand 268. In the example shown in FIG. 16, stimulation field 266 is illustrated as a 3D volumetric field. Stimulation field 266 may be stored as an algorithmic model of a baseline therapy field, where stimulation field 266 is generated based on patient anatomy, hardware characteristics of therapy system 10, and the stimulation parameter values of the first therapy program. However, in some cases, the stimulation parameters of the first therapy program may be selected to achieve stimulation field 266. Thus, in such cases, stimulation field 266 may be generated based on patient anatomy and hardware characteristics of therapy system 10. GUI 260 may be presented by processor 60 on display 122 of programming device 110. Brain model 264 is a 3D anatomical region and stimulation field 266 is a 3D stimulation field displayed relative to brain model 264. A user may interact with GUI 260 to move hand 268 in order to control the view and aspects of 3D environment 262. In the example shown in FIG. 16, brain model 264 is positioned to illustrate a sagittal view.

3D environment 262 may be displayed on a 2D display by using partially transparent surfaces and grey or color shades. A fully interactive 3D environment 262 may allow a clinician to view within brain model 264 and identify anatomical regions that are targets for stimulation therapy. Brain model 264 may be generated from imaging data from MRI, CT, or another medical imaging modality. While shading of brain model 264 is not shown in FIG. 16, brain model 264 may include shading or other techniques for illustrating different anatomical regions of brain 18.

While a lead icon representing lead 16 is not shown within 3D environment 262, processor 60 may incorporate imaging data into 3D environment 262 after lead 16 is implanted. That is, processor 60 may automatically recognize the orientation and location of lead 16 within patient 12 based on imaging data input into programming device 110, and may present a lead icon within GUI 260 based on the actual orientation and location of lead 16 within patient 12. Alternatively, the user may manually place a lead icon within 3D environment 262 based upon stereotactic data or implant coordinates for the actual lead 16 implanted within patient 12.

Processor 60 may control the presentation of GUI 260 and select the location of stimulation field 266 based upon the implant site of lead 16 within patient 12. A user may then interact with GUI 260 to adjust and manipulate stimulation field 266 as desired with hand 268 or other input mechanisms provided by user interface 112 of programming device 110 (FIG. 7). The user may also use hand 268 to rotate and spin brain model 264 in any direction. GUI 260 may support zooming in and out relative to brain model 264, as well as displaying different perspectives of brain model 264 within 3D environment 262 to see stimulation field 266 within brain model 264 from different perspectives.

GUI 260 may include a wand tool that allows the user to highlight various regions of brain model 264 to be included in stimulation field 266. The wand tool may automatically select voxels (i.e., pixels in all three dimensions). In other dimensions, the clinician may grab one of several predefined stimulation field shapes and place the shape within brain model 264 to become stimulation field 266 or select specific brain structures for stimulation. In any case, GUI 260 may set limits to stimulation field 266 based upon the characteristics of lead 16 and the capabilities of IMD 14. Patient 12 safety may also govern the size and location of stimulation field 266.

In some examples, GUI 260 may display one or more distinct brain structures within brain model 264. The brain structures may identify the one or more brain structures that include target tissue sites for therapy delivery and/or one or more brain structures to which therapy delivery should be avoided.

Figure 17:
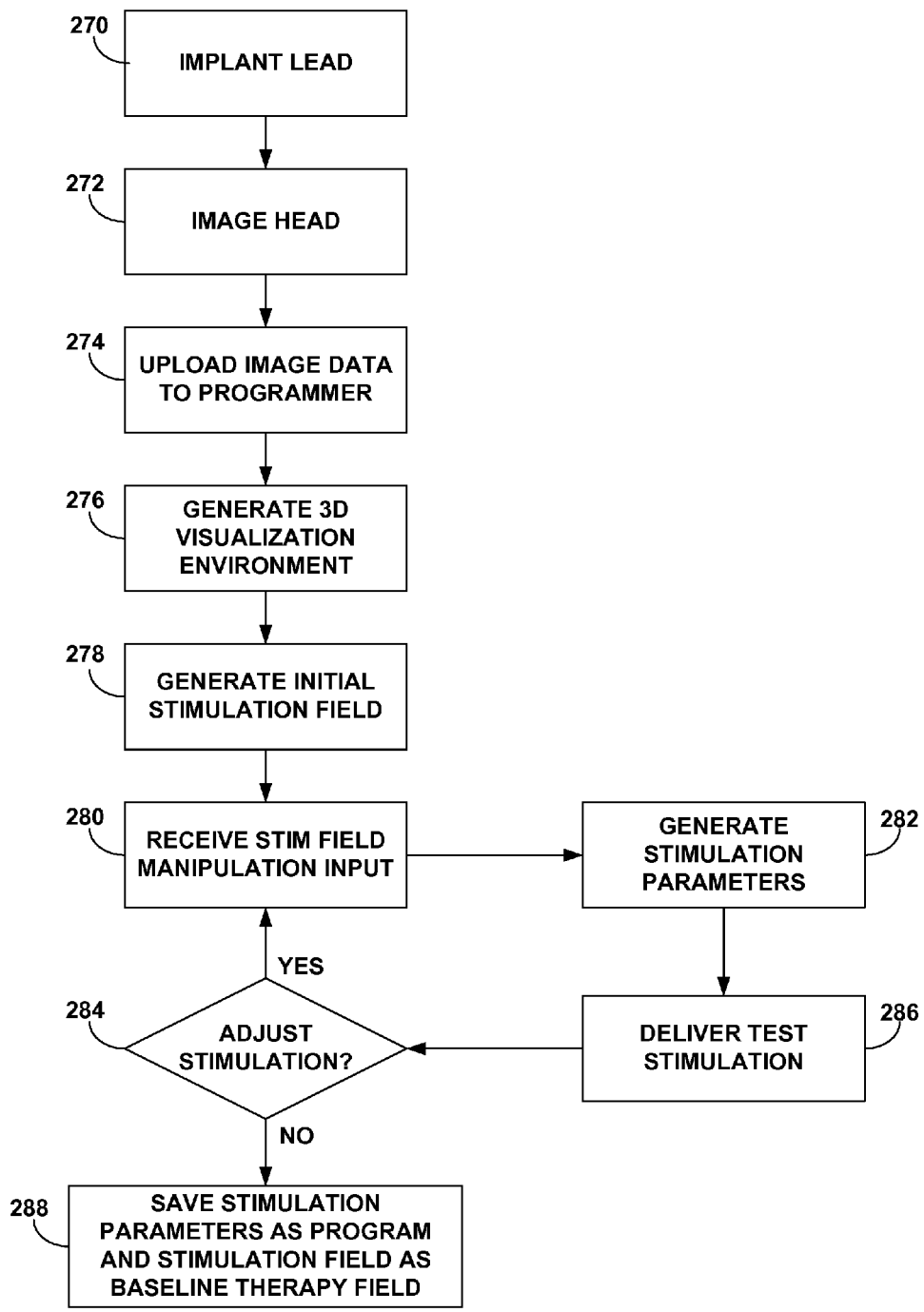
FIG. 17 is a flow diagram illustrating an example technique for defining a 3D stimulation field within a 3D brain model of patient 12.

FIG. 17 is a flow diagram illustrating an example technique for defining a 3D stimulation field within a 3D brain model of patient 12. As shown in FIG. 17, a user, such as a clinician, may implant lead 16 within brain 18 using any suitable technique, such as a stereotactic technique (270). The clinician images the head of patient 12 to obtain data of brain 18 necessary for generating the brain model 264 (272). The clinician may upload the image data to a computing device, such as programming device 110 (274). For example, the image data may be stored within patient anatomy data section 74 of memory 114 (FIG. 7). Processor 60 of programming device 110 generates a 3D visualization environment (276) and generates brain model 264 and the initial stimulation field 266 within the 3D environment (278). In some examples, processor 60 may generate the 3D environment and brain model using techniques described in by Butson et al. in "Patient-Specific Analysis of the Volume of Tissue Activated During Deep Brain Stimulation," (Neuroimage. 2007 Jan. 15; 34(2): 661-670). The initial stimulation field may be generated with a set of stimulation parameters that are believed to provide efficacious therapy to patient 12 for the particular patient condition. These initial stimulation parameters may be specific to patient 12 or may be general to more than one patient.

With the aid of user interface 112 of programming device 110 (FIG. 7), processor 60 receives stimulation field input from a clinician, such as adjustments and manipulations to stimulation field 266 within the 3D environment (280). Processor 60 generates stimulation parameters according to stimulation field 266 resulting from the adjustments and manipulations from the user (282) and controls IMD 14 to deliver test stimulation with the parameters (286). If the clinician desires to adjust stimulation parameters (284) based on the feedback from patient 12 and/or sensors, processor 60 may continue receiving stimulation field input (280) manipulating the representation of the 3D image presented to the user, e.g., via GUI 260 (FIG. 16) and testing the stimulation according to the modification to stimulation field 266 (282, 286). If the stimulation therapy is effective, the clinician may save the stimulation parameters in IMD 14 so that patient 12 can receive therapy with the parameters (288). In addition, stimulation field 266 may be stored within IMD 14 or programming device 110 as a baseline therapy field model.

In addition to or instead of using stimulation field 266 as an algorithmic model of a therapy field, an electrical field model and/or activation model may be generated based on stimulation field 266 and stored as an algorithmic model of the therapy field. The electrical field model and activation field model may be generated by processor 60 using any suitable technique, such as the techniques shown in FIGS. 11 and 12, and displayed within 3D environment 262 using any suitable technique, such as those described in U.S. Pat. No. 7,822,483 to Stone et al. The clinician or other user may modify the stimulation parameter values by directly modifying the size, shape or location of the electrical field model or activation field model within 3D environment 262, or the clinician may modify the electrical field model or activation field model may directly modifying the stimulation parameter values.

As previously discussed, in one technique for generating a second therapy program for modified therapy system 102 (FIG. 6B) based on an algorithmic model of a baseline therapy field and the hardware characteristics of modified therapy system 102, processor 60 of programmer 110 or another computing device may generate stimulation parameter values that may substantially achieve at least one field characteristic of the baseline therapy field model. For example, processor 60 may use information defined by the algorithmic model of the baseline therapy field to automatically generate stimulation parameter values for modified therapy system 102. The algorithmic model of the baseline therapy field may define, for example, the dimensions of the stimulation field in the form of a 3D vector field identifying the distances from lead 16 that stimulation may reach. Processor 60 may use a 3D vector field with an equation approximating electrical current propagation within brain 18 tissue. The resulting data determines the electrode combination and respective values for the voltage or current amplitudes, pulse rates, and pulse widths needed for reproducing the stimulation field within patient 12. In some examples, processor 60 may interpret density of tissue in the imaging data to more precisely approximate the stimulation parameters.

In another example, processor 60 may generate the second therapy program with the aid of stimulation templates, which are predetermined stimulation volumes that are each defined by a set of stimulation parameter values specific to modified therapy system 102. That is, a set of stimulation parameter values (e.g., a therapy program) may control modified therapy system 102 to deliver therapy to patient 12 in order to generate a particular stimulation volume associated with a stimulation template. Memory 114 of programmer 110 may store a certain number of stimulation templates that are used to automatically generate stimulation parameters that best fit a user defined stimulation field, e.g., the baseline therapy field model.

FIGS. 18A-18D are conceptual diagrams illustrating possible cross-sections of stimulation templates for electrodes of two adjacent levels of a complex electrode array geometry. Processor 60 may generate a therapy program for modified therapy system 102 that has at least one field characteristic that is substantially similar to an algorithmic model of a baseline therapy field by matching the stimulation templates shown in FIGS. 18A-18D to the algorithmic model of the baseline therapy field. Each stimulation template may be based upon any one or combination of modeled data, experimental data, or analytical calculations prior to being stored in programmer 20. Cross-sections of example stimulation templates are provided to illustrate possible fields around the circumference of implanted lead 300, which includes segmented electrodes 302A-302D.

FIGS. 18A-18D illustrate possible cross-sections of stimulation templates of an electrode of lead 300, which is paired to another electrode at another electrode level at the same circumferential position. A stimulation template may not indicate the exact shape of the resulting stimulation field because the tissue adjacent to the electrode may affect the propagation of the electrical stimulation. While generally bipolar electrode combinations are described herein, volumetric stimulation templates may include unipolar electrode configurations. Unipolar electrodes may be anodes or cathodes located on a lead that are combined with an electrode that is located on the housing of IMD 104 (FIG. 6B) of modified therapy system 102 (or another location remote from lead 16) to complete the circuit for delivery of electrical stimulation to the patient.

Figures 18A, 18B:
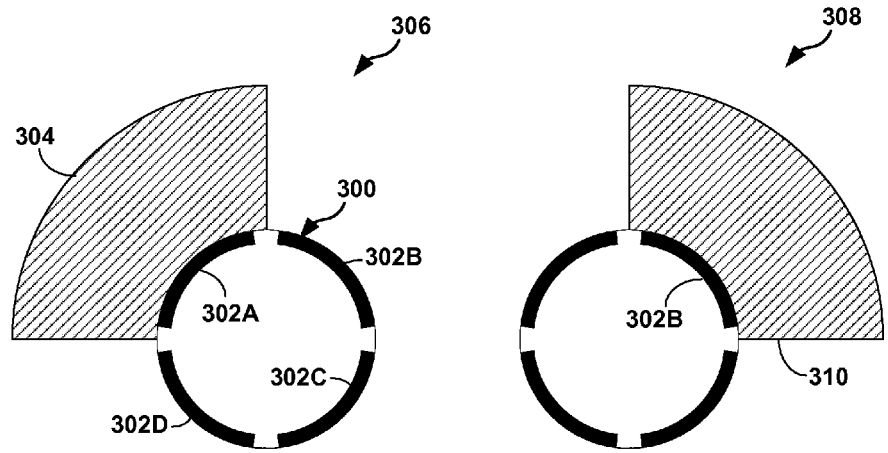
FIGS. 18A-18D are conceptual diagrams illustrating possible stimulation templates for each electrode of a complex electrode array geometry.
Figures 18C, 18D:
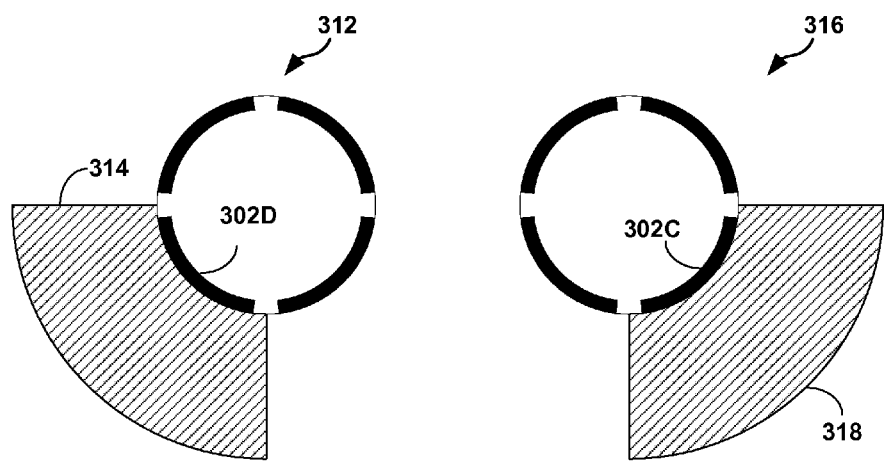

FIG. 18A illustrates a stimulation template 306 generated by electrode 302A and corresponding cross-section of idealized stimulation field 304. FIG. 18B illustrates template 308, which includes electrode 302B and corresponding cross-section of idealized stimulation field 310. FIG. 18C includes stimulation template 312 which includes electrode 302D and corresponding cross-section of idealized stimulation field 314 adjacent to electrode 302D. FIG. 18D indicates that stimulation template 316 includes electrode 302C and corresponding cross-section of idealized stimulation field 318.

The actual shape of each stimulation template 306, 308, 312, 316 may vary depending upon the tissue proximate to the implanted lead 300. However, processor 60 may use the idealized stimulation templates as approximate stimulation templates for the purpose of matching the best template to the algorithmic model of a baseline therapy field. For all stimulation templates, processor 60 may be able to adjust the current amplitude or voltage amplitude to alter the size of the stimulation field provided by the stimulation template to better match the algorithmic model of the baseline therapy field. In addition, processor may combine any of the stimulation templates 306, 308, 312, 316 to stimulate tissue at certain locations around a lead. In some examples, polarity of an electrode of a stimulation template may be changed to accommodate the combine stimulation templates, or stimulation template set (i.e., a grouping of more than one stimulation template).

Figure 19:
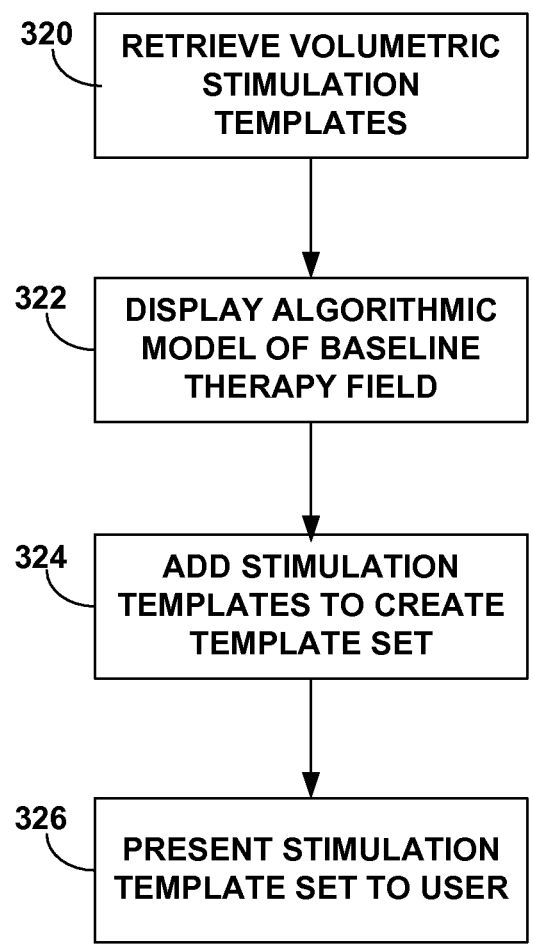
FIG. 19 is a flow diagram illustrating an example technique for generating a therapy program with the aid of volumetric stimulation templates.

FIG. 19 is a flow diagram illustrating an example technique for creating a template set from volumetric stimulation templates stored in programmer 20 in order to generate a therapy program for a modified therapy system 102 (FIG. 6B) that results in a substantially similar therapy field as that generated therapy system 10 with a first therapy program. Processor 60 of programmer 20 retrieves one or more volumetric stimulation templates from memory 114, where the stimulation templates best correlate to the algorithmic model of the baseline therapy field, which is also stored in memory 114 (320). Each stimulation template may be stored as a volumetric stimulation template and processor 60 may compare each stimulation template to the algorithmic model of the baseline therapy field.

In some cases, processor 60 may use an iterative process to find the best one or more stimulation templates that fit the algorithmic model of the baseline therapy field, e.g., step-by-step narrowing of templates according to most important variables first and less important variables next. In other examples, processor 60 may use a point field in which each template is labeled with the points the template includes. The template, or templates, with points most closely matching the algorithmic model of the baseline therapy field may be selected. Storing volumetric stimulation templates may effectively reduce the time needed to generate a second therapy program by providing a starting point for determining useful therapy parameter values for achieving a therapy field similar to the algorithmic model of the baseline therapy field.

In some cases, processor 60 displays the algorithmic model of the baseline therapy field in conjunction with an image of the relevant patient anatomy and a lead icon (322). The algorithmic model of the baseline therapy field may be shown in a 3D view or in a 2D view, which illustrates a cross-section of the baseline therapy field model. The relevant patient anatomy, i.e., the patient anatomy illustrating the target tissue sites for stimulation, may be generated from any suitable medical imaging technique, such as MRI, CT, or PET. As previously indicated, a lead icon may be placed relative to the image of the patient anatomy based on information from a stereotactic lead implantation techniques or a post-implant image of the lead with respect to the anatomy.

Processor 60 may add stimulation templates to the displayed image of the algorithmic model of the baseline therapy field (324), to create the "best fit" stimulation template set to treat patient 12, e.g., the stimulation template set that best matches a field characteristic of the algorithmic model of the baseline therapy field. Processor 60 may present the stimulation template set to the user for review and verification (326). The user may confirm that the one or more field characteristics of the stimulation field defined by the stimulation template set substantially match the one or more field characteristics of the algorithmic model of the baseline therapy field.

Each stimulation template may be stored as a set of equations that govern the template. For example, variables of the template equations may be stimulation parameters such as voltage amplitude, current amplitude, pulse rate, pulse width, or frequency. A clinician may change proposed stimulation parameters by modifying the stimulation field input or directly changing the size of the stimulation template by interacting with user interface 112 of programmer 20. Changes in the stimulation field input will affect the size or selection of the stimulation template set, and changes in the size of the stimulation template will affect the stimulation parameter values of the second therapy program. Other variables may include physical parameters such as electrode size, shape, and curvature.

In other examples, each electrode of the lead of modified therapy system 102 may have a predefined number of possible templates that are defined by predetermined stimulation parameters. In this manner, processor 60 may select the one or more templates that best fits defined stimulation field from the clinician and create a stimulation template set that best fits the algorithmic model of the baseline therapy field. In some examples, system 10 may store and process stimulation templates differently. For example, the clinician may even search memory 114 of programming device 110 (FIG. 7) for possible templates to manually create a stimulation template set or adjust a previously created stimulation template set.

Figure 20A:
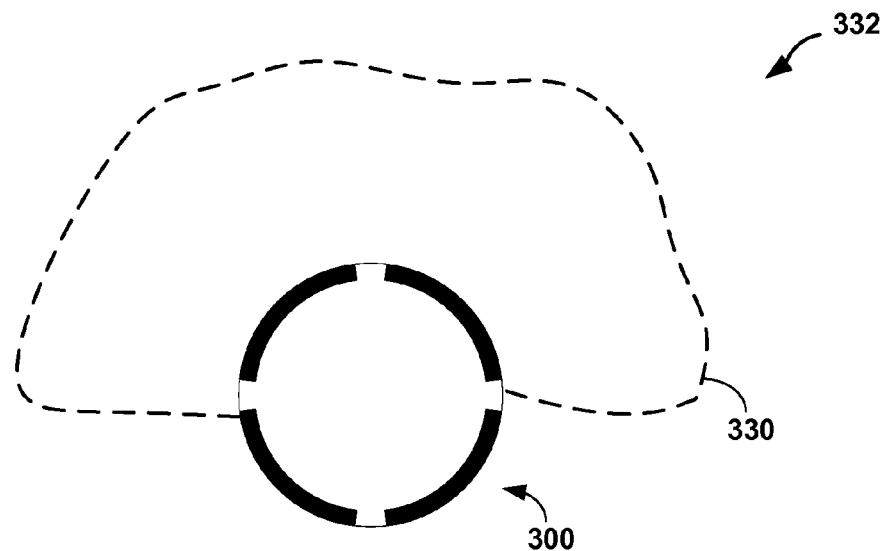
FIGS. 20A and 20B are conceptual diagrams illustrating a template set that does not target any tissue outside of a stimulation area defined by an algorithmic model of a baseline therapy field.
Figure 20B:
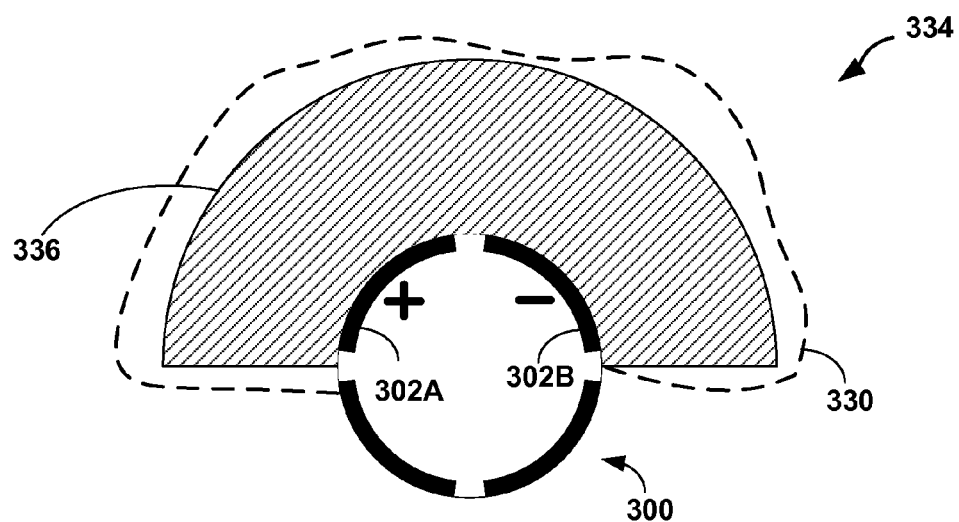

FIGS. 20A and 20B are conceptual diagrams illustrating a template set generated by processor 60 of programmer 110, where the template set does not target any tissue outside of a stimulation area defined by an algorithmic model of a baseline therapy field 330. As shown in FIG. 20A, algorithmic model of baseline therapy field 330 is presented relative to a level of electrodes 302A-302D of lead 300 in view 332, which may be a view of lead 300 presented on user interface 112 of programmer 110. Baseline therapy field model 330 may be, for example, a stimulation field 330 that outlines the area of an anatomical region (not shown) that is stimulated upon delivery of therapy by therapy system 10 according to a first therapy program. For example, the clinician may select baseline therapy field model 330 using the techniques described above with respect to FIGS. 8-17 and subsequently select therapy parameter values for therapy system 10 that may achieve at least one field characteristic of baseline therapy field model 330, or the clinician may select therapy parameter values and then subsequently generate resulting algorithmic model of baseline therapy field 330 with the aid of programmer 110.

FIG. 20B illustrates another view 334, which illustrates stimulation template set 336 that processor 60 creates based on algorithmic model of baseline therapy field 330. Stimulation template set 336 represents the stimulation template set for therapy delivery by modified therapy system 102 (FIG. 6B). In the example of FIG. 20B, processor 60 creates the stimulation template set 336 with an objective of limiting stimulation to within the anatomical region inside the borders of baseline therapy field model 330. The next highest priority for processor 60 is to create a stimulation template set 336 that affects as much of the area within the outer boundaries of baseline therapy field model 330 as possible.

In the example shown in FIG. 20B, template set 336 is created by an anode electrode 302A and cathode electrode 302B of lead 300. While a larger template set 336 may be able to stimulate more of the area within stimulation field 330, the additional stimulated tissue may cause undesirable side effects to patient 12. The clinician may use the similar process for each level of lead 330, if lead 330 includes more than one level of electrodes, to treat other areas of the anatomical region along the length of lead 300. In some examples, the priorities of when to avoid non-target tissue, cover non-target tissue, or some combination of covered target and non-target tissue may be variable based upon the type of stimulation therapy or user adjustable.

The stimulation parameter values associated with stimulation template set 336 are specific to the modified therapy system 102. As previously indicated, modified therapy system 102 may include a different electrode arrangement or an IMD 104 with a different energy threshold value, which affects the therapy parameter values that may be selected to achieve the stimulation field defined by template set 336. The hardware characteristics of modified therapy system 102 are stored within memory 114 (FIG. 7) of programmer 110, and, accordingly, processor 60 may consider the limitations of modified therapy system 102 when generating a second therapy program for therapy delivery by modified therapy system 102.

Figure 21:
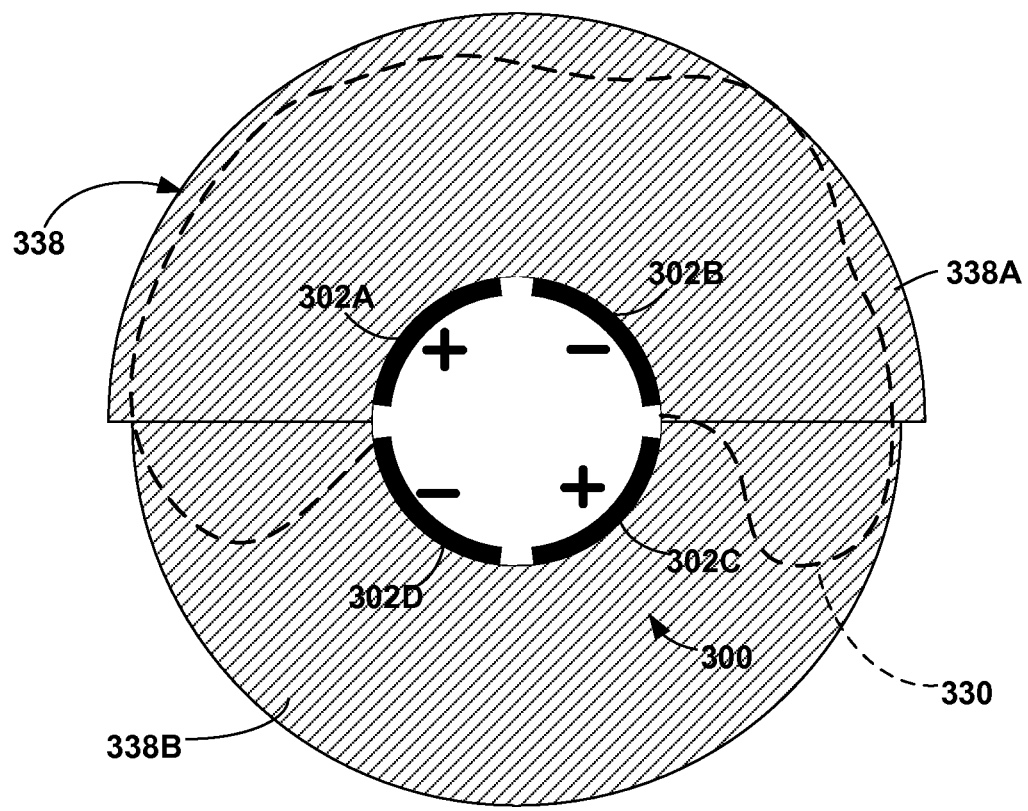
FIG. 21 is a conceptual diagram illustrating a template set that targets all tissue within a stimulation area defined by an algorithmic model of a baseline therapy field.

If desired, processor 60 may use a different set of rules (which may be stored within memory 114 of programmer 110) to generate a stimulation template set based on the algorithmic model of the baseline therapy field 300. FIG. 21 is a conceptual diagram illustrating another template set 338 that targets all tissue within the boundaries defined by algorithmic model of baseline therapy field 330. In the example shown in FIG. 21, processor 60 creates the stimulation template set 338 based on a set of rules that assigns a higher priority to stimulating all tissue areas within baseline therapy field model 330 than minimizing the area of the stimulation field that traverses outside the boundaries of baseline therapy field model 330. This method of creating template sets may cause side effects to patient 12 with a possible benefit of more efficacious therapy to manage the patient condition.

Template 338 includes a first portion 338A, which is created by an anode electrode 302A and cathode electrode 302B of lead 300, and a second portion 338B, which is created by an anode electrode 302C and cathode electrode 302D of lead 300. Only a cross-section of the volumetric stimulation templates 338A, 338B is displayed in FIGS. 20B and 21, respectively. In addition, templates 338A, 338B are only idealized estimations of the actual stimulation field produced within patient 12.

Figure 22:
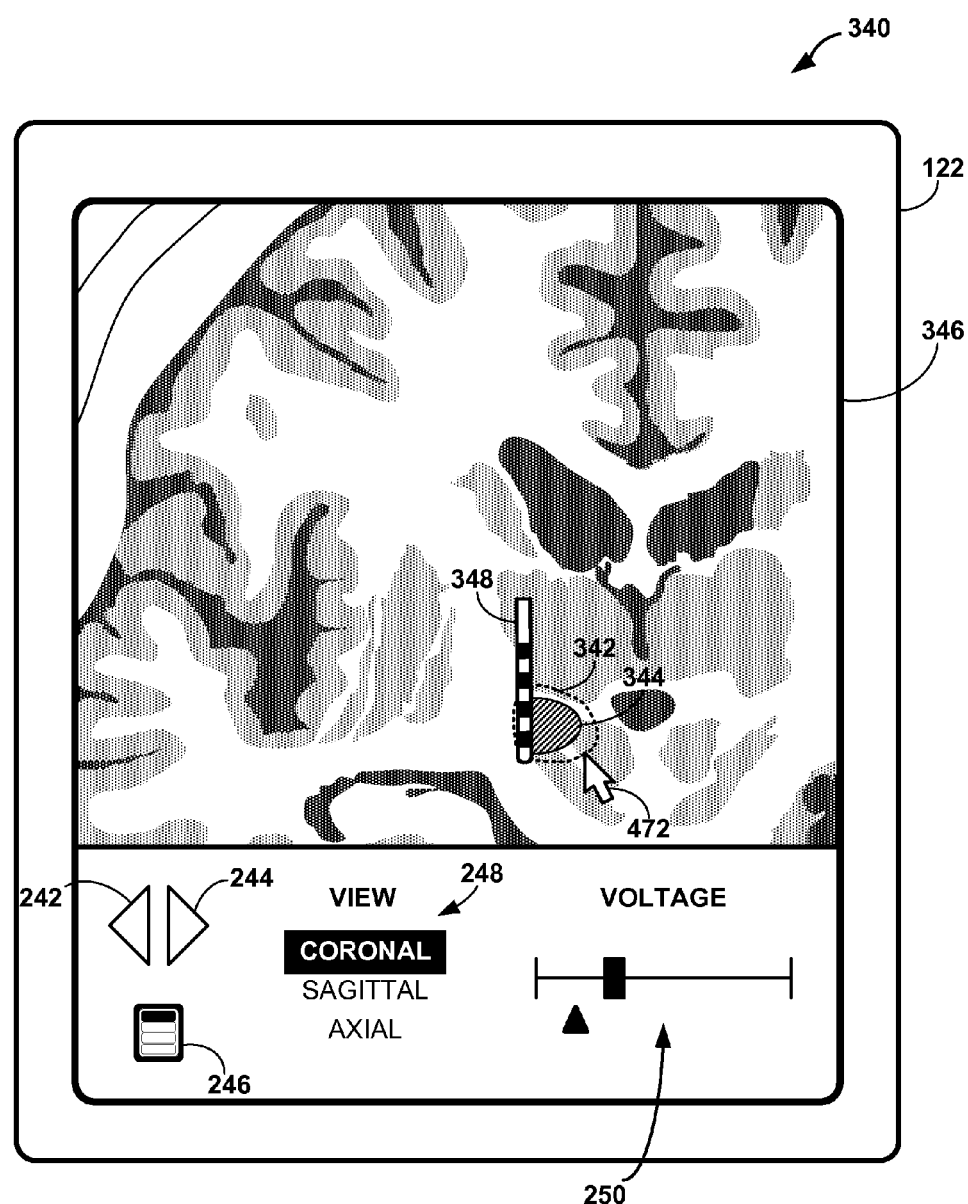
FIG. 22 is an example screen shot of an outline of an algorithmic model of a baseline therapy field and a corresponding template set on a coronal view of brain tissue.

FIG. 22 illustrates an example screen shot of a GUI 340 that provides a 2D view of an anatomical region overlaid with an algorithmic model of a baseline therapy field 342 and corresponding best fit stimulation template set 344. In particular, processor 60 presents coronal view 346 of brain tissue of brain 18 to a user via display 122 of user interface 112 of programming device 110 (FIG. 7). Just as with GUI 240 of FIG. 15, GUI 340 includes previous arrow 242, next arrow 244, menu 246, view indicator 248, and amplitude adjuster 250. Lead icon 348 represents the location of lead 16 of modified therapy system 102 is implanted within patient 12.

After modifying therapy system 10, processor 60 may present GUI 340 to a user along with a stored algorithmic model of baseline therapy field 342, which is presented relative to lead icon 348. Algorithmic model of baseline therapy field 342 represents an efficacious stimulation field, electrical field, activation field or the like, for therapy delivery by modified therapy system 102 (FIG. 6B). With the aid of algorithmic model of baseline therapy field 342, processor 60 generates a second therapy program for modified therapy system 102. Processor 60 selects the parameter values for the second therapy program to achieve at least one field characteristic that is substantially similar to algorithmic model of baseline therapy field 342.

In the example shown in FIG. 22, processor 60 creates, e.g., by retrieving or selecting from memory 114 (FIG. 7), a stimulation template set 344 that best fits the volume of algorithmic model of baseline therapy field 342. Modified therapy system 102 may be associated with a predefined set of stimulation templates from which the selection of stimulation template set 344 may be made. For example, the predefined set of stimulation templates may be limited based on the capabilities (e.g., the energy threshold value) of IMD 104 (FIG. 6B). Baseline therapy field model 342 and stimulation template set 344 are each cross-sectional views of a volumetric stimulation field and a volumetric stimulation template, respectively. After the clinician has only defined one cross-section of the volumetric stimulation field, processor 60 may estimate the volume and modify the estimation with further input from the clinician in other orthogonal views.

Processor 60 is governed by instructions stored in memory 114 of programmer 110. In some examples, the instructions indicate that stimulation template set 344 should cover as much volume (or area, in a cross-sectional view) within algorithmic model of baseline therapy field 342 without affecting any area of the anatomical region outside of the outer boundaries defined by algorithmic model of baseline therapy field 342. In this manner, all regions of the target anatomical structure of patient 12 may not be covered by the electrical stimulation. However, the rule limiting the stimulation to within the outer boundaries defined by algorithmic model of baseline therapy field 342 may help limit undesirable side effects resulting from stimulation delivery to regions outside of the outer boundaries defined by algorithmic model of baseline therapy field 342. As discussed above, in other examples, processor 60 may be governed by instructions stored in memory 114 that define how the stimulation template set must correlate to at least one other field characteristic of algorithmic model of baseline therapy field 342. In other cases, the instructions may cause processor 60 to select a stimulation template set that at least covers the volume of algorithmic model of baseline therapy field 342.

If desired, the clinician or other user may modify the size of algorithmic model of baseline therapy field 342 prior to generating the second therapy program for modified therapy system 102. For example, the clinician may use the modification to therapy system 10 as an opportunity to modify an aspect of therapy delivery, such as the area of stimulation, centroid of stimulation or the like. The clinician may increase or decrease the overall area of algorithmic model of baseline therapy field 342 from the origin of lead icon 348 by adjusting the voltage with amplitude adjuster 250. Amplitude adjuster 250 is an analog adjustment mechanism and may also be in the form of an adjustment knob instead of the slider. As the size of algorithmic model of baseline therapy field 342 changes, the resulting best fit stimulation template set 344 may change, e.g., processor 60 may select a better fitting template set.

In other examples, a new stimulation template set that fits the changes algorithmic model of baseline therapy field 342 may only be provided if the user accesses certain options within menu 246 to request programmer 20 try to identify a new stimulation template set. In addition, the clinician may view other coronal slices of the anatomical region by selecting previous button 242 or next button 244 that move to a different depth of the anatomical region. In some examples, processor 60 may extrapolate algorithmic model of baseline therapy field 342 and stimulation template 344 into other coronal slices of the anatomical regions if the clinician changes the slice. In other examples, lead icon 348 may be present in other slices, but algorithmic model of baseline therapy field 342, stimulation template 344, or both, may not be present until the clinician defines the stimulation in at least one more orthogonal view so that processor 60 can generate the volumetric stimulation field and template.

Figure 23:
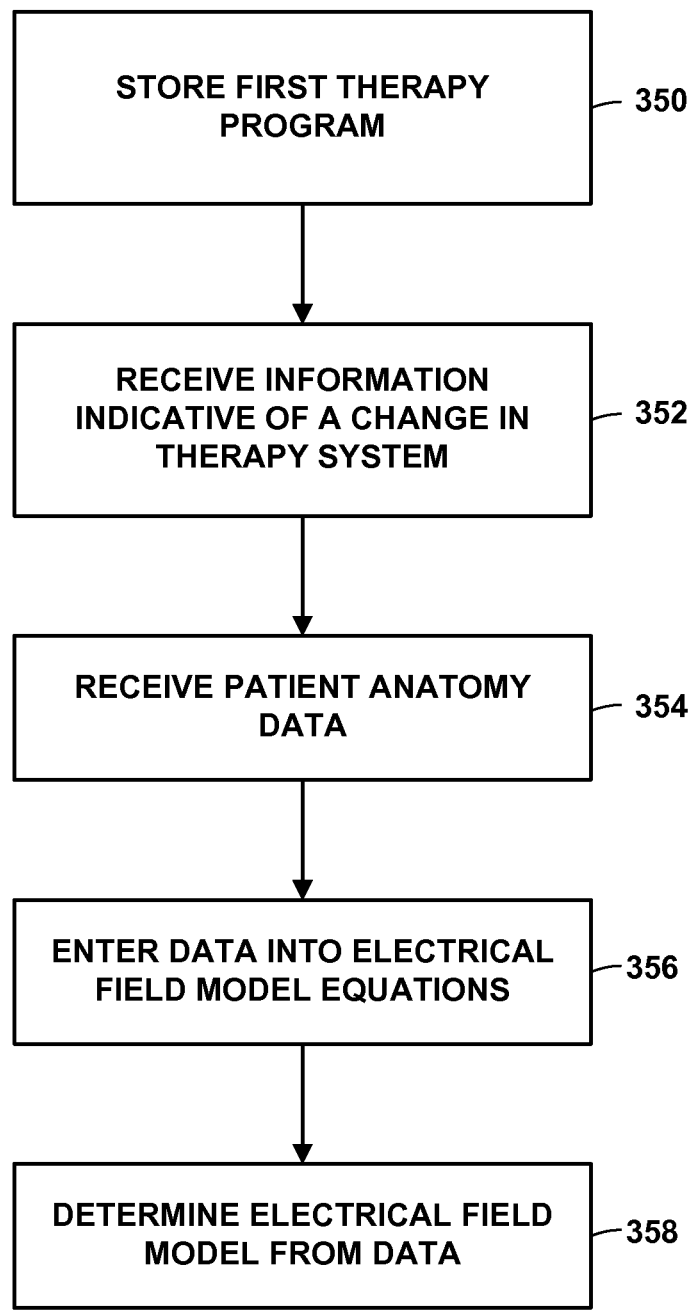
FIG. 23 is a flow diagram illustrating an example technique for generating the algorithmic model of a therapy field based on information indicative of a change in a therapy system.

As discussed with respect to FIG. 5B, in one technique for modifying a therapy program based on information indicative of a change to therapy system 10, processor 60 of programming device 110 (or programmer 20) may generate an algorithmic model of a second therapy field based on a first therapy program and the information indicative of the modification to therapy system 10. FIG. 23 is a flow diagram illustrating one technique for generating the algorithmic model of the second therapy field, where the algorithmic model is an electrical field model. In other examples, processor 60 may generate an activation field model in addition to or instead of the electrical field model in order to generate the algorithmic model of the second therapy field.

Processor 60 stores the first therapy program in memory 112 of device 110 (350), which may be the therapy program determined to provide efficacious therapy to patient 12 when therapy is delivered by therapy system 10. Processor 60 receives information indicative of a modification to therapy system 10 (352), such as the replacement of IMD 14 with another medical device or the replacement of implanted lead 16 with one or more leads. The modification to therapy system 10 may affect the stimulation delivered to patient 12. Processor 60 receives patient anatomy data (354), such as by retrieving the data from the stored data 94 (FIG. 7).

Processor 60 may enter the patient anatomy data, the first therapy program, and new hardware characteristics of modified therapy system 102, such as a new energy threshold value of IMD 104, the number and spacing of the electrodes of a new lead, and the like, into electrical field model equations that define how the electrical field propagates from an origin location, i.e., the electrodes of the one or more implanted leads of modified therapy system 102 (356). Processor 60 then determines the estimated electrical field that will be produced in therapy to generate the algorithmic model of the electrical field (358). In some cases, processor 60 may cause the electrical field model to be displayed to a user via display 122.

Based on the electrical field model equations, processor 60 may determine how the modified therapy system 102 affects the electrical field that results from therapy delivery according to the first therapy program. For example, if the information indicative of the modification to therapy system 10 indicates that IMD 104 has replaced IMD 14, and that IMD 104 has a smaller energy threshold value than IMD 14, the electrical field model equations may implement an algorithm that estimates how the limitations to the total energy affect the stimulation signals that modified therapy system 102 may deliver, and, therefore, the characteristics of any resulting electrical field.

While the description primarily refers to electrical stimulation therapy, in some cases, a therapy program for a therapeutic agent delivery system may be generated based upon a modification to a therapy system. A therapeutic agent delivery system may be modified, for example, by replacing the therapeutic agent delivery device (e.g., a drug pump) or the therapy delivery element (e.g., a catheter). An algorithmic model of a baseline therapy field, which may be generated based upon the delivery of a therapeutic agent to a target tissue site within patient with a first therapy system, may be used to generate a second therapy program for a modified therapy system.

In the case of therapeutic agent delivery, the therapy parameters may include the dosage of the therapeutic agent (e.g., a bolus size or concentration), the rate of delivery of the therapeutic agent, the maximum acceptable dose in each bolus, a time interval at which a dose of the therapeutic agent may be delivered to a patient (lock-out interval), and so forth. Information indicative of a modification to a therapeutic agent delivery system may indicate hardware characteristics, such as the reservoir capacity of a new fluid delivery device, the bolus size or frequency capability of the new fluid delivery device, the lock-out period of the new fluid delivery device, the size and capacity of a fluid delivery lumen of a new catheter, the type of therapeutic agent(s) delivered to the patient, and the like. Example therapeutic agents include, but are not limited to, pharmaceutical agents, insulin, pain relieving agents, anti-inflammatory agents, gene therapy agents, or the like.

Just as with the stimulation systems 10, 30 described above, for a therapy system that includes delivery of a therapeutic agent, an algorithmic model of a therapy field may be generated with the aid of modeling software, hardware or firmware executing on a computing device, such as programmer 20, programming device 110, or a separate dedicated or multifunction computing device. An algorithmic model of the baseline therapy field may be a known therapy field that results from delivery of a therapeutic agent to a target tissue site according to at least one therapy program determined to deliver efficacious therapy to the patient, and is also based on an anatomical data set, such as tissue density data, body fluid pressure, body fluid flow rates, body fluid diffusion rates, and effective duration of the therapeutic agent on the target tissue. Again, the anatomical data set may be specific to the patient or may be general to more than one patient. The anatomical data set comprises at least one of an anatomical image of a patient, a reference anatomical image, an anatomical atlas or a tissue conductivity data set.

In some cases, the algorithmic model of a therapy field resulting from delivery of a therapeutic agent may indicate the anatomic structures or the tissue area that are affected by the therapeutic agent. For example, if the therapeutic agent delivers a genetic material to a target tissue site within a patient, where the genetic material causes transgene expression by tissue at the stimulation site, the therapy field may indicate the region of tissue that results in the transgene expression. The transgene expression may include an increased expression of proteins, such as connexins, gap junctions, and ion channels, to increase the conductivity of the tissue at the target tissue site, or the delivered genetic material may cause expression of a metalloproteinase, an anti-inflammatory agent, or an immunosuppressant agent.

As another example, if the therapeutic agent delivers a pain relieving agent to a target tissue site within a patient, the algorithmic model of the therapy field may indicate the region of tissue that absorbs the pain relieving agent and/or the region of paresthesia or other physiological effects that may result from delivery of the therapeutic agent to the target tissue site.

The algorithm for generating an algorithmic model of a therapy field resulting from delivery of one or more therapeutic agents may be generated with the aid of computer modeling techniques. The algorithmic model of the therapy field may indicate the diffusion of the therapeutic agent through the patient's body from a therapy delivery element. The algorithmic model may be an algorithmic model that is generated based on a patient anatomy, the patient's tissue characteristics, and therapeutic agent delivery parameter values. In one example, the algorithm includes equations that define drug propagation through the patient's tissue based on the physical tissue characteristics (e.g., density) and body fluid flow, pressure, and diffusion characteristics adjacent the therapy delivery element. The drug propagation equations may be specific to patient 12 or may be based on information not specific to patient 12. From this information, processor 60 of programming device 110 may be able to generate the estimated therapeutic agent propagation field that will be produced in therapy.

In relatively static body fluids, such as like the spinal cord fluid (SCF), the drug propagation equations may define a simple diffusion model coupled with a model of the therapeutic agent's effective duration within the patient's body. Physiological parameters such a pressure at the target tissue site may impact the diffusion rate. In relatively fluid body fluids, such as the blood stream, the drug propagation equations may define a diffusion model that also considers the body fluid pressure as well as the body fluid flow rate. Generally, these body fluid characteristics, such as flow rate and pressure, may change relatively quickly for a patient, e.g., based on hydration, heart rate, and the like. Accordingly, sensors may be used to regularly determine the body fluid characteristics, and provide feedback to processor 60 (or a processor of the therapeutic agent delivery device or another device), which may then generate an algorithmic model of the diffusion of the therapeutic agent and determine whether one or more parameter values of the therapeutic agent delivery are desirable based on the modeled diffusion.

The techniques described in this disclosure, including those attributed to IMD 14, programmer 20, programming device 110, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 14 and/or processor 60 of programmer 20 or programming device 110, any one or more parts of the techniques described herein may be implemented by a processor of one of IMD 14 or programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The invention claimed is:

1. A method comprising:
    generating an algorithmic model of a baseline therapy field that represents therapy delivery via a first therapy system based on a first user-defined therapy program; and
    automatically generating, by a processor, a second therapy program for a second therapy system based on the algorithmic model of the baseline therapy field, wherein the second therapy system differs from the first therapy system.

2. The method of claim 1, wherein the second therapy system comprises at least one hardware characteristic that differs from the first therapy system, the hardware characteristic comprising at least one of a medical device, a configuration of one or more therapy delivery elements implanted within the patient, or a location of the therapy delivery element within the patient.

3. The method of claim 1, wherein the first therapy system is a first generation therapy system and the second therapy system is a second generation of the first therapy system.

4. The method of claim 1, wherein the first therapy system is a trial therapy system comprising an external medical device, and the second therapy system is a chronic therapy system comprising an implantable medical device.

5. The method of claim 1, wherein generating the algorithmic model of the baseline therapy field comprises:
    receiving an anatomical data set; and
    entering patient data from the anatomical set into an electrical field model equation.

6. The method of claim 5, wherein the anatomical data set comprises at least one of an anatomical image of a target tissue site of the patient, a reference anatomical image, an anatomical atlas, or a map of the tissue characteristics of the target tissue site of the patient.

7. The method of claim 5, wherein the electrical field model equation defines at least one of how an electrical field will propagate through tissue from a medical lead of the first therapy system when the first therapy system delivers the therapy based on the first therapy program or how an electrical field will activate neurons.

8. The method of claim 5, wherein the anatomical data set describes at least one characteristic of tissue of the patient proximate to a therapy delivery element implanted within the patient, and generating the algorithmic model of the baseline therapy field comprises:
    receiving user input indicating at least one of a configuration or a location of the therapy delivery element of the first therapy system;
    receiving user input indicating at least one therapy parameter value of the first therapy program; and
    generating the algorithmic model of the baseline therapy field that represents where the electrical stimulation will propagate from the therapy delivery element based on the anatomical data set, the configuration or location of the at least one therapy delivery element, and the at least one therapy parameter value.

9. The method of claim 1, wherein generating the algorithmic model of the baseline therapy field comprises generating the algorithmic model of at least one of an electrical field, a tissue activation field, a voltage gradient, or a current density that provides efficacious therapy to the patient.

10. The method of claim 1, wherein automatically generating the second therapy program for the second therapy system comprises selecting a therapy parameter value of the second therapy program to substantially maintain at least one field characteristic of the algorithmic model of the baseline therapy field.

11. The method of claim 10, wherein the field characteristic comprises at least one of stimulation area, a tissue activation area, centroid of stimulation, activated neurons, an amplitude of the voltage or current at a spatial point within the stimulation area or a charge density.

12. The method of claim 1, wherein the first therapy program defines values for a plurality of therapy parameters, and automatically generating the second therapy program comprises modifying a value of at least one of the therapy parameter values of the first therapy program.

13. The method of claim 1, wherein automatically generating a second therapy program for a second therapy system comprises:
   selecting at least one volumetric stimulation template from a memory based on the algorithmic model of the baseline therapy field; and
   selecting an electrical stimulation parameter values associated with the selected volumetric stimulation template in the memory.

14. The method of claim 13, wherein selecting at least one volumetric stimulation template comprises selecting the volumetric stimulation template based on a comparison of at least one of the volumes and shapes of the volumetric stimulation template and the user-defined stimulation field.

15. The method of claim 1, wherein the first therapy system is associated with a first patient and the second therapy system is associated with a second patient.

16. A method comprising:
   generating an algorithmic model of a first therapy field based on delivery of therapy by a first therapy system in accordance with a therapy program, wherein the first therapy system comprises a medical device and a therapy delivery element;
   receiving information relating to a modification to at least one of the medical device or the therapy delivery element of the first therapy system, wherein the information defines a modified therapy system;
   generating an algorithmic model of a second therapy field based on delivery of therapy by the modified therapy system in accordance with the therapy program;
   comparing the algorithmic models of the first and second therapy fields; and
   modifying, by a processor, the therapy program based on the comparison between the algorithmic models of the first and second therapy fields.

17. The method of claim 16, wherein comparing the algorithmic models of the first and second therapy fields comprises comparing at least one field characteristic of the first therapy field model and the algorithmic model of the baseline therapy field.

18. The method of claim 17, wherein the first therapy system comprises a stimulation lead, and generating the algorithmic model of the first therapy field comprises determining where electrical stimulation will propagate from the stimulation lead based upon the therapy program and an anatomical data set.

19. The method of claim 16, wherein modifying the therapy program based on the comparison between the algorithmic models of the first and second therapy fields comprises modifying the therapy program to substantially maintain at least one field characteristic of the algorithmic model of the first therapy field.

20. A system comprising:
   a memory that stores a first therapy program and an algorithmic model of a baseline therapy field; and
   a processor that generates the algorithmic model of a baseline therapy field that is based on therapy delivery by a first therapy system in accordance with the first therapy program, and automatically generates a second therapy program for a second therapy system based on the algorithmic model of the baseline therapy field, wherein the second therapy system differs from the first therapy system.

21. The system of claim 20, wherein the algorithmic model is a first algorithmic model, the first therapy system comprises a medical device and a therapy delivery element, the second therapy system comprises a modification to at least one of the medical device or the therapy delivery element of the first therapy system, and the processor receives information indicating the modification to at least one of the medical device or the therapy delivery element of the first therapy system, generates a second algorithmic model of a first therapy field based on delivery of therapy by the modified therapy system in accordance with the first therapy program, compares the first and second algorithmic models, and automatically generates the second therapy program based on the comparison between the first and second algorithmic models.

22. The system of claim 20, further comprising a medical device programmer that comprises the memory and the processor.

23. The system of claim 20, wherein the second therapy system comprises at least one hardware characteristic that differs from the first therapy system, the hardware characteristic comprising at least one of a medical device, a configuration of one or more therapy delivery elements implanted within the patient, or a location of the therapy delivery element within the patient.

24. The system of claim 20, wherein the first therapy system is a first generation therapy system and the second therapy system is a second generation of the first therapy system.

25. The system of claim 20, wherein the first therapy system is a trial therapy system comprising an external medical device, and the second therapy system is a chronic therapy system comprising an implantable medical device.

26. The system of claim 20, wherein the processor generates the algorithmic model of the baseline therapy field by at least entering patient data from an anatomical set into an electrical field model equation that defines how an electrical field will propagate through tissue from a medical lead of the first therapy system when the first therapy system delivers the therapy based on the first therapy program.

27. The system of claim 20, wherein the algorithmic model of the baseline therapy field comprises at least one of an electrical field, a tissue activation field, a voltage gradient, or a current density that provides efficacious therapy to the patient.

28. The system of claim 20, wherein the processor generates the second therapy program for the second therapy system by at least selecting a therapy parameter value of the second therapy program to substantially maintain at least one field characteristic of the algorithmic model of the baseline therapy field.

29. The system of claim 28, wherein the field characteristic comprises at least one of stimulation area, a tissue activation area, centroid of stimulation, activated neurons, an amplitude of the voltage or current at a spatial point within the stimulation area or a charge density.

30. The system of claim 20, wherein the memory stores a plurality of volumetric stimulation templates and the processor selects at least one of the plurality of stimulation templates based on the algorithmic model of the baseline therapy field, and selects an electrical stimulation parameter set associated with the selected volumetric stimulation template in the memory to generate the second therapy program.

31. The system of claim 20, wherein the first therapy system is associated with a first patient and the second therapy system is associated with a second patient.

32. A non-transitory computer-readable storage medium comprising instructions that cause a processor to: generate an algorithmic model of a baseline therapy field that represents therapy delivery via first therapy system based on a first user-defined therapy program; and automatically generate a second therapy program for a second therapy system based on the algorithmic model of the baseline therapy field, wherein the second therapy differs from the first therapy system.

33. The computer-readable storage medium of claim 32, further comprising instructions that cause the processor to generate the second therapy program for the second therapy system by at least selecting a therapy parameter value of the second therapy program to substantially maintain at least one field characteristic of the algorithmic model of the baseline therapy field.

34. The computer-readable storage medium of claim 32, wherein the second therapy system comprises at least one hardware characteristic that differs from the first therapy system, the hardware characteristic comprising at least one of a medical device, a configuration of one or more therapy delivery elements implanted within the patient, or a location of the therapy delivery element within the patient.

35. A system comprising:
means for generating an algorithmic model of a baseline therapy field that represents therapy delivery via a first therapy system based on a first user-defined therapy program; and
means for automatically generating a second therapy program for a second therapy system based on the algorithmic model of the baseline therapy field, wherein the second therapy system differs from the first therapy system.

36. The system of claim 35, wherein the means for automatically generating the second therapy program for the second therapy system generates the second therapy program by at least selecting a therapy parameter value of the second therapy program to substantially maintain at least one field characteristic of the algorithmic model of the baseline therapy field.

37. The system of claim 35, wherein the second therapy system comprises at least one hardware characteristic that differs from the first therapy system, the hardware characteristic comprising at least one of a medical device, a configuration of one or more therapy delivery elements implanted within the patient, or a location of the therapy delivery element within the patient.

38. A system comprising:
a memory that stores a therapy program; and
a processor that generates an algorithmic model of a first therapy field based on delivery of therapy by a first therapy system in accordance with the therapy program, wherein the first therapy system comprises a medical device and a therapy delivery element, receives information relating to a modification to at least one of the medical device or the therapy delivery element of the first therapy system, wherein the information defines a modified therapy system, generates an algorithmic model of a second therapy field based on delivery of therapy by the modified therapy system in accordance with the therapy program, compares the algorithmic models of the first and second therapy fields, and modifies the therapy program based on the comparison between the algorithmic models of the first and second therapy fields.

39. The system of claim 38, wherein the processor compares the algorithmic models of the first and second therapy fields by at least comparing at least one field characteristic of the algorithmic models of the first and second therapy fields.

40. The system of claim 38, wherein the processor modifies the therapy program based on the comparison between the algorithmic models of the first and second therapy fields by at least modifying the therapy program to substantially maintain at least one field characteristic of the algorithmic model of the first therapy field.

41. A system comprising:
means for generating an algorithmic model of a first therapy field based on delivery of therapy by a first therapy system in accordance with a therapy program, wherein the first therapy system comprises a medical device and a therapy delivery element;
means for receiving information relating to a modification to at least one of the medical device or the therapy delivery element of the first therapy system, wherein the information defines a modified therapy system;
means for generating an algorithmic model of a second therapy field based on delivery of therapy by the modified therapy system in accordance with the therapy program;
means for comparing the algorithmic models of the first and second therapy fields; and
means for modifying the therapy program based on the comparison between the algorithmic models of the first and second therapy fields.

42. The system of claim 41, wherein the means for comparing compares the algorithmic models of the first and second therapy fields by at least comparing at least one field characteristic of the algorithmic models of the first and second therapy fields.

43. The system of claim 41, wherein the means for modifying the therapy program modifies the therapy program based on the comparison between the algorithmic models of the first and second therapy fields by at least modifying the therapy program to substantially maintain at least one field characteristic of the algorithmic model of the first therapy field.

* * * * *